(12) United States Patent
Takagi

(10) Patent No.: US 10,513,562 B2
(45) Date of Patent: Dec. 24, 2019

(54) FRAGMENT ANTIBODY AND METHOD FOR CRYSTALLIZING PROTEIN USING FRAGMENT ANTIBODY

(71) Applicants: FUJIFILM WAKO PURE CHEMICAL CORPORATION, Osaka (JP); OSAKA UNIVERSITY, Suita (JP)

(72) Inventor: Junichi Takagi, Suita (JP)

(73) Assignees: FUJIFILM WAKO PURE CHEMICAL CORPORATION, Osaka (JP); OSAKA UNIVERSITY, Suita (JP)

(*) Notice: Subject to any disclaimer, the term of this patent is extended or adjusted under 35 U.S.C. 154(b) by 0 days.

(21) Appl. No.: 16/345,639

(22) PCT Filed: Nov. 7, 2017

(86) PCT No.: PCT/JP2017/040138
§ 371 (c)(1),
(2) Date: Apr. 26, 2019

(87) PCT Pub. No.: WO2018/088403
PCT Pub. Date: May 17, 2018

(65) Prior Publication Data
US 2019/0276561 A1 Sep. 12, 2019

(30) Foreign Application Priority Data
Nov. 9, 2016 (JP) .................... 2016-218631

(51) Int. Cl.
*C07K 9/00* (2006.01)
*C07K 16/46* (2006.01)
*C07K 1/30* (2006.01)

(52) U.S. Cl.
CPC .............. *C07K 16/46* (2013.01); *C07K 1/306* (2013.01); *C07K 2317/56* (2013.01); *C07K 2317/94* (2013.01)

(58) Field of Classification Search
None
See application file for complete search history.

(56) References Cited

PUBLICATIONS

Al-Lazikani et al., "Standard Conformations for the Canonical Structures of Immunoglobulins," *J. Mol. Biol.*, 273(4): 927-948 (1997).
Arimori et al., "Fv-clasp: An Artificially Designed Small Antibody Fragment with Improved Production Compatibility, Stability, and Crystallizability," *Structure*, 25(10): 1611-1622 and e1-e4 [Supplementary Materials] (2017).
Arimori et al., "Design and Structural Analysis of Novel Fragment Antibody Format 'Fv-clasp,'" *15th Protein Science Society of Japan: Abstracts*, p. 116, Abstract 2P-118 (May 26, 2015).
Bird et al., "Single-Chain Antigen-Binding Proteins," *Science*, 242(4877): 423-426 (1988).
Chothia et al., "Canonical Structures for the Hypervariable Regions of Immunoglobulins," *J. Mol. Biol.*, 196(4): 901-917 (1987).
Huston et al., "Protein engineering of antibody binding sites: Recovery of specific activity in an anti-digoxin single-chain Fv analogue produced in *Escherichia coli*," *Proc. Natl. Acad. Sci. U.S.A.*, 85(16): 5879-5883 (1988).
Japanese Patent Office, International Search Report in International Patent Application No. PCT/JP2017/040138 (dated Feb. 6, 2018).

*Primary Examiner* — Jeanette M Lieb
(74) *Attorney, Agent, or Firm* — Leydig, Voit & Mayer, Ltd.

(57) ABSTRACT

An object of the present invention is to provide a fragment antibody which can be conveniently produced as one having antigen-binding activity, and which has a greater ability to crystallize itself alone or as a complex with an antigen molecule than that of Fv-clasp (v1) even in a case where the fragment antibody is obtained in an *E. coli* expression system. The present invention relates to a fragment antibody including a complex of a peptide (VH(112C)-SARAH) in which an N-terminus of a SARAH domain is linked to a C-terminus of a heavy chain domain (VH region) of an antibody, and an amino acid residue of antibody residue 112 according to Chothia numbering scheme in the VH region is mutated to cysteine; and a peptide (VL-SARAH(37C)) in which an N-terminus of a SARAH domain is linked to a C-terminus of a light chain domain (VL region) of an antibody, and an amino acid residue at position 13 from the C-terminus in the SARAH domain is mutated to cysteine.

9 Claims, 11 Drawing Sheets
Specification includes a Sequence Listing.

ANTIGENIC PEPTIDE (C8 PEPTIDE)

ANTIGENIC PEPTIDE (HA PEPTIDE)

(A) (B)

(A) (B)

(A) (B)

(A) (B)

FIG. 15
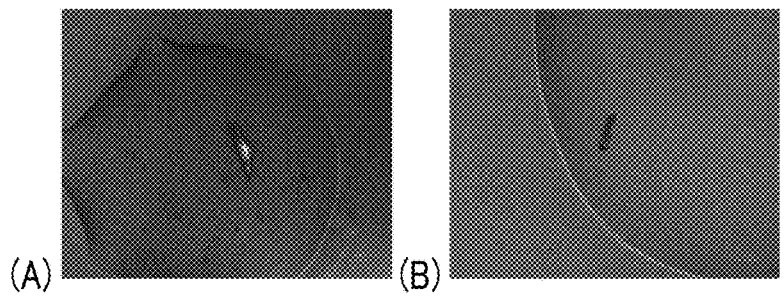
(A)  (B)
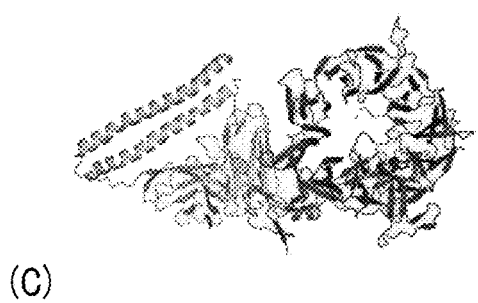
(C)
FIG. 16
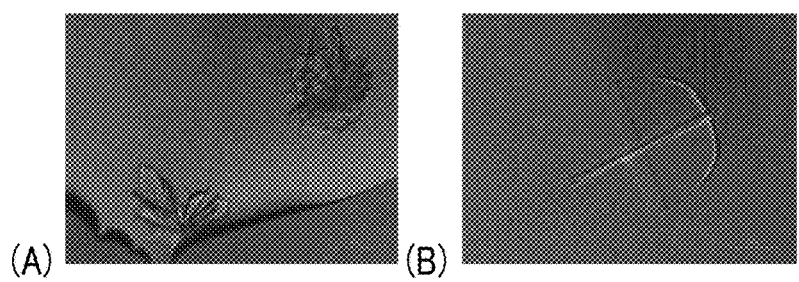
(A)  (B)
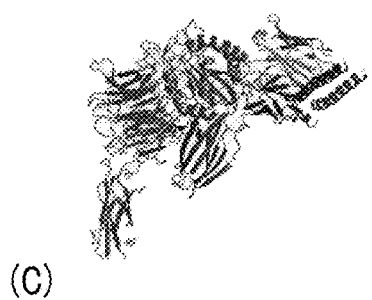
(C)
FIG. 17
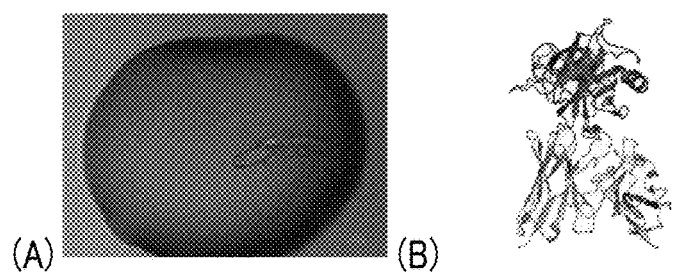
(A)  (B)

SEQUENCE LISTING

<160> NUMBER OF SEQ ID NOS: 89

<210> SEQ ID NO 1
<211> LENGTH: 49
<212> TYPE: PRT
<213> ORGANISM: Homo sapiens

<400> SEQUENCE: 1

Asp Tyr Glu Phe Leu Lys Ser Trp Thr Val Glu Asp Leu Gln Lys Arg
1               5                   10                  15

Leu Leu Ala Leu Asp Pro Met Met Trp Gln Glu Ile Glu Glu Ile Arg
            20                  25                  30

Gln Lys Tyr Gln Ser Lys Arg Gln Pro Ile Leu Asp Ala Ile Glu Ala
        35                  40                  45

Lys

<210> SEQ ID NO 2
<211> LENGTH: 49
<212> TYPE: PRT
<213> ORGANISM: Homo sapiens

<400> SEQUENCE: 2

Asp Phe Asp Phe Leu Lys Asn Leu Ser Leu Glu Glu Leu Gln Met Arg
1               5                   10                  15

Leu Lys Ala Leu Asp Pro Met Met Glu Arg Glu Ile Glu Glu Leu Arg
            20                  25                  30

Gln Arg Tyr Thr Ala Gln Arg Gln Pro Ile Leu Asp Ala Met Asp Ala
        35                  40                  45

Lys

<210> SEQ ID NO 3
<211> LENGTH: 48
<212> TYPE: PRT
<213> ORGANISM: Drosophila

<400> SEQUENCE: 3

Phe Glu Phe Leu Lys Phe Leu Thr Phe Asp Asp Leu Asn Gln Arg Leu
1               5                   10                  15

Cys Asn Ile Asp His Glu Met Glu Leu Glu Ile Glu Gln Leu Asn Lys
            20                  25                  30

Lys Tyr Asn Ala Lys Arg Gln Pro Ile Val Asp Ala Met Asn Ala Lys
        35                  40                  45

<210> SEQ ID NO 4
<211> LENGTH: 47
<212> TYPE: PRT
<213> ORGANISM: Drosophila

<400> SEQUENCE: 4

Val Ala Gln Phe Leu Asn Leu Ser Leu Pro Glu Cys Arg Ala Ile Leu
1               5                   10                  15

Glu Arg Tyr Asp Glu Leu Ala Arg Glu Val Ala Lys Ile Lys Glu Arg
            20                  25                  30

Tyr Ala Glu Leu Arg Arg Arg Ile Val Ser Arg Met Glu Ser Leu
        35                  40                  45

<210> SEQ ID NO 5
<211> LENGTH: 48
<212> TYPE: PRT
<213> ORGANISM: Homo sapiens

<400> SEQUENCE: 5

Glu Val Glu Trp Asp Ala Phe Ser Ile Pro Leu Gln Asn Phe Leu
1               5                   10                  15
Thr Ile Leu Glu Lys Glu Glu Gln Asp Lys Ile Gln Gln Val Gln Lys
            20                  25                  30
Lys Tyr Asp Lys Phe Arg Gln Lys Leu Glu Glu Ala Leu Arg Glu Ser
        35                  40                  45

<210> SEQ ID NO 6
<211> LENGTH: 48
<212> TYPE: PRT
<213> ORGANISM: Homo sapiens

<400> SEQUENCE: 6

Glu Val Asn Trp Asp Ala Phe Ser Met Pro Glu Leu His Asn Phe Leu
1               5                   10                  15
Arg Ile Leu Gln Arg Glu Glu Glu His Leu Arg Gln Ile Leu Gln
            20                  25                  30
Lys Tyr Ser Tyr Cys Arg Gln Lys Ile Gln Glu Ala Leu His Ala Cys
        35                  40                  45

<210> SEQ ID NO 7
<211> LENGTH: 48
<212> TYPE: PRT
<213> ORGANISM: Homo sapiens

<400> SEQUENCE: 7

Ile Leu Lys Trp Glu Leu Phe Gln Leu Ala Asp Leu Asp Thr Tyr Gln
1               5                   10                  15
Gly Met Leu Lys Leu Leu Phe Met Lys Glu Leu Glu Gln Ile Val Lys
            20                  25                  30
Leu Tyr Glu Ala Tyr Arg Gln Ala Leu Leu Thr Glu Leu Glu Asn Arg
        35                  40                  45

<210> SEQ ID NO 8
<211> LENGTH: 48
<212> TYPE: PRT
<213> ORGANISM: Drosophila

<400> SEQUENCE: 8

Leu Leu Gln Phe Asn Met Phe Ser Leu Pro Glu Leu Gly Phe Asp
1               5                   10                  15
Ser Met Leu Val Arg Leu Phe Lys Gln Glu Leu Gly Thr Ile Val Gly
            20                  25                  30
Phe Tyr Glu Arg Tyr Arg Arg Ala Leu Ile Leu Glu Lys Asn Arg Arg
        35                  40                  45

<210> SEQ ID NO 9
<211> LENGTH: 49
<212> TYPE: PRT
<213> ORGANISM: Artificial Sequence
<220> FEATURE:
<223> OTHER INFORMATION: Synthetic Sequence Mutated Mst1 SARAH Domain

<400> SEQUENCE: 9

Asp Tyr Glu Phe Leu Lys Ser Trp Thr Val Glu Asp Leu Gln Lys Arg
1               5                   10                  15
Leu Leu Ala Leu Asp Pro Met Met Trp Gln Glu Ile Glu Glu Ile Arg
            20                  25                  30

```
Gln Lys Tyr Gln Cys Lys Arg Gln Pro Ile Leu Asp Ala Ile Glu Ala
            35                  40                  45

Lys

<210> SEQ ID NO 10
<211> LENGTH: 49
<212> TYPE: PRT
<213> ORGANISM: Artificial Sequence
<220> FEATURE:
<223> OTHER INFORMATION: Synthetic Sequence Mutated Mst2 SARAH Domain

<400> SEQUENCE: 10

Asp Phe Asp Phe Leu Lys Asn Leu Ser Leu Glu Glu Leu Gln Met Arg
1               5                   10                  15

Leu Lys Ala Leu Asp Pro Met Met Glu Arg Glu Ile Glu Glu Leu Arg
            20                  25                  30

Gln Arg Tyr Thr Cys Gln Arg Gln Pro Ile Leu Asp Ala Met Asp Ala
            35                  40                  45

Lys

<210> SEQ ID NO 11
<211> LENGTH: 48
<212> TYPE: PRT
<213> ORGANISM: Artificial Sequence
<220> FEATURE:
<223> OTHER INFORMATION: Synthetic Sequence Mutated Hippo SARAH Domain

<400> SEQUENCE: 11

Phe Glu Phe Leu Lys Phe Leu Thr Phe Asp Asp Leu Asn Gln Arg Leu
1               5                   10                  15

Cys Asn Ile Asp His Glu Met Glu Leu Glu Ile Glu Gln Leu Asn Lys
            20                  25                  30

Lys Tyr Asn Cys Lys Arg Gln Pro Ile Val Asp Ala Met Asn Ala Lys
            35                  40                  45

<210> SEQ ID NO 12
<211> LENGTH: 47
<212> TYPE: PRT
<213> ORGANISM: Artificial Sequence
<220> FEATURE:
<223> OTHER INFORMATION: Synthetic Sequence Mutated RASSF SARAH Domain

<400> SEQUENCE: 12

Val Ala Gln Phe Leu Asn Leu Ser Leu Pro Glu Cys Arg Ala Ile Leu
1               5                   10                  15

Glu Arg Tyr Asp Glu Leu Ala Arg Glu Val Ala Lys Ile Lys Glu Arg
            20                  25                  30

Tyr Ala Cys Leu Arg Arg Arg Ile Val Ser Arg Met Glu Ser Leu
            35                  40                  45

<210> SEQ ID NO 13
<211> LENGTH: 48
<212> TYPE: PRT
<213> ORGANISM: Artificial Sequence
<220> FEATURE:
<223> OTHER INFORMATION: Synthetic Sequence Mutated RASSF5 SARAH Domain

<400> SEQUENCE: 13

Glu Val Glu Trp Asp Ala Phe Ser Ile Pro Glu Leu Gln Asn Phe Leu
1               5                   10                  15

Thr Ile Leu Glu Lys Glu Glu Gln Asp Lys Ile Gln Gln Val Gln Lys
            20                  25                  30
```

```
Lys Tyr Asp Cys Phe Arg Gln Lys Leu Glu Glu Ala Leu Arg Glu Ser
        35                  40                  45
```

<210> SEQ ID NO 14
<211> LENGTH: 48
<212> TYPE: PRT
<213> ORGANISM: Artificial Sequence
<220> FEATURE:
<223> OTHER INFORMATION: Synthetic Sequence Mutated RASSF1 SARAH Domain

<400> SEQUENCE: 14

```
Glu Val Asn Trp Asp Ala Phe Ser Met Pro Glu Leu His Asn Phe Leu
1               5                   10                  15

Arg Ile Leu Gln Arg Glu Glu Glu His Leu Arg Gln Ile Leu Gln
            20                  25                  30

Lys Tyr Ser Cys Cys Arg Gln Lys Ile Gln Glu Ala Leu His Ala Cys
        35                  40                  45
```

<210> SEQ ID NO 15
<211> LENGTH: 48
<212> TYPE: PRT
<213> ORGANISM: Artificial Sequence
<220> FEATURE:
<223> OTHER INFORMATION: Synthetic Sequence Mutated WW45 SARAH Domain

<400> SEQUENCE: 15

```
Ile Leu Lys Trp Glu Leu Phe Gln Leu Ala Asp Leu Asp Thr Tyr Gln
1               5                   10                  15

Gly Met Leu Lys Leu Leu Phe Met Lys Glu Leu Glu Gln Ile Val Lys
            20                  25                  30

Leu Tyr Glu Cys Tyr Arg Gln Ala Leu Leu Thr Glu Leu Glu Asn Arg
        35                  40                  45
```

<210> SEQ ID NO 16
<211> LENGTH: 48
<212> TYPE: PRT
<213> ORGANISM: Artificial Sequence
<220> FEATURE:
<223> OTHER INFORMATION: Synthetic Sequence Mutated Sav SARAH Domain

<400> SEQUENCE: 16

```
Leu Leu Gln Phe Asn Met Phe Ser Leu Pro Glu Leu Glu Gly Phe Asp
1               5                   10                  15

Ser Met Leu Val Arg Leu Phe Lys Gln Glu Leu Gly Thr Ile Val Gly
            20                  25                  30

Phe Tyr Glu Cys Tyr Arg Arg Ala Leu Ile Leu Glu Lys Asn Arg Arg
        35                  40                  45
```

<210> SEQ ID NO 17
<211> LENGTH: 168
<212> TYPE: PRT
<213> ORGANISM: Artificial Sequence
<220> FEATURE:
<223> OTHER INFORMATION: Synthetic Sequence VH-SARAH(Y35C) of P20.1
      Antibody

<400> SEQUENCE: 17

```
Met Gln Ile Gln Leu Val Gln Ser Gly Pro Glu Val Gln Lys Pro Gly
1               5                   10                  15

Glu Thr Val Arg Ile Ser Cys Lys Ala Ser Gly Tyr Thr Phe Thr Thr
            20                  25                  30

Ala Gly Met Gln Trp Val Gln Lys Met Pro Gly Lys Ser Leu Lys Trp
```

```
                  35                  40                  45
Ile Gly Trp Ile Asn Thr Arg Ser Gly Val Pro Lys Tyr Ala Glu Asp
         50                  55                  60

Phe Lys Gly Arg Phe Ala Phe Ser Leu Glu Thr Ser Ala Ser Ile Ala
 65                  70                  75                  80

Tyr Leu His Ile Asn Asn Leu Lys Asn Glu Asp Thr Ala Thr Tyr Phe
                 85                  90                  95

Cys Ala Arg Glu Gly Pro Gly Phe Val Tyr Trp Gly Gln Gly Thr Leu
            100                 105                 110

Val Thr Val Ser Ser Gly Ser Asp Tyr Glu Phe Leu Lys Ser Trp Thr
        115                 120                 125

Val Glu Asp Leu Gln Lys Arg Leu Leu Ala Leu Asp Pro Met Met Glu
    130                 135                 140

Gln Glu Ile Glu Glu Ile Arg Gln Lys Cys Gln Ser Lys Arg Gln Pro
145                 150                 155                 160

Ile Leu Asp Ala Ile Glu Ala Lys
                165

<210> SEQ ID NO 18
<211> LENGTH: 163
<212> TYPE: PRT
<213> ORGANISM: Artificial Sequence
<220> FEATURE:
<223> OTHER INFORMATION: Synthetic Sequence VL-SARAH(M24C) of P20.1
      Antibody

<400> SEQUENCE: 18

Met Gly Gln Thr Val Val Thr Gln Glu Ser Ala Leu Thr Thr Ser Pro
  1               5                  10                  15

Gly Glu Thr Val Thr Leu Thr Cys Arg Ser Ser Thr Gly Ala Val Thr
             20                  25                  30

Thr Ser Asn Tyr Ala Asn Trp Val Gln Glu Lys Pro Asp His Leu Phe
         35                  40                  45

Thr Gly Leu Ile Val Gly Thr Asn Asn Arg Val Pro Gly Val Pro Pro
 50                  55                  60

Arg Phe Ser Gly Ser Leu Ile Glu Asp Lys Ala Ala Leu Thr Ile Thr
 65                  70                  75                  80

Gly Ala Gln Thr Glu Asp Glu Ala Ile Tyr Phe Cys Ala Leu Trp Tyr
                 85                  90                  95

Ser Asn His Trp Val Phe Gly Gly Gly Thr Lys Leu Thr Val Leu Gly
            100                 105                 110

Gly Ser Asp Tyr Glu Phe Leu Lys Ser Trp Thr Val Glu Asp Leu Gln
        115                 120                 125

Lys Arg Leu Leu Ala Leu Asp Pro Met Cys Glu Gln Glu Ile Glu Glu
    130                 135                 140

Ile Arg Gln Lys Tyr Gln Ser Lys Arg Gln Pro Ile Leu Asp Ala Ile
145                 150                 155                 160

Glu Ala Lys

<210> SEQ ID NO 19
<211> LENGTH: 507
<212> TYPE: DNA
<213> ORGANISM: Artificial Sequence
<220> FEATURE:
<223> OTHER INFORMATION: Synthetic Sequence VH-SARAH(Y35C) of P20.1
      Antibody

<400> SEQUENCE: 19
```

```
atgcagatcc agttggtgca gtctggacct gaggtgcaga agcctggaga gacagtcagg    60
atctcctgca aggcttctgg gtataccttc acaactgctg gaatgcagtg ggtgcaaaag   120
atgccaggaa agagtttgaa gtggattggc tggataaaca cccgctctgg agtgccaaaa   180
tatgcagaag acttcaaggg acgttttgcc ttctctttgg aaacctctgc cagtattgca   240
tatttacata taaacaacct caaaaatgag gacacggcta cctatttctg tgcgagagag   300
gggcctggat tgtttactg gggccaaggg actctggtca ccgtctcgag cggatccgac   360
tacgagtttc ttaagagttg gacagtggag gaccttcaga gaggctcttg gccctggac    420 cccatgatgg agcaggagat tgaagagatc cggcagaagt gccagtccaa gcggcagccc   480
atcctggatg ccatagaggc taagtag                                       507
```

<210> SEQ ID NO 20
<211> LENGTH: 510
<212> TYPE: DNA
<213> ORGANISM: Artificial Sequence
<220> FEATURE:
<223> OTHER INFORMATION: Synthetic Sequence VL-SARAH(M24C) of P20.1
    Antibody

<400> SEQUENCE: 20

```
atgggccaga tccagttggt gcagtctgga cctgaggtgc agaagcctgg agagacagtc    60
aggatctcct gcaaggcttc tgggtatacc ttcacaactg ctggaatgca gtgggtgcaa   120
aagatgccag gaaagagttt gaagtggatt ggctggataa acacccgctc tggagtgcca   180
aaatatgcag aagacttcaa gggacgtttt gccttctctt tggaaacctc tgccagtatt   240
gcatatttac atataaacaa cctcaaaaat gaggacacgg ctacctattt ctgtgcgaga   300
gaggggcctg gatttgttta ctggggccaa gggactctgg tcaccgtctc gagcggatcc   360
gactacgagt ttcttaagag ttggacagtg gaggaccttc agaagaggct cttggccctg   420 gacccccatga tggagcagga gattgaagag atccggcaga agtgccagtc caagcggcag   480
cccatcctgg atgccataga ggctaagtag                                    510
```

<210> SEQ ID NO 21
<211> LENGTH: 8
<212> TYPE: PRT
<213> ORGANISM: Artificial Sequence
<220> FEATURE:
<223> OTHER INFORMATION: Synthetic Sequence C8 Peptide

<400> SEQUENCE: 21

```
Pro Arg Gly Tyr Pro Gly Gln Val
1               5
```

<210> SEQ ID NO 22
<211> LENGTH: 196
<212> TYPE: PRT
<213> ORGANISM: Artificial Sequence
<220> FEATURE:
<223> OTHER INFORMATION: Synthetic Sequence VH-SARAH(Y35C) of P20.1
    Antibody

<400> SEQUENCE: 22

```
Met Leu Asp Ala Ser Gly Cys Ser Trp Met Trp Thr Trp Ala Leu Leu
1               5                   10                  15

Gln Leu Leu Leu Leu Val Gly Pro Gly Cys Gly Arg Gln Ile Gln
            20                  25                  30

Leu Val Gln Ser Gly Pro Glu Val Gln Lys Pro Gly Glu Thr Val Arg
```

```
                35                  40                  45
Ile Ser Cys Lys Ala Ser Gly Tyr Thr Phe Thr Thr Ala Gly Met Gln
     50                  55                  60
Trp Val Gln Lys Met Pro Gly Lys Ser Leu Lys Trp Ile Gly Trp Ile
65                  70                  75                  80
Asn Thr Arg Ser Gly Val Pro Lys Tyr Ala Glu Asp Phe Lys Gly Arg
                85                  90                  95
Phe Ala Phe Ser Leu Glu Thr Ser Ala Ser Ile Ala Tyr Leu His Ile
            100                 105                 110
Asn Asn Leu Lys Asn Glu Asp Thr Ala Thr Tyr Phe Cys Ala Arg Glu
        115                 120                 125
Gly Pro Gly Phe Val Tyr Trp Gly Gln Gly Thr Leu Val Thr Val Ser
    130                 135                 140
Ser Gly Ser Asp Tyr Glu Phe Leu Lys Ser Trp Thr Val Glu Asp Leu
145                 150                 155                 160
Gln Lys Arg Leu Leu Ala Leu Asp Pro Met Met Glu Gln Glu Ile Glu
                165                 170                 175
Glu Ile Arg Gln Lys Cys Gln Ser Lys Arg Gln Pro Ile Leu Asp Ala
            180                 185                 190
Ile Glu Ala Lys
        195

<210> SEQ ID NO 23
<211> LENGTH: 594
<212> TYPE: DNA
<213> ORGANISM: Artificial Sequence
<220> FEATURE:
<223> OTHER INFORMATION: Synthetic Sequence VH-SARAH(Y35C) of P20.1
      Antibody

<400> SEQUENCE: 23
atgctggacg cgagcggctg tagttgggcg atgtggacgt gggcgctgtt gcagctgctg      60
ctactagtgg ggcccggagg ctgcggccgc cagatccagt tggtgcagtc tggacctgag     120
gtgcagaagc ctggagagac agtcaggatc tcctgcaagg cttctgggta taccttcaca     180
actgctggaa tgcagtgggt gcaaaagatg ccaggaaaga gtttgaagtg gattggctgg     240
ataaacaccc gctctggagt gccaaaatat gcagaagact tcaagggacg ttttgccttc     300
tctttggaaa cctctgccag tattgcatat ttacatataa acaacctcaa aaatgaggac     360
acggctacct atttctgtgc gagagagggg cctggatttg tttactgggg ccaagggact     420
ctggtcaccg tctcgagcgg atccgactac gagtttctta agagttggac agtggaggac     480
cttcagaaga ggctcttggc cctggacccc atgatggagc aggagattga agagatccgg     540
cagaagtgcc agtccaagcg gcagcccatc ctggatgcca tagaggctaa gtaa           594

<210> SEQ ID NO 24
<211> LENGTH: 191
<212> TYPE: PRT
<213> ORGANISM: Artificial Sequence
<220> FEATURE:
<223> OTHER INFORMATION: Synthetic Sequence VL-SARAH(M24C) of P20.1
      Antibody

<400> SEQUENCE: 24

Met Leu Asp Ala Ser Gly Cys Ser Trp Met Trp Thr Trp Ala Leu Leu
1               5                   10                  15
Gln Leu Leu Leu Leu Val Gly Pro Gly Gly Cys Gly Arg Thr Gln Thr
            20                  25                  30
```

Val Val Thr Gln Glu Ser Ala Leu Thr Thr Ser Pro Gly Glu Thr Val
        35                  40                  45

Thr Leu Thr Cys Arg Ser Ser Thr Gly Ala Val Thr Thr Ser Asn Tyr
50                  55                  60

Ala Asn Trp Val Gln Glu Lys Pro Asp His Leu Phe Thr Gly Leu Ile
65                  70                  75                  80

Val Gly Thr Asn Asn Arg Val Pro Gly Val Pro Pro Arg Phe Ser Gly
                85                  90                  95

Ser Leu Ile Glu Asp Lys Ala Ala Leu Thr Ile Thr Gly Ala Gln Thr
            100                 105                 110

Glu Asp Glu Ala Ile Tyr Phe Cys Ala Leu Trp Tyr Ser Asn His Trp
        115                 120                 125

Val Phe Gly Gly Gly Thr Lys Leu Thr Val Leu Gly Gly Ser Asp Tyr
    130                 135                 140

Glu Phe Leu Lys Ser Trp Thr Val Glu Asp Leu Gln Lys Arg Leu Leu
145                 150                 155                 160

Ala Leu Asp Pro Met Cys Glu Gln Glu Ile Glu Ile Arg Gln Lys
                165                 170                 175

Tyr Gln Ser Lys Arg Gln Pro Ile Leu Asp Ala Ile Glu Ala Lys
            180                 185                 190

<210> SEQ ID NO 25
<211> LENGTH: 579
<212> TYPE: DNA
<213> ORGANISM: Artificial Sequence
<220> FEATURE:
<223> OTHER INFORMATION: Synthetic Sequence VL-SARAH(M24C) of P20.1
      Antibody

<400> SEQUENCE: 25
atgctggacg cgagcggctg tagttgggcg atgtggacgt gggcgctgtt gcagctgctg      60
ctactagtgg ggcccggagg ctgcggccgc acgcagactg ttgtgactca ggaatctgct     120
ctcaccacat cacctggtga acagtcaca ctcacttgtc gctcaagtac tggggctgtt      180
acaactagta actatgccaa ctgggtccaa gaaaaaccag atcatttatt cactggtcta     240
atagttggta ccaacaaccg agttccaggt gttcctccca gattctcagg ctccctgatt     300
gaagacaagg ctgccctcac catcacaggg gcacagactg aggatgaggc aatatatttc     360
tgtgctctat ggtacagcaa ccattgggtg ttcggtggag gaaccaaact gactgtccta     420
ggcggatccg actacgagtt tcttaagagt tggacagtgg aggaccttca gaagaggctc     480
ttggccctgg accccatgtg cgagcaggag attgaagaga tccggcagaa gtaccagtcc     540
aagcggcagc ccatcctgga tgccatagag gctaagtaa                            579

<210> SEQ ID NO 26
<211> LENGTH: 519
<212> TYPE: DNA
<213> ORGANISM: Artificial Sequence
<220> FEATURE:
<223> OTHER INFORMATION: Synthetic Sequence VH-SARAH(Y35C) of 12CA5
      Antibody

<400> SEQUENCE: 26
atggaagtga agttggttga atctggggga gacctggtga aaccgggcgg gagtctgaaa      60
ctgtcctgtg cggcaagtgg ctttaccttc tcatcctacg gcatgtcctg ggttcgtcag     120
accccggata agcgtctgga atgggtcgca actatttctc ggggcggtag ttatacctat     180

```
tacccccgatt cagtgaaagg ccggtttaca atcagccgcg acaacgctaa gaatactctg    240
tacctgcaga tgagctccct gaaatctgag gataccgcca tgtattactg cgcgcgccgt    300
gaaacctatg atgagaaagg tttcgcctac tgggggcagg gaaccacagt gaccgtttcc    360
tcaggatccg actacgagtt tcttaagagt tggacagtgg aggaccttca agagaggctc    420
ttggccctgg accccatgat ggagcaggag attgaagaga tccggcagaa gtgccagtcc    480
aagcggcagc ccatcctgga tgccatagag gctaagtag                           519
```

<210> SEQ ID NO 27
<211> LENGTH: 501
<212> TYPE: DNA
<213> ORGANISM: Artificial Sequence
<220> FEATURE:
<223> OTHER INFORMATION: Synthetic Sequence VL-SARAH(M24C) of 12CA5
      Antibody

<400> SEQUENCE: 27

```
atggacatcg aattgactca gtctccgtct agcctgaccg ttactgcggg agagaaagtt     60
acaatgagct gtaagtcttc ccagagcctg ctgaatagcg gcaaccagaa aaactatctg    120
acctggtacc agcagaaacc tggtcagccg cccaagctgc tgatctattg ggcatcaaca    180
cgcgaaagcg gcgtgcctga tcgttttacc ggctctggta gtgggcggga cttcaccctg    240
acaatcagct ccgtgcaggc cgaagatctg gcggtttatt actgccagaa cgacaattct    300 caccccgctga cttttggagc cggcaccaaa ctggagctga agcgggatc cgactacgag    360 tttcttaaga gttggacagt ggaggacctt cagaagaggc tcttggccct ggaccccatg    420
tgcgagcagg agattgaaga gatccggcag aagtaccagt ccaagcggca gcccatcctg    480
gatgccatag aggctaagta g                                              501
```

<210> SEQ ID NO 28
<211> LENGTH: 172
<212> TYPE: PRT
<213> ORGANISM: Artificial Sequence
<220> FEATURE:
<223> OTHER INFORMATION: Synthetic Sequence VH-SARAH(Y35C) of 12CA5
      Antibody

<400> SEQUENCE: 28

```
Met Glu Val Lys Leu Val Glu Ser Gly Gly Asp Leu Val Lys Pro Gly
1               5                   10                  15

Gly Ser Leu Lys Leu Ser Cys Ala Ala Ser Gly Phe Thr Phe Ser Ser
            20                  25                  30

Tyr Gly Met Ser Trp Val Arg Gln Thr Pro Asp Lys Arg Leu Glu Trp
        35                  40                  45

Val Ala Thr Ile Ser Arg Gly Gly Ser Tyr Thr Tyr Tyr Pro Asp Ser
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Met Tyr Tyr
                85                  90                  95

Cys Ala Arg Arg Glu Thr Tyr Asp Glu Lys Gly Phe Ala Tyr Trp Gly
            100                 105                 110

Gln Gly Thr Thr Val Thr Val Ser Ser Gly Ser Asp Tyr Glu Phe Leu
        115                 120                 125

Lys Ser Trp Thr Val Glu Asp Leu Gln Lys Arg Leu Leu Ala Leu Asp
    130                 135                 140
```

Pro Met Met Glu Gln Glu Ile Glu Glu Ile Arg Gln Lys Cys Gln Ser
145                 150                 155                 160

Lys Arg Gln Pro Ile Leu Asp Ala Ile Glu Ala Lys
            165                 170

<210> SEQ ID NO 29
<211> LENGTH: 166
<212> TYPE: PRT
<213> ORGANISM: Artificial Sequence
<220> FEATURE:
<223> OTHER INFORMATION: Synthetic Sequence VL-SARAH(M24C) of 12CA5
      Antibody

<400> SEQUENCE: 29

Met Asp Ile Glu Leu Thr Gln Ser Pro Ser Ser Leu Thr Val Thr Ala
1               5                   10                  15

Gly Glu Lys Val Thr Met Ser Cys Lys Ser Ser Gln Ser Leu Leu Asn
            20                  25                  30

Ser Gly Asn Gln Lys Asn Tyr Leu Thr Trp Tyr Gln Gln Lys Pro Gly
        35                  40                  45

Gln Pro Pro Lys Leu Leu Ile Tyr Trp Ala Ser Thr Arg Glu Ser Gly
    50                  55                  60

Val Pro Asp Arg Phe Thr Gly Ser Gly Ser Gly Arg Asp Phe Thr Leu
65                  70                  75                  80

Thr Ile Ser Ser Val Gln Ala Glu Asp Leu Ala Val Tyr Tyr Cys Gln
                85                  90                  95

Asn Asp Asn Ser His Pro Leu Thr Phe Gly Ala Gly Thr Lys Leu Glu
            100                 105                 110

Leu Lys Ala Gly Ser Asp Tyr Glu Phe Leu Lys Ser Trp Thr Val Glu
        115                 120                 125

Asp Leu Gln Lys Arg Leu Leu Ala Leu Asp Pro Met Cys Glu Gln Glu
    130                 135                 140

Ile Glu Glu Ile Arg Gln Lys Tyr Gln Ser Lys Arg Gln Pro Ile Leu
145                 150                 155                 160

Asp Ala Ile Glu Ala Lys
            165

<210> SEQ ID NO 30
<211> LENGTH: 9
<212> TYPE: PRT
<213> ORGANISM: Artificial Sequence
<220> FEATURE:
<223> OTHER INFORMATION: Synthetic Sequence HA peptide

<400> SEQUENCE: 30

Tyr Pro Tyr Asp Val Pro Asp Tyr Ala
1               5

<210> SEQ ID NO 31
<211> LENGTH: 193
<212> TYPE: PRT
<213> ORGANISM: Artificial Sequence
<220> FEATURE:
<223> OTHER INFORMATION: Synthetic Sequence VH-SARAH of 2H5 Antibody

<400> SEQUENCE: 31

Met Leu Val Leu Gln Trp Val Leu Val Thr Ala Leu Phe Gln Gly Val
1               5                   10                  15

His Cys Ala Val Gln Leu Val Glu Ser Gly Gly Gly Leu Val Gln Pro
            20                  25                  30

```
Lys Glu Ser Leu Lys Ile Ser Cys Ala Ala Phe Gly Val Thr Phe Ser
             35                  40                  45

Asn Val Ala Met Tyr Trp Val Arg Gln Ala Pro Gly Lys Gly Leu Glu
 50                  55                  60

Trp Ile Ala Arg Ile Arg Thr Lys Pro Asn Asn Tyr Ala Thr Tyr Tyr
 65                  70                  75                  80

Ala Asp Ser Val Lys Gly Arg Phe Thr Ile Ser Arg Asp Asp Ser Lys
                 85                  90                  95

Ser Met Val Tyr Leu Gln Met Asp Asn Leu Lys Thr Glu Asp Thr Ala
                100                 105                 110

Met Tyr Tyr Cys Thr Ala Glu Val Ala Thr Asp Trp Gly Gln Gly Val
                115                 120                 125

Met Val Thr Val Ser Ser Arg Ser Asp Tyr Glu Phe Leu Lys Ser Trp
130                 135                 140

Thr Val Glu Asp Leu Gln Lys Arg Leu Leu Ala Leu Asp Pro Met Met
145                 150                 155                 160

Glu Gln Glu Ile Glu Ile Arg Gln Lys Tyr Gln Ser Lys Arg Gln
                165                 170                 175

Pro Ile Leu Asp Ala Ile Glu Ala Lys Thr Gly His His His His
                180                 185                 190

His
```

<210> SEQ ID NO 32
<211> LENGTH: 192
<212> TYPE: PRT
<213> ORGANISM: Artificial Sequence
<220> FEATURE:
<223> OTHER INFORMATION: Synthetic Sequence VL-SARAH of 2H5 Antibody

<400> SEQUENCE: 32

```
Met Met Ser Pro Val Gln Ser Leu Phe Leu Leu Leu Trp Ile Leu
 1                   5                  10                  15

Gly Thr Asn Gly Asp Val Val Leu Thr Gln Ala Pro Pro Thr Leu Ser
                 20                  25                  30

Ala Thr Ile Gly Gln Ser Val Ser Ile Ser Cys Arg Ser Ser Gln Ser
             35                  40                  45

Leu Leu His Arg Asn Gly Asn Thr Tyr Leu Asn Trp Leu Leu Gln Arg
 50                  55                  60

Pro Gly Gln Pro Pro Gln Leu Leu Ile Tyr Leu Val Ser Arg Leu Glu
 65                  70                  75                  80

Ser Gly Val Pro Asn Arg Phe Ser Gly Ser Gly Ser Gly Thr Ala Phe
                 85                  90                  95

Thr Leu Lys Ile Ser Gly Leu Glu Ala Glu Asp Leu Gly Val Tyr Tyr
                100                 105                 110

Cys Val Gln Gly Thr His Ala Pro Leu Thr Phe Gly Ser Gly Thr Lys
            115                 120                 125

Leu Glu Ile Lys Arg Gly Ser Asp Tyr Glu Phe Leu Lys Ser Trp Thr
130                 135                 140

Val Glu Asp Leu Gln Lys Arg Leu Leu Ala Leu Asp Pro Met Met Glu
145                 150                 155                 160

Gln Glu Ile Glu Ile Arg Gln Lys Tyr Gln Ser Lys Arg Gln Pro
                165                 170                 175

Ile Leu Asp Ala Ile Glu Ala Lys Thr Gly His His His His His
                180                 185                 190
```

<210> SEQ ID NO 33
<211> LENGTH: 582
<212> TYPE: DNA
<213> ORGANISM: Artificial Sequence
<220> FEATURE:
<223> OTHER INFORMATION: Synthetic Sequence VH-SARAH of 2H5 Antibody

<400> SEQUENCE: 33

```
atgttggtgc tgcagtgggt tttggtgact gctcttttc aaggtgtgca ttgtgcggtg    60
cagcttgttg agtctggtgg aggattggtg cagcctaagg agtcattgaa aatctcatgt   120
gcagcctttg gagtcacctt cagtaatgtt gccatgtact gggtccgcca ggctccagga   180
aaggtctgg aatggattgc tcgcataaga actaaaccta taattatgc aacatattat    240
gctgattcag tgaaaggcag attcaccatc tccagagatg attcaaaaag catggtctac   300
ctacaaatgg ataacttgaa aactgaggac acagccatgt attactgtac agcagaagtt   360
gcaactgact ggggccaagg agtcatggtc acagtctcct caagatccga ctacgagttt   420
cttaagagtt ggacagtgga ggaccttcag aagaggctct tggccctgga ccccatgatg   480
gagcaggaga ttgaagagat ccggcagaag taccagtcca agcggcagcc atcctggat   540
gccatagagg ctaagaccgg tcatcatcac catcaccatt ga                     582
```

<210> SEQ ID NO 34
<211> LENGTH: 579
<212> TYPE: DNA
<213> ORGANISM: Artificial Sequence
<220> FEATURE:
<223> OTHER INFORMATION: Synthetic Sequence VL-SARAH of 2H5 Antibody

<400> SEQUENCE: 34

```
atgatgagtc ctgtccagtc cctgttttg ctattgcttt ggattctggg aaccaatggt    60
gatgttgtgc tgacccaggc tccacccact ttatcggcta ccattggaca atcagtctcc   120
atctcttgca ggtcaagtca gagtctctta catcgtaatg aaacaccta tttaaattgg   180
ttgctacaga ggccaggcca acctccacaa cttctaattt atttggtatc cagactggaa   240
tctggggtcc ccaacaggtt cagtggcagt gggtcaggaa ctgctttcac actcaaaatc   300
agtggactag aggctgagga tttgggagtt tattactgcg tgcaaggtac ccatgctccg   360
ctcacgttcg gttctgggac caagctggag atcaaacggg gatccgacta cgagtttctt   420
aagagttgga cagtggagga ccttcagaag aggctcttgg ccctggaccc catgatggag   480
caggagattg aagagatccg gcagaagtac cagtccaagc ggcagcccat cctggatgcc   540
atagaggcta agaccggtca tcatcaccat caccattga                        579
```

<210> SEQ ID NO 35
<211> LENGTH: 193
<212> TYPE: PRT
<213> ORGANISM: Artificial Sequence
<220> FEATURE:
<223> OTHER INFORMATION: Synthetic Sequence VH(11C)-SARAH of 2H5
       Antibody

<400> SEQUENCE: 35

```
Met Leu Val Leu Gln Trp Val Leu Val Thr Ala Leu Phe Gln Gly Val
1               5                   10                  15

His Cys Ala Val Gln Leu Val Glu Ser Gly Gly Gly Cys Val Gln Pro
            20                  25                  30

Lys Glu Ser Leu Lys Ile Ser Cys Ala Ala Phe Gly Val Thr Phe Ser
        35                  40                  45
```

```
Asn Val Ala Met Tyr Trp Val Arg Gln Ala Pro Gly Lys Gly Leu Glu
    50                  55                  60

Trp Ile Ala Arg Ile Arg Thr Lys Pro Asn Asn Tyr Ala Thr Tyr Tyr
65                  70                  75                  80

Ala Asp Ser Val Lys Gly Arg Phe Thr Ile Ser Arg Asp Asp Ser Lys
                85                  90                  95

Ser Met Val Tyr Leu Gln Met Asp Asn Leu Lys Thr Glu Asp Thr Ala
            100                 105                 110

Met Tyr Tyr Cys Thr Ala Glu Val Ala Thr Asp Trp Gly Gln Gly Val
        115                 120                 125

Met Val Thr Val Ser Ser Arg Ser Asp Tyr Glu Phe Leu Lys Ser Trp
    130                 135                 140

Thr Val Glu Asp Leu Gln Lys Arg Leu Leu Ala Leu Asp Pro Met Met
145                 150                 155                 160

Glu Gln Glu Ile Glu Glu Ile Arg Gln Lys Tyr Gln Ser Lys Arg Gln
                165                 170                 175

Pro Ile Leu Asp Ala Ile Glu Ala Lys Thr Gly His His His His His
            180                 185                 190

His

<210> SEQ ID NO 36
<211> LENGTH: 192
<212> TYPE: PRT
<213> ORGANISM: Artificial Sequence
<220> FEATURE:
<223> OTHER INFORMATION: Synthetic Sequence VL-SARAH(33C) of 2H5
      Antibody

<400> SEQUENCE: 36

Met Met Ser Pro Val Gln Ser Leu Phe Leu Leu Leu Trp Ile Leu
1               5                   10                  15

Gly Thr Asn Gly Asp Val Val Leu Thr Gln Ala Pro Pro Thr Leu Ser
            20                  25                  30

Ala Thr Ile Gly Gln Ser Val Ser Ile Ser Cys Arg Ser Ser Gln Ser
        35                  40                  45

Leu Leu His Arg Asn Gly Asn Thr Tyr Leu Asn Trp Leu Leu Gln Arg
    50                  55                  60

Pro Gly Gln Pro Pro Gln Leu Leu Ile Tyr Leu Val Ser Arg Leu Glu
65                  70                  75                  80

Ser Gly Val Pro Asn Arg Phe Ser Gly Ser Gly Ser Gly Thr Ala Phe
                85                  90                  95

Thr Leu Lys Ile Ser Gly Leu Glu Ala Glu Asp Leu Gly Val Tyr Tyr
            100                 105                 110

Cys Val Gln Gly Thr His Ala Pro Leu Thr Phe Gly Ser Gly Thr Lys
        115                 120                 125

Leu Glu Ile Lys Arg Gly Ser Asp Tyr Glu Phe Leu Lys Ser Trp Thr
    130                 135                 140

Val Glu Asp Leu Gln Lys Arg Leu Leu Ala Leu Asp Pro Met Met Glu
145                 150                 155                 160

Gln Glu Ile Glu Cys Ile Arg Gln Lys Tyr Gln Ser Lys Arg Gln Pro
                165                 170                 175

Ile Leu Asp Ala Ile Glu Ala Lys Thr Gly His His His His His His
            180                 185                 190

<210> SEQ ID NO 37
<211> LENGTH: 193
```

```
<212> TYPE: PRT
<213> ORGANISM: Artificial Sequence
<220> FEATURE:
<223> OTHER INFORMATION: Synthetic Sequence VH(108C)-SARAH of 2H5
      Antibody

<400> SEQUENCE: 37
```

Met Leu Val Leu Gln Trp Val Leu Val Thr Ala Leu Phe Gln Gly Val
1               5                   10                  15

His Cys Ala Val Gln Leu Val Glu Ser Gly Gly Gly Leu Val Gln Pro
                20                  25                  30

Lys Glu Ser Leu Lys Ile Ser Cys Ala Ala Phe Gly Val Thr Phe Ser
                35                  40                  45

Asn Val Ala Met Tyr Trp Val Arg Gln Ala Pro Gly Lys Gly Leu Glu
            50                  55                  60

Trp Ile Ala Arg Ile Arg Thr Lys Pro Asn Asn Tyr Ala Thr Tyr Tyr
65                  70                  75                  80

Ala Asp Ser Val Lys Gly Arg Phe Thr Ile Ser Arg Asp Asp Ser Lys
                85                  90                  95

Ser Met Val Tyr Leu Gln Met Asp Asn Leu Lys Thr Glu Asp Thr Ala
                100                 105                 110

Met Tyr Tyr Cys Thr Ala Glu Val Ala Thr Asp Trp Gly Gln Gly Val
            115                 120                 125

Cys Val Thr Val Ser Ser Arg Ser Asp Tyr Glu Phe Leu Lys Ser Trp
130                 135                 140

Thr Val Glu Asp Leu Gln Lys Arg Leu Leu Ala Leu Asp Pro Met Met
145                 150                 155                 160

Glu Gln Glu Ile Glu Glu Ile Arg Gln Lys Tyr Gln Ser Lys Arg Gln
                165                 170                 175

Pro Ile Leu Asp Ala Ile Glu Ala Lys Thr Gly His His His His
                180                 185                 190

His

```
<210> SEQ ID NO 38
<211> LENGTH: 192
<212> TYPE: PRT
<213> ORGANISM: Artificial Sequence
<220> FEATURE:
<223> OTHER INFORMATION: Synthetic Sequence VL-SARAH(30C) of 2H5
      Antibody

<400> SEQUENCE: 38
```

Met Met Ser Pro Val Gln Ser Leu Phe Leu Leu Leu Trp Ile Leu
1               5                   10                  15

Gly Thr Asn Gly Asp Val Val Leu Thr Gln Ala Pro Pro Thr Leu Ser
                20                  25                  30

Ala Thr Ile Gly Gln Ser Val Ser Ile Ser Cys Arg Ser Ser Gln Ser
            35                  40                  45

Leu Leu His Arg Asn Gly Asn Thr Tyr Leu Asn Trp Leu Leu Gln Arg
        50                  55                  60

Pro Gly Gln Pro Pro Gln Leu Leu Ile Tyr Leu Val Ser Arg Leu Glu
65                  70                  75                  80

Ser Gly Val Pro Asn Arg Phe Ser Gly Ser Gly Ser Gly Thr Ala Phe
                85                  90                  95

Thr Leu Lys Ile Ser Gly Leu Glu Ala Glu Asp Leu Gly Val Tyr Tyr
                100                 105                 110

Cys Val Gln Gly Thr His Ala Pro Leu Thr Phe Gly Ser Gly Thr Lys

```
                115                 120                 125
Leu Glu Ile Lys Arg Gly Ser Asp Tyr Glu Phe Leu Lys Ser Trp Thr
    130                 135                 140

Val Glu Asp Leu Gln Lys Arg Leu Leu Ala Leu Asp Pro Met Met Glu
145                 150                 155                 160

Gln Glu Ile Glu Ile Arg Cys Lys Tyr Gln Ser Lys Arg Gln Pro
                165                 170                 175

Ile Leu Asp Ala Ile Glu Ala Lys Thr Gly His His His His His
        180                 185                 190

<210> SEQ ID NO 39
<211> LENGTH: 193
<212> TYPE: PRT
<213> ORGANISM: Artificial Sequence
<220> FEATURE:
<223> OTHER INFORMATION: Synthetic Sequence VH(112C)-SARAH of 2H5
      Antibody

<400> SEQUENCE: 39

Met Leu Val Leu Gln Trp Val Leu Val Thr Ala Leu Phe Gln Gly Val
1               5                   10                  15

His Cys Ala Val Gln Leu Val Glu Ser Gly Gly Gly Leu Val Gln Pro
            20                  25                  30

Lys Glu Ser Leu Lys Ile Ser Cys Ala Ala Phe Gly Val Thr Phe Ser
        35                  40                  45

Asn Val Ala Met Tyr Trp Val Arg Gln Ala Pro Gly Lys Gly Leu Glu
    50                  55                  60

Trp Ile Ala Arg Ile Arg Thr Lys Pro Asn Asn Tyr Ala Thr Tyr Tyr
65                  70                  75                  80

Ala Asp Ser Val Lys Gly Arg Phe Thr Ile Ser Arg Asp Asp Ser Lys
                85                  90                  95

Ser Met Val Tyr Leu Gln Met Asp Asn Leu Lys Thr Glu Asp Thr Ala
            100                 105                 110

Met Tyr Tyr Cys Thr Ala Glu Val Ala Thr Asp Trp Gly Gln Gly Val
        115                 120                 125

Met Val Thr Val Cys Ser Arg Ser Asp Tyr Glu Phe Leu Lys Ser Trp
    130                 135                 140

Thr Val Glu Asp Leu Gln Lys Arg Leu Leu Ala Leu Asp Pro Met Met
145                 150                 155                 160

Glu Gln Glu Ile Glu Glu Ile Arg Gln Lys Tyr Gln Ser Lys Arg Gln
                165                 170                 175

Pro Ile Leu Asp Ala Ile Glu Ala Lys Thr Gly His His His His
            180                 185                 190

His

<210> SEQ ID NO 40
<211> LENGTH: 192
<212> TYPE: PRT
<213> ORGANISM: Artificial Sequence
<220> FEATURE:
<223> OTHER INFORMATION: Synthetic Sequence VL-SARAH(37C) of 2H5
      Antibody

<400> SEQUENCE: 40

Met Met Ser Pro Val Gln Ser Leu Phe Leu Leu Leu Trp Ile Leu
1               5                   10                  15

Gly Thr Asn Gly Asp Val Val Leu Thr Gln Ala Pro Pro Thr Leu Ser
            20                  25                  30
```

-continued

```
Ala Thr Ile Gly Gln Ser Val Ser Ile Ser Cys Arg Ser Gln Ser
        35                  40                  45

Leu Leu His Arg Asn Gly Asn Thr Tyr Leu Asn Trp Leu Leu Gln Arg
    50                  55                  60

Pro Gly Gln Pro Pro Gln Leu Leu Ile Tyr Leu Val Ser Arg Leu Glu
65                  70                  75                  80

Ser Gly Val Pro Asn Arg Phe Ser Gly Ser Gly Ser Gly Thr Ala Phe
                85                  90                  95

Thr Leu Lys Ile Ser Gly Leu Glu Ala Glu Asp Leu Gly Val Tyr Tyr
            100                 105                 110

Cys Val Gln Gly Thr His Ala Pro Leu Thr Phe Gly Gly Thr Lys
            115                 120                 125

Leu Glu Ile Lys Arg Gly Ser Asp Tyr Glu Phe Leu Lys Ser Trp Thr
            130                 135                 140

Val Glu Asp Leu Gln Lys Arg Leu Leu Ala Leu Asp Pro Met Met Glu
145                 150                 155                 160

Gln Glu Ile Glu Glu Ile Arg Gln Lys Tyr Gln Cys Lys Arg Gln Pro
                165                 170                 175

Ile Leu Asp Ala Ile Glu Ala Lys Thr Gly His His His His His
            180                 185                 190
```

<210> SEQ ID NO 41
<211> LENGTH: 507
<212> TYPE: DNA
<213> ORGANISM: Artificial Sequence
<220> FEATURE:
<223> OTHER INFORMATION: Synthetic Sequence VH(112C)-SARAH of P20.1
      Antibody

<400> SEQUENCE: 41

```
atgcagatcc agttggtgca gtctggacct gaggtgcaga agcctggaga cagtcagg      60 atctcctgca aggcttctgg gtataccttc acaactgctg gaatgcagtg ggtgcaaaag   120
atgccaggaa agagtttgaa gtggattggc tggataaaca cccgctctgg agtgccaaaa   180
tatgcagaag acttcaaggg acgttttgcc ttctcttttgg aaacctctgc cagtattgca   240
tatttacata taaacaacct caaaaatgag gacacggcta cctatttctg tgcgagagag   300
gggcctggat tgttttactg gggccaaggg actctggtca ccgtctgcag cggatccgac   360
tacgagtttc ttaagagttg gacagtggag gaccttcaga gaggctctt ggccctggac    420 cccatgatgg agcaggagat tgaagagatc cggcagaagt accagtccaa gcggcagccc   480
atcctggatg ccatagaggc taagtag                                        507
```

<210> SEQ ID NO 42
<211> LENGTH: 510
<212> TYPE: DNA
<213> ORGANISM: Artificial Sequence
<220> FEATURE:
<223> OTHER INFORMATION: Synthetic Sequence VL-SARAH(37C) of P20.1
      Antibody

<400> SEQUENCE: 42

```
atgggccaga tccagttggt gcagtctgga cctgaggtgc agaagcctgg agagacagtc    60
aggatctcct gcaaggcttc tgggtatacc ttcacaactg ctggaatgca gtgggtgcaa   120
aagatgccag aaagagtttg aagtggattg gctggataaa cacccgctct ggagtgccaa   180
aaatatgcag aagacttcaa gggacgtttt gccttctctt tggaaacctc tgccagtatt   240
```

```
gcatatttac atataaacaa cctcaaaaat gaggacacgg ctacctattt ctgtgcgaga    300
gaggggcctg gatttgttta ctggggccaa gggactctgg tcaccgtctc gagcggatcc    360
gactacgagt ttcttaagag ttggacagtg gaggaccttc agaagaggct cttggccctg    420
gaccccatga tggagcagga gattgaagag atccggcaga agtaccagtg caagcggcag    480
cccatcctgg atgccataga ggctaagtag                                     510
```

```
<210> SEQ ID NO 43
<211> LENGTH: 168
<212> TYPE: PRT
<213> ORGANISM: Artificial Sequence
<220> FEATURE:
<223> OTHER INFORMATION: Synthetic Sequence VH(112C)-SARAH of P20.1
      Antibody

<400> SEQUENCE: 43
```

Met Gln Ile Gln Leu Val Gln Ser Gly Pro Glu Val Gln Lys Pro Gly
1               5                   10                  15

Glu Thr Val Arg Ile Ser Cys Lys Ala Ser Gly Tyr Thr Phe Thr Thr
                20                  25                  30

Ala Gly Met Gln Trp Val Gln Lys Met Pro Gly Lys Ser Leu Lys Trp
            35                  40                  45

Ile Gly Trp Ile Asn Thr Arg Ser Gly Val Pro Lys Tyr Ala Glu Asp
50                  55                  60

Phe Lys Gly Arg Phe Ala Phe Ser Leu Glu Thr Ser Ala Ser Ile Ala
65                  70                  75                  80

Tyr Leu His Ile Asn Asn Leu Lys Asn Glu Asp Thr Ala Thr Tyr Phe
                85                  90                  95

Cys Ala Arg Glu Gly Pro Gly Phe Val Tyr Trp Gly Gln Gly Thr Leu
            100                 105                 110

Val Thr Val Cys Ser Gly Ser Asp Tyr Glu Phe Leu Lys Ser Trp Thr
        115                 120                 125

Val Glu Asp Leu Gln Lys Arg Leu Leu Ala Leu Asp Pro Met Met Glu
    130                 135                 140

Gln Glu Ile Glu Glu Ile Arg Gln Lys Tyr Gln Ser Lys Arg Gln Pro
145                 150                 155                 160

Ile Leu Asp Ala Ile Glu Ala Lys
                165

```
<210> SEQ ID NO 44
<211> LENGTH: 163
<212> TYPE: PRT
<213> ORGANISM: Artificial Sequence
<220> FEATURE:
<223> OTHER INFORMATION: Synthetic Sequence VL-SARAH(37C) of P20.1
      Antibody

<400> SEQUENCE: 44
```

Met Gly Gln Thr Val Val Thr Gln Glu Ser Ala Leu Thr Thr Ser Pro
1               5                   10                  15

Gly Glu Thr Val Thr Leu Thr Cys Arg Ser Ser Thr Gly Ala Val Thr
                20                  25                  30

Thr Ser Asn Tyr Ala Asn Trp Val Gln Glu Lys Pro Asp His Leu Phe
            35                  40                  45

Thr Gly Leu Ile Val Gly Thr Asn Asn Arg Val Pro Gly Val Pro Pro
50                  55                  60

Arg Phe Ser Gly Ser Leu Ile Glu Asp Lys Ala Ala Leu Thr Ile Thr
65                  70                  75                  80

Gly Ala Gln Thr Glu Asp Glu Ala Ile Tyr Phe Cys Ala Leu Trp Tyr
            85                  90                  95

Ser Asn His Trp Val Phe Gly Gly Thr Lys Leu Thr Val Leu Gly
            100                 105                 110

Gly Ser Asp Tyr Glu Phe Leu Lys Ser Trp Thr Val Glu Asp Leu Gln
            115                 120                 125

Lys Arg Leu Leu Ala Leu Asp Pro Met Met Glu Gln Glu Ile Glu Glu
            130                 135                 140

Ile Arg Gln Lys Tyr Gln Cys Lys Arg Gln Pro Ile Leu Asp Ala Ile
145                 150                 155                 160

Glu Ala Lys

<210> SEQ ID NO 45
<211> LENGTH: 519
<212> TYPE: DNA
<213> ORGANISM: Artificial Sequence
<220> FEATURE:
<223> OTHER INFORMATION: Synthetic Sequence VH(112C)-SARAH of 93201
      Antibody

<400> SEQUENCE: 45
atggaggttc agctgcagca gtctggggca gagcttgtga agccaggggc ctcagtcaag      60
ttgtcctgca cagcttctgg cttcaacatt aagacacct atattcactg ggtgaagcag     120
aggcctgaac agggcctgga ctggattgga aggattgatc ctgcgaatgg taatactaaa    180
tatgacccga acttccaggg caaggccact ataacagcag acacatcctc aacacagcc     240 tacctgcagc tcagcagcct ggcatctgag gacactgccg tctattactg tgctacctcc    300
aattactaca gtaggggtgc tatggactat tggggtcaag aacctcagt caccgtctgc    360 agcggatccg actacgagtt tcttaagagt tggacagtgg aggacccttca gaagaggctc    420 ttggccctgg accccatgat ggagcaggag attgaagaga tccggcagaa gtaccagtcc    480
aagcggcagc ccatcctgga tgccatagag gctaagtaa                           519

<210> SEQ ID NO 46
<211> LENGTH: 519
<212> TYPE: DNA
<213> ORGANISM: Artificial Sequence
<220> FEATURE:
<223> OTHER INFORMATION: Synthetic Sequence VH(112C)-SARAH of TS2/16
      Antibody

<400> SEQUENCE: 46
atggacgtga agttggtgga gtctggggga ggcttagtga agcctggagg gtccctgaaa      60
ctctcctgtg cagcctctgg attcactttc agtagctata ccatgtcttg ggttcgccag     120
actccggaga gaggctgga gtgggtcgca accataagta gtggtggttc ttacacctac     180
tatccagaca gtgtgaaggg ccgattcacc atttccagag acaaagccaa gaacaccctg     240
tatttgcaaa tgggcagtct gaagtctgag gacacagcca tgtattactg tacaagaata     300
ggttacgacg aagattatgc tatggaccac tggggtcaag aacctcagt caccgtctgc     360 tcaggatctg actacgagtt tcttaagagt tggacagtgg aggacccttca gaagaggctc    420 ttggccctgg accccatgat ggagcaggag attgaagaga tccggcagaa gtaccagtcc    480
aagcggcagc ccatcctgga tgccatagag gctaagtag                           519

<210> SEQ ID NO 47
<211> LENGTH: 513

```
<212> TYPE: DNA
<213> ORGANISM: Artificial Sequence
<220> FEATURE:
<223> OTHER INFORMATION: Synthetic Sequence VH(112C)-SARAH of SG/19
      Antibody

<400> SEQUENCE: 47
atgcaggttc acctgcagca gtctggagct gagctgatga agcctggggc ctcagtgaag      60
atatcctgca aggctactgg ctacacattc actagctact ggatagagtg ggtaaagcag     120
aggcctggac atggccttga gtggcttgga gagatttttac ctggaagtgg ttatattcat    180
tataatgaga agtttaaggg caaggccaca ttcactacag atacatcctc aaacacagcc     240
tacatgcaac tcagcagcct gacatctgag gactctgccg tctattactg ttcaagggct     300
ctggccctct atgctatgga ctattggggt caaggaacct cagtcaccgt ctgctcagga     360
tctgactacg agtttcttaa gagttggaca gtggaggacc ttcagaagag gctcttggcc     420 ctggaccca tgatggagca ggagattgaa gagatccggc agaagtacca gtccaagcgg     480
cagcccatcc tggatgccat agaggctaag tag                                  513

<210> SEQ ID NO 48
<211> LENGTH: 525
<212> TYPE: DNA
<213> ORGANISM: Artificial Sequence
<220> FEATURE:
<223> OTHER INFORMATION: Synthetic Sequence VH(112C)-SARAH of t8E4
      Antibody

<400> SEQUENCE: 48
atgaaacagg tgcagctgaa ggagtcagga cctgaccttg tgcagccctc acagaccctg      60
tctctcacct gcactgtctc tgggttctca ttaaccggct atggtgttca ctgggttcgc     120
cagcctccag gaagggact ggagtgggtg ggaacactgg gctggaatga caaaaaatat     180
tataattcag ctctaaaatc tcgactgagc atcagcaggg atacctccaa gaaccaagtt     240
ttcttaaaac tgagcagtct ggaaactgaa gacacagcca tgtactactg tactagagat     300
ggcggcctac tattcgctta ctatgctatg gactactggg gtcaaggaac ctcagtcacc     360
gtctgcagcg atccgactac gagtttctt aagagttgga cagtggagga ccttcagaag     420
aggctcttgg ccctggaccc catgatggag caggagattg aagagatccg cagaagtac    480 cagtccaagc ggcagcccat cctggatgcc atagaggcta agtaa                    525

<210> SEQ ID NO 49
<211> LENGTH: 540
<212> TYPE: DNA
<213> ORGANISM: Artificial Sequence
<220> FEATURE:
<223> OTHER INFORMATION: Synthetic Sequence VH(112C)-SARAH of 9E10
      Antibody

<400> SEQUENCE: 49
atggaagtga agttggttga atctggggga gatctggtca aaccggggagg gagcctgaaa     60 ctgtcatgtg cggcgtctgg ctttaccttt tctcattacg gatgtcctg ggtgcggcag     120 actccggata gcgtctggaa tgggtcgcc accattgggt cccggggaac ctatacacac     180 tacccgact ctgtgaaagg ccggtttacc atcagtcgcg ataacgacaa gaatgcactg     240
tatctgcaga tgaacagcct gaaatccgaa gatacagcca tgtattactg cgcgcgccgt     300
agtgagttct actactacgg taacacatac tactactcag caatggacta ctggggccag     360
ggtgctagcg tgactgtttg cagcggatcc gactacgagt ttcttaagag ttggacagtg     420
```

```
gaggaccttc agaagaggct cttggccctg acccccatga tggagcagga gattgaagag    480
atccggcaga agtaccagtc aagcggcag cccatcctgg atgccataga ggctaagtaa    540

<210> SEQ ID NO 50
<211> LENGTH: 519
<212> TYPE: DNA
<213> ORGANISM: Artificial Sequence
<220> FEATURE:
<223> OTHER INFORMATION: Synthetic Sequence VH(112C)-SARAH of 12CA5
      Antibody

<400> SEQUENCE: 50
atggaagtga agttggttga atctggggga gacctggtga accgggcgg gagtctgaaa      60 ctgtcctgtg cggcaagtgg ctttaccttc tcatcctacg gcatgtcctg ggttcgtcag    120
accccggata gcgtctggga tgggtcgca actatttctc ggggcggtag ttatacctat    180
taccccgatt cagtgaaagg ccggtttaca atcagccgcg acaacgctaa gaatactctg    240
tacctgcaga tgagctccct gaaatctgag gataccgcca tgtattactg cgcgcgccgt    300
gaaacctatg atgagaaagg tttcgcctac tgggggcagg gaaccacagt gaccgtttgc    360
agcggatccg actacgagtt tcttaagagt tggacagtgg aggaccttca agaggctc      420 ttggccctgg accccatgat ggagcaggag attgaagaga tccggcagaa gtaccagtcc    480
aagcggcagc ccatcctgga tgccatagag gctaagtaa                           519

<210> SEQ ID NO 51
<211> LENGTH: 522
<212> TYPE: DNA
<213> ORGANISM: Artificial Sequence
<220> FEATURE:
<223> OTHER INFORMATION: Synthetic Sequence VH(112C)-SARAH of t1E4
      Antibody

<400> SEQUENCE: 51
atgaaacagg gtcagctgca gcagtctgga cctgagctgg tgaagcctgg ggcctcagtg     60
aagatttcct gcaaggcttc tggctatgtc ttcagtagct cctggatgaa ctgggtgaag    120
cagaggcctg gaaagggtct tgagtggatt ggacggattt atcctggata tggagatact    180
aactacaatg gaagttcaa gggcaaggcc acactgactg cagacaaatc ctccagcaca    240
gcctacatgc aactcagcag cctgacatct gaggactctg cggtctactt ctgtgtaaga    300
gaggaactgg accctactg gtacttcgat gtctggggcg cagggaccac ggtcaccgtc    360
tgcagcggat ccgactacga gtttcttaag agttggacag tggaggacct tcagaagagg    420
ctcttggccc tggaccccat gatggagcag gagattgaag agatccggca agtaccag     480 tccaagcggc agcccatcct ggatgccata gaggctaagt aa                       522

<210> SEQ ID NO 52
<211> LENGTH: 513
<212> TYPE: DNA
<213> ORGANISM: Artificial Sequence
<220> FEATURE:
<223> OTHER INFORMATION: Synthetic Sequence VH(112C)-SARAH of NZ-1
      Antibody

<400> SEQUENCE: 52
atgaaagagg tgcagctggt ggagtctggg ggaggcttag tgcagcctgg aaggtccctg     60
aaactctcct gtgcagcctc aggattcact ttcagtaact atggcatggc ctgggtccgc    120
cagactccaa cgaagggtct ggagtggatc gcatccatta gtgctggtgg tgataaaact    180
```

```
tactatggag actccgtgaa gggccgattc agtatctcca gagataatgc aaaaaccacc    240
cactacttgc aaatggacag tctgaggtct gaggacacgg ccacttatta ctgtgcaaaa    300
acttcccggg tatattttga ttactggggc caaggagtca tggtcacagt ctgcagcgga    360
tccgactacg agtttcttaa gagttggaca gtggaggacc ttcagaagag gctcttggcc    420
ctggacccca tgatggagca ggagattgaa gagatccggc agaagtacca gtccaagcgg    480
cagcccatcc tggatgccat agaggctaag taa                                 513

<210> SEQ ID NO 53
<211> LENGTH: 494
<212> TYPE: DNA
<213> ORGANISM: Artificial Sequence
<220> FEATURE:
<223> OTHER INFORMATION: Synthetic Sequence VL-SARAH(37C) of 93201
      Antibody

<400> SEQUENCE: 53
atggacattg tgctcaccca atctccagct tctttggctg tgtctctagg gcagagagcc     60
accatctcct gcagagccag tgaaagtgtt gaatattatg cacaaattt aatgcactgg    120 taccaacaga aaccaggaca gccacccaaa ctcctcatct atgttgcatc caccgtaaaa    180
tctggggtcc ctgccaggtt tagtggcagt gggtctggga cagacttcag cctcaacatc    240
catcctgtgg aggaggatga tattgcaatg tatttctgtc agcaaagtag gaaggttccg    300
tggacgttcg gtggaggcac cagactggaa atcaaacggg atccgactac gagtttctt     360 aagagttgga cagtggagga ccttcagaag aggctcttgg ccctggaccc catgatggag    420
caggagattg aagagatccg gcagaagtac cagtgcaagc ggcagcccat cctggatgcc    480
atagaggcta agta                                                      494

<210> SEQ ID NO 54
<211> LENGTH: 486
<212> TYPE: DNA
<213> ORGANISM: Artificial Sequence
<220> FEATURE:
<223> OTHER INFORMATION: Synthetic Sequence VL-SARAH(37C) of TS2/16
      Antibody

<400> SEQUENCE: 54
atgcagattg ttgttacgca gagaccgaca accatggctg catctcccgg ggacaagatc     60
attatcacct gcagtgtcag ttcaattata agttccaatt acctgcattg gtatagtcag    120
aagccaggat tctcccctaa actcttgatt tataggacat ccaatctggc ttctggagtc    180
ccacctcgct tcagtggcag tgggtctggg acctcttact ctctcacaat tggcaccatg    240
gaggctgaag atgttgccac ttactactgc cagcagggtt ctgatattcc actcacgttc    300
ggtgatggga ccaagctgga cctgaaacgg gatctgact acgagtttct taagagttgg    360
acagtggagg accttcagaa gaggctcttg gccctggacc ccatgatgga gcaggagatt    420
gaagagatcc ggcagaagta ccagtgcaag cggcagccca tcctggatgc catagaggct    480
aagtag                                                               486

<210> SEQ ID NO 55
<211> LENGTH: 498
<212> TYPE: DNA
<213> ORGANISM: Artificial Sequence
<220> FEATURE:
<223> OTHER INFORMATION: Synthetic Sequence VL-SARAH(37C) of SG/19
      Antibody
```

<400> SEQUENCE: 55

```
atggacatcg ttatgactca ggctaccccc tctatacctg tcactcctgg agagtcagtc      60
tccatctcct gcaggtctaa taagagtctc ctgcatagta atggcaacac ttacttgtat     120
tggttcctgc agaggccagg ccagtctcct cggctcctga tatttcggat gtccaacctt     180
gcctcaggag tcccagacag gttcagtggc agtgggtcag gaactgcttt cacactgaga     240
atcagtagag tggaggctgc ggatgtgggt atttatttct gtttgcaaca tctagaatat     300
cctttcacgt tcggtgctgg gaccaagctg gagctgaagc ggggatctga ctacgagttt     360
cttaagagtt ggacagtgga ggaccttcag aagaggctct ggccctggac ccccatgatg     420
gagcaggaga ttgaagagat ccggcagaag taccagtgca agcggcagcc catcctggat     480
gccatagagg ctaagtag                                                   498
```

<210> SEQ ID NO 56
<211> LENGTH: 483
<212> TYPE: DNA
<213> ORGANISM: Artificial Sequence
<220> FEATURE:
<223> OTHER INFORMATION: Synthetic Sequence VL-SARAH(37C) of t8E4 Antibody

<400> SEQUENCE: 56

```
atggatatcc agatgacaca gactacatcc tccctgtctg cctctctggg agacagagtc      60
accttcagtt gcagggcaag tcaggacatt agcaattatt taaactggta tcaacagaag     120
ccagatggaa ctgttaaact cctgatcttc tacacatcaa gattacactc aggagtccca     180
tcaaggttca gtggcagtgg gtctgggaca gattattctc tcactattgc caacctggaa     240
caagaagatt ttgccactta cttttgccaa caggatagta gcatccgtt acgttcgga      300
tcggggacca agctggaaat aaaacgggga tccgactacg agtttcttaa gagttggaca     360
gtggaggacc ttcagaagag gctcttggcc ctggaccca tgatggagca ggagattgaa      420
gagatccggc agaagtacca gtgcaagcgg cagcccatcc tggatgccat agaggctaag     480
taa                                                                   483
```

<210> SEQ ID NO 57
<211> LENGTH: 495
<212> TYPE: DNA
<213> ORGANISM: Artificial Sequence
<220> FEATURE:
<223> OTHER INFORMATION: Synthetic Sequence VL-SARAH(37C) of 9E10 Antibody

<400> SEQUENCE: 57

```
atggacatcg ttttgactca gtctccggca tccctggcgg tctccctggg gcagcgggca      60
actatttcct gtcgggcgag cgaatccgtt gataactatg gttttccttc atgaactgg     120
tttcagcaga aaccgggcca gccgcccaag ctgctgatct atgccatcag taatcgcgga     180
tcaggcgtgc cagcgcgttt tagcggttcc gggtctggta ctgatttctc cctgaacatt     240
cacccagtgg aagaggatga ccctgccatg tacttttgcc agcagaccaa gaaagttccg     300
tggaccttcg gcgtgggac aaagctggag atcaaagcgg atccgactac gagtttctt      360
aagagttgga cagtggagga ccttcagaag aggctcttgg ccctggaccc catgatggag     420
caggagattg aagagatccg gcagaagtac cagtgcaagc ggcagcccat cctggatgcc     480
atagaggcta agtaa                                                      495
```

<210> SEQ ID NO 58
<211> LENGTH: 501
<212> TYPE: DNA
<213> ORGANISM: Artificial Sequence
<220> FEATURE:
<223> OTHER INFORMATION: Synthetic Sequence VL-SARAH(37C) of 12CA5
      Antibody

<400> SEQUENCE: 58

```
atggacatcg aattgactca gtctccgtct agcctgaccg ttactgcggg agagaaagtt      60
acaatgagct gtaagtcttc ccagagcctg ctgaatagcg gcaaccagaa aaactatctg     120
acctggtacc agcagaaacc tggtcagccg cccaagctgc tgatctattg ggcatcaaca     180
cgcgaaagcg gcgtgcctga tcgttttacc ggctctggta gtgggcggga cttcaccctg     240
acaatcagct ccgtgcaggc cgaagatctg gcggtttatt actgccagaa cgacaattct     300
cacccgctga cttttggagc cggcaccaaa ctggagctga aagcgggatc cgactacgag     360
tttcttaaga gttggacagt ggaggacctt cagaagaggc tcttggccct ggaccccatg     420
atggagcagg agattgaaga gatccggcag aagtaccagt gcaagcggca gcccatcctg     480
gatgccatag aggctaagta a                                               501
```

<210> SEQ ID NO 59
<211> LENGTH: 498
<212> TYPE: DNA
<213> ORGANISM: Artificial Sequence
<220> FEATURE:
<223> OTHER INFORMATION: Synthetic Sequence VL-SARAH(37C) of t1E4
      Antibody

<400> SEQUENCE: 59

```
atggatgttg tgatgaccca aactccactc tccctgcctg tcagtcttgg agatcaagcc      60
tccatctctt gcagatctag tcagagcctt gtacacagta tggaaacac ctatttacat      120 tggtacctgc agaagccagg ccagtctcca aagctcctga tctacaaagt ttccaaccga     180
ttttctgggg tcccagacag gttcagtggc agtggatcag gacagatttt cacactcaag     240
atcagcagag tggaggctga ggatctggga gtttatttct gctctcaaag tacacatgtt     300
ccgtatacgt tcggatcggg gaccaagttg gaaataaaac ggggatccga ctacgagttt     360
cttaagagtt ggacagtgga ggaccttcag aagaggctct ggccctgga ccccatgatg     420 gagcaggaga ttgaagagat ccggcagaag taccagtgca agcggcagcc catcctggat     480
gccatagagg ctaagtaa                                                   498
```

<210> SEQ ID NO 60
<211> LENGTH: 489
<212> TYPE: DNA
<213> ORGANISM: Artificial Sequence
<220> FEATURE:
<223> OTHER INFORMATION: Synthetic Sequence VL-SARAH(37C) of NZ-1
      Antibody

<400> SEQUENCE: 60

```
atgcagtttg tgcttactca gccaaactct gtgtctacga atctcggaag cacagtcaaa      60
ctgtcttgta agcgcagcac tggtaacatt ggaagcaatt atgtgaactg gtaccagcag     120
catgagggaa gatctcccac cactatgatt tataggatg ataagagacc agatggagtt      180
cctgacaggt tctctggctc cattgacaga tcttccaact cagccctcct gacaatcaat     240
aatgtgcaga ctgaagatga agctgactac ttctgtcact cttacagtag tggtattgtt     300
```

```
ttcggtggtg aaccaagct cactgtccta ggtggatccg actacgagtt tcttaagagt    360
tggacagtgg aggaccttca gaagaggctc ttggccctgg accccatgat ggagcaggag    420
attgaagaga tccggcagaa gtaccagtgc aagcggcagc ccatcctgga tgccatagag    480
gctaagtaa                                                            489
```

```
<210> SEQ ID NO 61
<211> LENGTH: 172
<212> TYPE: PRT
<213> ORGANISM: Artificial Sequence
<220> FEATURE:
<223> OTHER INFORMATION: Synthetic Sequence VH(112C)-SARAH of 93201
      Antibody

<400> SEQUENCE: 61
```

Met Glu Val Gln Leu Gln Gln Ser Gly Ala Glu Leu Val Lys Pro Gly
1               5                   10                  15

Ala Ser Val Lys Leu Ser Cys Thr Ala Ser Gly Phe Asn Ile Gln Asp
                20                  25                  30

Thr Tyr Ile His Trp Val Lys Gln Arg Pro Glu Gln Gly Leu Asp Trp
            35                  40                  45

Ile Gly Arg Ile Asp Pro Ala Asn Gly Asn Thr Lys Tyr Asp Pro Asn
        50                  55                  60

Phe Gln Gly Lys Ala Thr Ile Thr Ala Asp Thr Ser Ser Asn Thr Ala
65                  70                  75                  80

Tyr Leu Gln Leu Ser Ser Leu Ala Ser Glu Asp Thr Ala Val Tyr Tyr
                85                  90                  95

Cys Ala Thr Ser Asn Tyr Tyr Ser Arg Gly Ala Met Asp Tyr Trp Gly
            100                 105                 110

Gln Gly Thr Ser Val Thr Val Cys Ser Gly Ser Asp Tyr Glu Phe Leu
        115                 120                 125

Lys Ser Trp Thr Val Glu Asp Leu Gln Lys Arg Leu Leu Ala Leu Asp
    130                 135                 140

Pro Met Met Glu Gln Glu Ile Glu Glu Ile Arg Gln Lys Tyr Gln Ser
145                 150                 155                 160

Lys Arg Gln Pro Ile Leu Asp Ala Ile Glu Ala Lys
                165                 170

```
<210> SEQ ID NO 62
<211> LENGTH: 172
<212> TYPE: PRT
<213> ORGANISM: Artificial Sequence
<220> FEATURE:
<223> OTHER INFORMATION: Synthetic Sequence VH(112C)-SARAH of TS2/16
      Antibody

<400> SEQUENCE: 62
```

Met Asp Val Lys Leu Val Glu Ser Gly Gly Gly Leu Val Lys Pro Gly
1               5                   10                  15

Gly Ser Leu Lys Leu Ser Cys Ala Ala Ser Gly Phe Thr Phe Ser Ser
                20                  25                  30

Tyr Thr Met Ser Trp Val Arg Gln Thr Pro Glu Lys Arg Leu Glu Trp
            35                  40                  45

Val Ala Thr Ile Ser Ser Gly Gly Ser Tyr Thr Tyr Tyr Pro Asp Ser
        50                  55                  60

Val Lys Gly Arg Phe Thr Ile Ser Arg Asp Lys Ala Lys Asn Thr Leu
65                  70                  75                  80

Tyr Leu Gln Met Gly Ser Leu Lys Ser Glu Asp Thr Ala Met Tyr Tyr

```
                    85                  90                  95
Cys Thr Arg Ile Gly Tyr Asp Glu Asp Tyr Ala Met Asp His Trp Gly
                100                 105                 110

Gln Gly Thr Ser Val Thr Val Cys Ser Gly Ser Asp Tyr Glu Phe Leu
            115                 120                 125

Lys Ser Trp Thr Val Glu Asp Leu Gln Lys Arg Leu Leu Ala Leu Asp
        130                 135                 140

Pro Met Met Glu Gln Glu Ile Glu Ile Arg Gln Lys Tyr Gln Ser
145                 150                 155                 160

Lys Arg Gln Pro Ile Leu Asp Ala Ile Glu Ala Lys
                165                 170

<210> SEQ ID NO 63
<211> LENGTH: 170
<212> TYPE: PRT
<213> ORGANISM: Artificial Sequence
<220> FEATURE:
<223> OTHER INFORMATION: Synthetic Sequence VH(112C)-SARAH of SG/19
      Antibody

<400> SEQUENCE: 63

Met Gln Val His Leu Gln Gln Ser Gly Ala Glu Leu Met Lys Pro Gly
1               5                   10                  15

Ala Ser Val Lys Ile Ser Cys Lys Ala Thr Gly Tyr Thr Phe Thr Ser
            20                  25                  30

Tyr Trp Ile Glu Trp Val Lys Gln Arg Pro Gly His Gly Leu Glu Trp
        35                  40                  45

Leu Gly Glu Ile Leu Pro Gly Ser Gly Tyr Ile His Tyr Asn Glu Lys
    50                  55                  60

Phe Lys Gly Lys Ala Thr Phe Thr Thr Asp Thr Ser Ser Asn Thr Ala
65                  70                  75                  80

Tyr Met Gln Leu Ser Ser Leu Thr Ser Glu Asp Ser Ala Val Tyr Tyr
                85                  90                  95

Cys Ser Arg Ala Leu Ala Leu Tyr Ala Met Asp Tyr Trp Gly Gln Gly
                100                 105                 110

Thr Ser Val Thr Val Cys Ser Gly Ser Asp Tyr Glu Phe Leu Lys Ser
            115                 120                 125

Trp Thr Val Glu Asp Leu Gln Lys Arg Leu Leu Ala Leu Asp Pro Met
        130                 135                 140

Met Glu Gln Glu Ile Glu Ile Arg Gln Lys Tyr Gln Ser Lys Arg
145                 150                 155                 160

Gln Pro Ile Leu Asp Ala Ile Glu Ala Lys
                165                 170

<210> SEQ ID NO 64
<211> LENGTH: 174
<212> TYPE: PRT
<213> ORGANISM: Artificial Sequence
<220> FEATURE:
<223> OTHER INFORMATION: Synthetic Sequence VH(112C)-SARAH of t8E4
      Antibody

<400> SEQUENCE: 64

Met Lys Gln Val Gln Leu Lys Glu Ser Gly Pro Asp Leu Val Gln Pro
1               5                   10                  15

Ser Gln Thr Leu Ser Leu Thr Cys Thr Val Ser Gly Phe Ser Leu Thr
            20                  25                  30

Gly Tyr Gly Val His Trp Val Arg Gln Pro Pro Gly Lys Gly Leu Glu
```

```
                35                  40                  45
Trp Val Gly Thr Leu Gly Trp Asn Asp Lys Tyr Tyr Asn Ser Ala
             50                  55                  60

Leu Lys Ser Arg Leu Ser Ile Ser Arg Asp Thr Ser Lys Asn Gln Val
 65                  70                  75                  80

Phe Leu Lys Leu Ser Ser Leu Glu Thr Glu Asp Thr Ala Met Tyr Tyr
                 85                  90                  95

Cys Thr Arg Asp Gly Gly Leu Leu Phe Ala Tyr Tyr Ala Met Asp Tyr
                100                 105                 110

Trp Gly Gln Gly Thr Ser Val Thr Val Cys Ser Gly Ser Asp Tyr Glu
                115                 120                 125

Phe Leu Lys Ser Trp Thr Val Glu Asp Leu Gln Lys Arg Leu Leu Ala
                130                 135                 140

Leu Asp Pro Met Met Glu Gln Glu Ile Glu Ile Arg Gln Lys Tyr
145                 150                 155                 160

Gln Ser Lys Arg Gln Pro Ile Leu Asp Ala Ile Glu Ala Lys
                165                 170

<210> SEQ ID NO 65
<211> LENGTH: 179
<212> TYPE: PRT
<213> ORGANISM: Artificial Sequence
<220> FEATURE:
<223> OTHER INFORMATION: Synthetic Sequence VH(112C)-SARAH of 9E10
      Antibody

<400> SEQUENCE: 65

Met Glu Val Lys Leu Val Glu Ser Gly Gly Asp Leu Val Lys Pro Gly
 1               5                  10                  15

Gly Ser Leu Lys Leu Ser Cys Ala Ala Ser Gly Phe Thr Phe Ser His
                 20                  25                  30

Tyr Gly Met Ser Trp Val Arg Gln Thr Pro Asp Lys Arg Leu Glu Trp
             35                  40                  45

Val Ala Thr Ile Gly Ser Arg Gly Thr Tyr Thr His Tyr Pro Asp Ser
 50                  55                  60

Val Lys Gly Arg Phe Thr Ile Ser Arg Asp Asn Asp Lys Asn Ala Leu
 65                  70                  75                  80

Tyr Leu Gln Met Asn Ser Leu Lys Ser Glu Asp Thr Ala Met Tyr Tyr
                 85                  90                  95

Cys Ala Arg Arg Ser Glu Phe Tyr Tyr Tyr Gly Asn Thr Tyr Tyr Tyr
                100                 105                 110

Ser Ala Met Asp Tyr Trp Gly Gln Gly Ala Ser Val Thr Val Cys Ser
                115                 120                 125

Gly Ser Asp Tyr Glu Phe Leu Lys Ser Trp Thr Val Glu Asp Leu Gln
                130                 135                 140

Lys Arg Leu Leu Ala Leu Asp Pro Met Met Glu Gln Glu Ile Glu Glu
145                 150                 155                 160

Ile Arg Gln Lys Tyr Gln Ser Lys Arg Gln Pro Ile Leu Asp Ala Ile
                165                 170                 175

Glu Ala Lys

<210> SEQ ID NO 66
<211> LENGTH: 172
<212> TYPE: PRT
<213> ORGANISM: Artificial Sequence
<220> FEATURE:
<223> OTHER INFORMATION: Synthetic Sequence VH(112C)-SARAH of 12CA5
```

Antibody

<400> SEQUENCE: 66

Met Glu Val Lys Leu Val Glu Ser Gly Gly Asp Leu Val Lys Pro Gly
1               5                   10                  15

Gly Ser Leu Lys Leu Ser Cys Ala Ala Ser Gly Phe Thr Phe Ser Ser
            20                  25                  30

Tyr Gly Met Ser Trp Val Arg Gln Thr Pro Asp Lys Arg Leu Glu Trp
        35                  40                  45

Val Ala Thr Ile Ser Arg Gly Gly Ser Tyr Thr Tyr Tyr Pro Asp Ser
    50                  55                  60

Val Lys Gly Arg Phe Thr Ile Ser Arg Asp Asn Ala Lys Asn Thr Leu
65                  70                  75                  80

Tyr Leu Gln Met Ser Ser Leu Lys Ser Glu Asp Thr Ala Met Tyr Tyr
                85                  90                  95

Cys Ala Arg Arg Glu Thr Tyr Asp Glu Lys Gly Phe Ala Tyr Trp Gly
            100                 105                 110

Gln Gly Thr Thr Val Thr Val Cys Ser Gly Ser Asp Tyr Glu Phe Leu
        115                 120                 125

Lys Ser Trp Thr Val Glu Asp Leu Gln Lys Arg Leu Leu Ala Leu Asp
130                 135                 140

Pro Met Met Glu Gln Glu Ile Glu Glu Ile Arg Gln Lys Tyr Gln Ser
145                 150                 155                 160

Lys Arg Gln Pro Ile Leu Asp Ala Ile Glu Ala Lys
            165                 170

<210> SEQ ID NO 67
<211> LENGTH: 173
<212> TYPE: PRT
<213> ORGANISM: Artificial Sequence
<220> FEATURE:
<223> OTHER INFORMATION: Synthetic Sequence VH(112C)-SARAH of t1E4
      Antibody

<400> SEQUENCE: 67

Met Lys Gln Gly Gln Leu Gln Gln Ser Gly Pro Glu Leu Val Lys Pro
1               5                   10                  15

Gly Ala Ser Val Lys Ile Ser Cys Lys Ala Ser Gly Tyr Val Phe Ser
            20                  25                  30

Ser Ser Trp Met Asn Trp Val Lys Gln Arg Pro Gly Lys Gly Leu Glu
        35                  40                  45

Trp Ile Gly Arg Ile Tyr Pro Gly Tyr Gly Asp Thr Asn Tyr Asn Gly
    50                  55                  60

Lys Phe Lys Gly Lys Ala Thr Leu Thr Ala Asp Lys Ser Ser Ser Thr
65                  70                  75                  80

Ala Tyr Met Gln Leu Ser Ser Leu Thr Ser Glu Asp Ser Ala Val Tyr
                85                  90                  95

Phe Cys Val Arg Glu Glu Leu Gly Pro Tyr Trp Tyr Phe Asp Val Trp
            100                 105                 110

Gly Ala Gly Thr Thr Val Thr Val Cys Ser Gly Ser Asp Tyr Glu Phe
        115                 120                 125

Leu Lys Ser Trp Thr Val Glu Asp Leu Gln Lys Arg Leu Leu Ala Leu
        130                 135                 140

Asp Pro Met Met Glu Gln Glu Ile Glu Glu Ile Arg Gln Lys Tyr Gln
145                 150                 155                 160

Ser Lys Arg Gln Pro Ile Leu Asp Ala Ile Glu Ala Lys
            165                 170

<210> SEQ ID NO 68
<211> LENGTH: 170
<212> TYPE: PRT
<213> ORGANISM: Artificial Sequence
<220> FEATURE:
<223> OTHER INFORMATION: Synthetic Sequence VH(112C)-SARAH of NZ-1
      Antibody

<400> SEQUENCE: 68

Met Lys Glu Val Gln Leu Val Glu Ser Gly Gly Gly Leu Val Gln Pro
1               5                   10                  15

Gly Arg Ser Leu Lys Leu Ser Cys Ala Ala Ser Gly Phe Thr Phe Ser
            20                  25                  30

Asn Tyr Gly Met Ala Trp Val Arg Gln Thr Pro Thr Lys Gly Leu Glu
        35                  40                  45

Trp Ile Ala Ser Ile Ser Ala Gly Gly Asp Lys Thr Tyr Tyr Gly Asp
    50                  55                  60

Ser Val Lys Gly Arg Phe Ser Ile Ser Arg Asp Asn Ala Lys Thr Thr
65                  70                  75                  80

His Tyr Leu Gln Met Asp Ser Leu Arg Ser Glu Asp Thr Ala Thr Tyr
                85                  90                  95

Tyr Cys Ala Lys Thr Ser Arg Val Tyr Phe Asp Tyr Trp Gly Gln Gly
            100                 105                 110

Val Met Val Thr Val Cys Ser Gly Ser Asp Tyr Glu Phe Leu Lys Ser
        115                 120                 125

Trp Thr Val Glu Asp Leu Gln Lys Arg Leu Leu Ala Leu Asp Pro Met
    130                 135                 140

Met Glu Gln Glu Ile Glu Ile Arg Gln Lys Tyr Gln Ser Lys Arg
145                 150                 155                 160

Gln Pro Ile Leu Asp Ala Ile Glu Ala Lys
                165                 170

<210> SEQ ID NO 69
<211> LENGTH: 164
<212> TYPE: PRT
<213> ORGANISM: Artificial Sequence
<220> FEATURE:
<223> OTHER INFORMATION: Synthetic Sequence VL-SARAH(37C) of 93201
      Antibody

<400> SEQUENCE: 69

Met Asp Ile Val Leu Thr Gln Ser Pro Ala Ser Leu Ala Val Ser Leu
1               5                   10                  15

Gly Gln Arg Ala Thr Ile Ser Cys Arg Ala Ser Glu Ser Val Glu Tyr
            20                  25                  30

Tyr Gly Thr Asn Leu Met His Trp Tyr Gln Gln Lys Pro Gly Gln Pro
        35                  40                  45

Pro Lys Leu Leu Ile Tyr Val Ala Ser Thr Val Lys Ser Gly Val Pro
    50                  55                  60

Ala Arg Phe Ser Gly Ser Gly Ser Gly Thr Asp Phe Ser Leu Asn Ile
65                  70                  75                  80

His Pro Val Glu Glu Asp Asp Ile Ala Met Tyr Phe Cys Gln Gln Ser
                85                  90                  95

Arg Lys Val Pro Trp Thr Phe Gly Gly Gly Thr Arg Leu Glu Ile Lys
            100                 105                 110

Arg Gly Ser Asp Tyr Glu Phe Leu Lys Ser Trp Thr Val Glu Asp Leu

```
                115                 120                 125
Gln Lys Arg Leu Leu Ala Leu Asp Pro Met Met Glu Gln Glu Ile Glu
            130                 135                 140
Glu Ile Arg Gln Lys Tyr Gln Cys Lys Arg Gln Pro Ile Leu Asp Ala
145                 150                 155                 160
Ile Glu Ala Lys

<210> SEQ ID NO 70
<211> LENGTH: 161
<212> TYPE: PRT
<213> ORGANISM: Artificial Sequence
<220> FEATURE:
<223> OTHER INFORMATION: Artificial Sequence VL-SARAH(37C) of TS2/16
      Antibody

<400> SEQUENCE: 70

Met Gln Ile Val Val Thr Gln Arg Pro Thr Thr Met Ala Ala Ser Pro
1               5                   10                  15
Gly Asp Lys Ile Ile Ile Thr Cys Ser Val Ser Ser Ile Ile Ser Ser
            20                  25                  30
Asn Tyr Leu His Trp Tyr Ser Gln Lys Pro Gly Phe Ser Pro Lys Leu
        35                  40                  45
Leu Ile Tyr Arg Thr Ser Asn Leu Ala Ser Gly Val Pro Pro Arg Phe
    50                  55                  60
Ser Gly Ser Gly Ser Gly Thr Ser Tyr Ser Leu Thr Ile Gly Thr Met
65                  70                  75                  80
Glu Ala Glu Asp Val Ala Thr Tyr Tyr Cys Gln Gln Gly Ser Asp Ile
                85                  90                  95
Pro Leu Thr Phe Gly Asp Gly Thr Lys Leu Asp Leu Lys Arg Gly Ser
            100                 105                 110
Asp Tyr Glu Phe Leu Lys Ser Trp Thr Val Glu Asp Leu Gln Lys Arg
        115                 120                 125
Leu Leu Ala Leu Asp Pro Met Met Glu Gln Glu Ile Glu Glu Ile Arg
    130                 135                 140
Gln Lys Tyr Gln Cys Lys Arg Gln Pro Ile Leu Asp Ala Ile Glu Ala
145                 150                 155                 160
Lys

<210> SEQ ID NO 71
<211> LENGTH: 165
<212> TYPE: PRT
<213> ORGANISM: Artificial Sequence
<220> FEATURE:
<223> OTHER INFORMATION: Artificial Sequence VL-SARAH(37C) of SG/19
      Antibody

<400> SEQUENCE: 71

Met Asp Ile Val Met Thr Gln Ala Thr Pro Ser Ile Pro Val Thr Pro
1               5                   10                  15
Gly Glu Ser Val Ser Ile Ser Cys Arg Ser Asn Lys Ser Leu Leu His
            20                  25                  30
Ser Asn Gly Asn Thr Tyr Leu Tyr Trp Phe Leu Gln Arg Pro Gly Gln
        35                  40                  45
Ser Pro Arg Leu Leu Ile Phe Arg Met Ser Asn Leu Ala Ser Gly Val
    50                  55                  60
Pro Asp Arg Phe Ser Gly Ser Gly Ser Gly Thr Ala Phe Thr Leu Arg
65                  70                  75                  80
```

Ile Ser Arg Val Glu Ala Ala Asp Val Gly Ile Tyr Phe Cys Leu Gln
                85                  90                  95

His Leu Glu Tyr Pro Phe Thr Phe Gly Ala Gly Thr Lys Leu Glu Leu
            100                 105                 110

Lys Arg Gly Ser Asp Tyr Glu Phe Leu Lys Ser Trp Thr Val Glu Asp
            115                 120                 125

Leu Gln Lys Arg Leu Leu Ala Leu Asp Pro Met Met Glu Gln Glu Ile
            130                 135                 140

Glu Glu Ile Arg Gln Lys Tyr Gln Cys Lys Arg Gln Pro Ile Leu Asp
145                 150                 155                 160

Ala Ile Glu Ala Lys
            165

<210> SEQ ID NO 72
<211> LENGTH: 160
<212> TYPE: PRT
<213> ORGANISM: Artificial Sequence
<220> FEATURE:
<223> OTHER INFORMATION: Artificial Sequence VL-SARAH(37C) of t8E4
      Antibody

<400> SEQUENCE: 72

Met Asp Ile Gln Met Thr Gln Thr Thr Ser Ser Leu Ser Ala Ser Leu
1               5                   10                  15

Gly Asp Arg Val Thr Phe Ser Cys Arg Ala Ser Gln Asp Ile Ser Asn
            20                  25                  30

Tyr Leu Asn Trp Tyr Gln Gln Lys Pro Asp Gly Thr Val Lys Leu Leu
        35                  40                  45

Ile Phe Tyr Thr Ser Arg Leu His Ser Gly Val Pro Ser Arg Phe Ser
    50                  55                  60

Gly Ser Gly Ser Gly Thr Asp Tyr Ser Leu Thr Ile Ala Asn Leu Glu
65                  70                  75                  80

Gln Glu Asp Phe Ala Thr Tyr Phe Cys Gln Gln Asp Ser Lys His Pro
                85                  90                  95

Phe Thr Phe Gly Ser Gly Thr Lys Leu Glu Ile Lys Arg Gly Ser Asp
            100                 105                 110

Tyr Glu Phe Leu Lys Ser Trp Thr Val Glu Asp Leu Gln Lys Arg Leu
            115                 120                 125

Leu Ala Leu Asp Pro Met Met Glu Gln Glu Ile Glu Glu Ile Arg Gln
            130                 135                 140

Lys Tyr Gln Cys Lys Arg Gln Pro Ile Leu Asp Ala Ile Glu Ala Lys
145                 150                 155                 160

<210> SEQ ID NO 73
<211> LENGTH: 164
<212> TYPE: PRT
<213> ORGANISM: Artificial Sequence
<220> FEATURE:
<223> OTHER INFORMATION: Artificial Sequence VL-SARAH(37C) of 9E10
      Antibody

<400> SEQUENCE: 73

Met Asp Ile Val Leu Thr Gln Ser Pro Ala Ser Leu Ala Val Ser Leu
1               5                   10                  15

Gly Gln Arg Ala Thr Ile Ser Cys Arg Ala Ser Glu Ser Val Asp Asn
            20                  25                  30

Tyr Gly Phe Ser Phe Met Asn Trp Phe Gln Gln Lys Pro Gly Gln Pro
        35                  40                  45

```
Pro Lys Leu Leu Ile Tyr Ala Ile Ser Asn Arg Gly Ser Gly Val Pro
    50                  55                  60

Ala Arg Phe Ser Gly Ser Gly Ser Gly Thr Asp Phe Ser Leu Asn Ile
65              70                  75                  80

His Pro Val Glu Glu Asp Asp Pro Ala Met Tyr Phe Cys Gln Gln Thr
                85                  90                  95

Lys Glu Val Pro Trp Thr Phe Gly Gly Gly Thr Lys Leu Glu Ile Lys
                100                 105                 110

Ala Gly Ser Asp Tyr Glu Phe Leu Lys Ser Trp Thr Val Glu Asp Leu
            115                 120                 125

Gln Lys Arg Leu Leu Ala Leu Asp Pro Met Met Glu Gln Glu Ile Glu
    130                 135                 140

Glu Ile Arg Gln Lys Tyr Gln Cys Lys Arg Gln Pro Ile Leu Asp Ala
145                 150                 155                 160

Ile Glu Ala Lys
```

<210> SEQ ID NO 74
<211> LENGTH: 166
<212> TYPE: PRT
<213> ORGANISM: Artificial Sequence
<220> FEATURE:
<223> OTHER INFORMATION: Artificial Sequence VL-SARAH(37C) of 12CA5
      Antibody

<400> SEQUENCE: 74

```
Met Asp Ile Glu Leu Thr Gln Ser Pro Ser Ser Leu Thr Val Thr Ala
1               5                   10                  15

Gly Glu Lys Val Thr Met Ser Cys Lys Ser Ser Gln Ser Leu Leu Asn
                20                  25                  30

Ser Gly Asn Gln Lys Asn Tyr Leu Thr Trp Tyr Gln Gln Lys Pro Gly
            35                  40                  45

Gln Pro Pro Lys Leu Leu Ile Tyr Trp Ala Ser Thr Arg Glu Ser Gly
    50                  55                  60

Val Pro Asp Arg Phe Thr Gly Ser Gly Ser Gly Arg Asp Phe Thr Leu
65              70                  75                  80

Thr Ile Ser Ser Val Gln Ala Glu Asp Leu Ala Val Tyr Tyr Cys Gln
                85                  90                  95

Asn Asp Asn Ser His Pro Leu Thr Phe Gly Ala Gly Thr Lys Leu Glu
                100                 105                 110

Leu Lys Ala Gly Ser Asp Tyr Glu Phe Leu Lys Ser Trp Thr Val Glu
            115                 120                 125

Asp Leu Gln Lys Arg Leu Leu Ala Leu Asp Pro Met Met Glu Gln Glu
    130                 135                 140

Ile Glu Glu Ile Arg Gln Lys Tyr Gln Cys Lys Arg Gln Pro Ile Leu
145                 150                 155                 160

Asp Ala Ile Glu Ala Lys
                165
```

<210> SEQ ID NO 75
<211> LENGTH: 165
<212> TYPE: PRT
<213> ORGANISM: Artificial Sequence
<220> FEATURE:
<223> OTHER INFORMATION: Artificial Sequence VL-SARAH(37C) of t1E4
      Antibody

<400> SEQUENCE: 75

Met Asp Val Val Met Thr Gln Thr Pro Leu Ser Leu Pro Val Ser Leu

```
                1               5                  10                 15
        Gly Asp Gln Ala Ser Ile Ser Cys Arg Ser Ser Gln Ser Leu Val His
                        20                  25                 30

Ser Asn Gly Asn Thr Tyr Leu His Trp Tyr Leu Gln Lys Pro Gly Gln
                        35                  40                 45

Ser Pro Lys Leu Leu Ile Tyr Lys Val Ser Asn Arg Phe Ser Gly Val
                50                  55                  60

Pro Asp Arg Phe Ser Gly Ser Gly Ser Gly Thr Asp Phe Thr Leu Lys
        65                  70                  75                  80

Ile Ser Arg Val Glu Ala Glu Asp Leu Gly Val Tyr Phe Cys Ser Gln
                        85                  90                 95

Ser Thr His Val Pro Tyr Thr Phe Gly Ser Gly Thr Lys Leu Glu Ile
                        100                 105                110

Lys Arg Gly Ser Asp Tyr Glu Phe Leu Lys Ser Trp Thr Val Glu Asp
                        115                 120                125

Leu Gln Lys Arg Leu Leu Ala Leu Asp Pro Met Met Glu Gln Glu Ile
                        130                 135                140

Glu Glu Ile Arg Gln Lys Tyr Gln Cys Lys Arg Gln Pro Ile Leu Asp
        145                 150                 155                 160

Ala Ile Glu Ala Lys
                        165
```

```
<210> SEQ ID NO 76
<211> LENGTH: 162
<212> TYPE: PRT
<213> ORGANISM: Artificial Sequence
<220> FEATURE:
<223> OTHER INFORMATION: Artificial Sequence VL-SARAH(37C) of NZ-1
      Antibody

<400> SEQUENCE: 76
```

```
        Met Gln Phe Val Leu Thr Gln Pro Asn Ser Val Ser Thr Asn Leu Gly
        1               5                   10                  15

Ser Thr Val Lys Leu Ser Cys Lys Arg Ser Thr Gly Asn Ile Gly Ser
                        20                  25                 30

Asn Tyr Val Asn Trp Tyr Gln Gln His Glu Gly Arg Ser Pro Thr Thr
                        35                  40                 45

Met Ile Tyr Arg Asp Asp Lys Arg Pro Asp Gly Val Pro Asp Arg Phe
                50                  55                  60

Ser Gly Ser Ile Asp Arg Ser Ser Asn Ser Ala Leu Leu Thr Ile Asn
        65                  70                  75                  80

Asn Val Gln Thr Glu Asp Glu Ala Asp Tyr Phe Cys His Ser Tyr Ser
                        85                  90                 95

Ser Gly Ile Val Phe Gly Gly Gly Thr Lys Leu Thr Val Leu Gly Gly
                        100                 105                110

Ser Asp Tyr Glu Phe Leu Lys Ser Trp Thr Val Glu Asp Leu Gln Lys
                        115                 120                125

Arg Leu Leu Ala Leu Asp Pro Met Met Glu Gln Glu Ile Glu Glu Ile
                        130                 135                140

Arg Gln Lys Tyr Gln Cys Lys Arg Gln Pro Ile Leu Asp Ala Ile Glu
        145                 150                 155                 160

Ala Lys
```

```
<210> SEQ ID NO 77
<211> LENGTH: 677
<212> TYPE: PRT
```

<213> ORGANISM: Artificial Sequence
<220> FEATURE:
<223> OTHER INFORMATION: Artificial Sequence SORLA Vps10p Domain

<400> SEQUENCE: 77

```
Gln Pro Glu Pro Ile Lys Val Tyr Gly Gln Val Ser Leu Asn Asp Ser
1               5                   10                  15

His Asn Gln Met Val Val His Trp Ala Gly Glu Lys Ser Asn Val Ile
            20                  25                  30

Val Ala Leu Ala Arg Asp Ser Leu Ala Leu Ala Arg Pro Lys Ser Ser
        35                  40                  45

Asp Val Tyr Val Ser Tyr Asp Tyr Gly Lys Ser Phe Lys Lys Ile Ser
    50                  55                  60

Asp Lys Leu Asn Phe Gly Leu Gly Asn Arg Ser Glu Ala Val Ile Ala
65                  70                  75                  80

Gln Phe Tyr His Ser Pro Ala Asp Asn Lys Arg Tyr Ile Phe Ala Asp
                85                  90                  95

Ala Tyr Ala Gln Tyr Leu Trp Ile Thr Phe Asp Phe Cys Asn Thr Leu
            100                 105                 110

Gln Gly Phe Ser Ile Pro Phe Arg Ala Ala Asp Leu Leu Leu His Ser
        115                 120                 125

Lys Ala Ser Asn Leu Leu Leu Gly Phe Asp Arg Ser His Pro Asn Lys
    130                 135                 140

Gln Leu Trp Lys Ser Asp Asp Phe Gly Gln Thr Trp Ile Met Ile Gln
145                 150                 155                 160

Glu His Val Lys Ser Phe Ser Trp Gly Ile Asp Pro Tyr Asp Lys Pro
                165                 170                 175

Asn Thr Ile Tyr Ile Glu Arg His Glu Pro Ser Gly Tyr Ser Thr Val
            180                 185                 190

Phe Arg Ser Thr Asp Phe Phe Gln Ser Arg Glu Asn Gln Glu Val Ile
        195                 200                 205

Leu Glu Glu Val Arg Asp Phe Gln Leu Arg Asp Lys Tyr Met Phe Ala
    210                 215                 220

Thr Lys Val Val His Leu Leu Gly Ser Glu Gln Gln Ser Ser Val Gln
225                 230                 235                 240

Leu Trp Val Ser Phe Gly Arg Lys Pro Met Arg Ala Ala Gln Phe Val
                245                 250                 255

Thr Arg His Pro Ile Asn Glu Tyr Tyr Ile Ala Asp Ala Ser Glu Asp
            260                 265                 270

Gln Val Phe Val Cys Val Ser His Ser Asn Asn Arg Thr Asn Leu Tyr
        275                 280                 285

Ile Ser Glu Ala Glu Gly Leu Lys Phe Ser Leu Ser Leu Glu Asn Val
    290                 295                 300

Leu Tyr Tyr Ser Pro Gly Gly Ala Gly Ser Asp Thr Leu Val Arg Tyr
305                 310                 315                 320

Phe Ala Asn Glu Pro Phe Ala Asp Phe His Arg Val Glu Gly Leu Gln
                325                 330                 335

Gly Val Tyr Ile Ala Thr Leu Ile Asn Gly Ser Met Asn Glu Glu Asn
            340                 345                 350

Met Arg Ser Val Ile Thr Phe Asp Lys Gly Gly Thr Trp Glu Phe Leu
        355                 360                 365

Gln Ala Pro Ala Phe Thr Gly Tyr Gly Glu Lys Ile Asn Cys Glu Leu
    370                 375                 380

Ser Gln Gly Cys Ser Leu His Leu Ala Gln Arg Leu Ser Gln Leu Leu
```

```
                385                 390                 395                 400
Asn Leu Gln Leu Arg Arg Met Pro Ile Leu Ser Lys Glu Ser Ala Pro
                    405                 410                 415

Gly Leu Ile Ile Ala Thr Gly Ser Val Gly Lys Asn Leu Ala Ser Lys
                420                 425                 430

Thr Asn Val Tyr Ile Ser Ser Ala Gly Ala Arg Trp Arg Glu Ala
                435                 440                 445

Leu Pro Gly Pro His Tyr Tyr Thr Trp Gly Asp His Gly Ile Ile
    450                 455                 460

Thr Ala Ile Ala Gln Gly Met Glu Thr Asn Glu Leu Lys Tyr Ser Thr
465                 470                 475                 480

Asn Glu Gly Glu Thr Trp Lys Thr Phe Ile Phe Ser Glu Lys Pro Val
                    485                 490                 495

Phe Val Tyr Gly Leu Leu Thr Glu Pro Gly Glu Lys Ser Thr Val Phe
                500                 505                 510

Thr Ile Phe Gly Ser Asn Lys Glu Asn Val His Ser Trp Leu Ile Leu
            515                 520                 525

Gln Val Asn Ala Thr Asp Ala Leu Gly Val Pro Cys Thr Glu Asn Asp
    530                 535                 540

Tyr Lys Leu Trp Ser Pro Ser Asp Glu Arg Gly Asn Glu Cys Leu Leu
545                 550                 555                 560

Gly His Lys Thr Val Phe Lys Arg Arg Thr Pro His Ala Thr Cys Phe
                    565                 570                 575

Asn Gly Glu Asp Phe Asp Arg Pro Val Val Ser Asn Cys Ser Cys
                580                 585                 590

Thr Arg Glu Asp Tyr Glu Cys Asp Phe Gly Phe Lys Met Ser Glu Asp
            595                 600                 605

Leu Ser Leu Glu Val Cys Val Pro Asp Pro Glu Phe Ser Gly Lys Ser
    610                 615                 620

Tyr Ser Pro Pro Val Pro Cys Pro Val Gly Ser Thr Tyr Arg Arg Thr
625                 630                 635                 640

Arg Gly Tyr Arg Lys Ile Ser Gly Asp Thr Cys Ser Gly Gly Asp Val
                    645                 650                 655

Glu Ala Arg Leu Glu Gly Glu Leu Val Pro Cys Pro Ser Arg Leu Glu
                660                 665                 670

Asn Leu Tyr Phe Gln
            675

<210> SEQ ID NO 78
<211> LENGTH: 627
<212> TYPE: PRT
<213> ORGANISM: Artificial Sequence
<220> FEATURE:
<223> OTHER INFORMATION: Artificial Sequence Integrin 6

<400> SEQUENCE: 78

Phe Asn Leu Asp Thr Arg Glu Asp Asn Val Ile Arg Lys Tyr Gly Asp
1               5                   10                  15

Pro Gly Ser Leu Phe Gly Phe Ser Leu Ala Met His Trp Gln Leu Gln
                20                  25                  30

Pro Glu Asp Lys Arg Leu Leu Val Gly Ala Pro Ala Glu Ala
            35                  40                  45

Leu Pro Leu Gln Arg Ala Asn Arg Thr Gly Gly Leu Tyr Ser Cys Asp
    50                  55                  60

Ile Thr Ala Arg Gly Pro Cys Thr Arg Ile Glu Phe Asp Asn Asp Ala
```

```
            65                  70                  75                  80
Asp Pro Thr Ser Glu Ser Lys Glu Asp Gln Trp Met Gly Val Thr Val
                    85                  90                  95
Gln Ser Gln Gly Pro Gly Lys Val Val Thr Cys Ala His Arg Tyr
                100                 105                 110
Glu Lys Arg Gln His Val Asn Thr Lys Gln Glu Ser Arg Asp Ile Phe
                115                 120                 125
Gly Arg Cys Tyr Val Leu Ser Gln Asn Leu Arg Ile Glu Asp Asp Met
            130                 135                 140
Asp Gly Gly Asp Trp Ser Phe Cys Asp Gly Arg Leu Arg Gly His Glu
145                 150                 155                 160
Lys Phe Gly Ser Cys Gln Gln Gly Val Ala Ala Thr Phe Thr Lys Asp
                165                 170                 175
Phe His Tyr Ile Val Phe Gly Ala Pro Gly Thr Tyr Asn Trp Lys Gly
                180                 185                 190
Ile Val Arg Val Glu Gln Lys Asn Asn Thr Phe Phe Asp Met Asn Ile
            195                 200                 205
Phe Glu Asp Gly Pro Tyr Glu Val Gly Gly Glu Thr Glu His Asp Glu
210                 215                 220
Ser Leu Val Pro Val Pro Ala Asn Ser Tyr Leu Gly Phe Ser Leu Asp
225                 230                 235                 240
Ser Gly Lys Gly Ile Val Ser Lys Asp Glu Ile Thr Phe Val Ser Gly
                245                 250                 255
Ala Pro Arg Ala Asn His Ser Gly Ala Val Val Leu Leu Lys Arg Asp
                260                 265                 270
Met Lys Ser Ala His Leu Leu Pro Glu His Ile Phe Asp Gly Glu Gly
            275                 280                 285
Leu Ala Ser Ser Phe Gly Tyr Asp Val Ala Val Val Asp Leu Asn Lys
            290                 295                 300
Asp Gly Trp Gln Asp Ile Val Ile Gly Ala Pro Gln Tyr Phe Asp Arg
305                 310                 315                 320
Asp Gly Glu Val Gly Gly Ala Val Tyr Val Tyr Met Asn Gln Gln Gly
                325                 330                 335
Arg Trp Asn Asn Val Lys Pro Ile Arg Leu Asn Gly Thr Lys Asp Ser
                340                 345                 350
Met Phe Gly Ile Ala Val Lys Asn Ile Gly Asp Ile Asn Gln Asp Gly
            355                 360                 365
Tyr Pro Asp Ile Ala Val Gly Ala Pro Tyr Asp Asp Leu Gly Lys Val
            370                 375                 380
Phe Ile Tyr His Gly Ser Ala Asn Gly Ile Asn Thr Lys Pro Thr Gln
385                 390                 395                 400
Val Leu Lys Gly Ile Ser Pro Tyr Phe Gly Tyr Ser Ile Ala Gly Asn
                405                 410                 415
Met Asp Leu Asp Arg Asn Ser Tyr Pro Asp Val Ala Val Gly Ser Leu
            420                 425                 430
Ser Asp Ser Val Thr Ile Phe Arg Ser Arg Pro Val Ile Asn Ile Gln
            435                 440                 445
Lys Thr Ile Thr Val Thr Pro Asn Arg Ile Asp Leu Arg Gln Lys Thr
450                 455                 460
Ala Cys Gly Ala Pro Ser Gly Ile Cys Leu Gln Val Lys Ser Cys Phe
465                 470                 475                 480
Glu Tyr Thr Ala Asn Pro Ala Gly Tyr Asn Pro Ser Ile Ser Ile Val
                485                 490                 495
```

```
Gly Thr Leu Glu Ala Glu Lys Glu Arg Arg Lys Ser Gly Leu Ser Ser
            500                 505                 510

Arg Val Gln Phe Arg Asn Gln Ser Glu Pro Lys Tyr Thr Gln Glu
        515                 520                 525

Leu Thr Leu Lys Arg Gln Lys Gln Lys Val Cys Met Glu Glu Thr Leu
    530                 535                 540

Trp Leu Gln Asp Asn Ile Arg Asp Lys Leu Arg Pro Ile Pro Ile Thr
545                 550                 555                 560

Ala Ser Val Glu Ile Gln Glu Pro Ser Ser Arg Arg Val Asn Ser
        565                 570                 575

Leu Pro Glu Val Leu Pro Ile Leu Asn Ser Asp Glu Pro Lys Thr Ala
            580                 585                 590

His Ile Asp Val His Phe Leu Lys Glu Gly Cys Gly Asp Asp Asn Val
            595                 600                 605

Cys Asn Ser Asn Leu Lys Leu Glu Tyr Lys Gly Ser Leu Glu Asn Leu
            610                 615                 620

Tyr Phe Gln
625

<210> SEQ ID NO 79
<211> LENGTH: 454
<212> TYPE: PRT
<213> ORGANISM: Artificial Sequence
<220> FEATURE:
<223> OTHER INFORMATION: Artificial Sequence Integrin 1

<400> SEQUENCE: 79

Gln Thr Asp Glu Asn Arg Cys Leu Lys Ala Asn Ala Lys Ser Cys Gly
1               5                   10                  15

Glu Cys Ile Gln Ala Gly Pro Asn Cys Gly Trp Cys Thr Asn Ser Thr
            20                  25                  30

Phe Leu Gln Glu Gly Met Pro Thr Ser Ala Arg Cys Asp Asp Leu Glu
        35                  40                  45

Ala Leu Lys Lys Lys Gly Cys Pro Pro Asp Asp Ile Glu Asn Pro Arg
    50                  55                  60

Gly Ser Lys Asp Ile Lys Lys Asn Lys Asn Val Thr Asn Arg Ser Lys
65                  70                  75                  80

Gly Thr Ala Glu Lys Leu Lys Pro Glu Asp Ile Thr Gln Ile Gln Pro
                85                  90                  95

Gln Gln Leu Val Leu Arg Leu Arg Ser Gly Glu Pro Gln Thr Phe Thr
            100                 105                 110

Leu Lys Phe Lys Arg Ala Glu Asp Tyr Pro Ile Asp Leu Tyr Tyr Leu
        115                 120                 125

Met Asp Leu Ser Tyr Ser Met Lys Asp Asp Leu Glu Asn Val Lys Ser
    130                 135                 140

Leu Gly Thr Asp Leu Met Asn Glu Met Arg Arg Ile Thr Ser Asp Phe
145                 150                 155                 160

Arg Ile Gly Phe Gly Ser Phe Val Glu Lys Thr Val Met Pro Tyr Ile
                165                 170                 175

Ser Thr Thr Pro Ala Lys Leu Arg Asn Pro Cys Thr Ser Glu Gln Asn
            180                 185                 190

Cys Thr Ser Pro Phe Ser Tyr Lys Asn Val Leu Ser Leu Thr Asn Lys
        195                 200                 205

Gly Glu Val Phe Asn Glu Leu Val Gly Lys Gln Arg Ile Ser Gly Asn
    210                 215                 220
```

```
Leu Asp Ser Pro Glu Gly Gly Phe Asp Ala Ile Met Gln Val Ala Val
225                 230                 235                 240

Cys Gly Ser Leu Ile Gly Trp Arg Asn Val Thr Arg Leu Leu Val Phe
            245                 250                 255

Ser Thr Asp Ala Gly Phe His Phe Ala Gly Asp Gly Lys Leu Gly Gly
        260                 265                 270

Ile Val Leu Pro Asn Asp Gly Gln Cys His Leu Glu Asn Asn Met Tyr
        275                 280                 285

Thr Met Ser His Tyr Tyr Asp Tyr Pro Ser Ile Ala His Leu Val Gln
    290                 295                 300

Lys Leu Ser Glu Asn Asn Ile Gln Thr Ile Phe Ala Val Thr Glu Glu
305                 310                 315                 320

Phe Gln Pro Val Tyr Lys Glu Leu Lys Asn Leu Ile Pro Lys Ser Ala
                325                 330                 335

Val Gly Thr Leu Ser Ala Asn Ser Ser Asn Val Ile Gln Leu Ile Ile
            340                 345                 350

Asp Ala Tyr Asn Ser Leu Ser Ser Glu Val Ile Leu Glu Asn Gly Lys
        355                 360                 365

Leu Ser Glu Gly Val Thr Ile Ser Tyr Lys Ser Tyr Cys Lys Asn Gly
370                 375                 380

Val Asn Gly Thr Gly Glu Asn Gly Arg Lys Cys Ser Asn Ile Ser Ile
385                 390                 395                 400

Gly Asp Glu Val Gln Phe Glu Ile Ser Ile Thr Ser Asn Lys Cys Pro
                405                 410                 415

Lys Lys Asp Ser Asp Ser Phe Lys Ile Arg Pro Leu Gly Phe Thr Glu
            420                 425                 430

Glu Val Glu Val Ile Leu Gln Tyr Ile Cys Glu Cys Glu Gly Gly Leu
        435                 440                 445

Glu Asn Leu Tyr Phe Gln
    450

<210> SEQ ID NO 80
<211> LENGTH: 350
<212> TYPE: PRT
<213> ORGANISM: Artificial Sequence
<220> FEATURE:
<223> OTHER INFORMATION: Artificial Sequence HGF

<400> SEQUENCE: 80

Ser Gly Gln Asp Cys Tyr Arg Gly Asn Gly Lys Asn Tyr Met Gly Gln
1               5                   10                  15

Leu Ser Gln Thr Arg Ser Gly Leu Thr Cys Ser Met Trp Asp Lys Asn
            20                  25                  30

Met Glu Asp Leu His Arg His Ile Phe Trp Glu Pro Asp Ala Ser Lys
        35                  40                  45

Leu Asn Glu Asn Tyr Cys Arg Asn Pro Asp Asp Asp Ala His Gly Pro
    50                  55                  60

Trp Cys Tyr Thr Gly Asn Pro Leu Ile Pro Trp Asp Tyr Cys Pro Ile
65                  70                  75                  80

Ser Arg Cys Glu Gly Asp Thr Thr Pro Gly Ile Val Asn Leu Asp His
                85                  90                  95

Pro Val Ile Ser Cys Ala Lys Thr Ile Glu Gly Arg Val Val Asn Gly
            100                 105                 110

Ile Pro Thr Arg Thr Asn Ile Gly Trp Met Val Ser Leu Arg Tyr Arg
        115                 120                 125
```

```
Asn Lys His Ile Cys Gly Gly Ser Leu Ile Lys Glu Ser Trp Val Leu
        130                 135                 140

Thr Ala Arg Gln Cys Phe Pro Ser Arg Asp Leu Lys Asp Tyr Glu Ala
145                 150                 155                 160

Trp Leu Gly Ile His Asp Val His Gly Arg Gly Asp Glu Lys Cys Lys
                165                 170                 175

Gln Val Leu Gln Val Ser Gln Leu Val Tyr Gly Pro Glu Gly Ser Asp
                180                 185                 190

Leu Val Leu Met Lys Leu Ala Arg Pro Ala Val Leu Asp Asp Phe Val
        195                 200                 205

Ser Thr Ile Asp Leu Pro Asn Tyr Gly Cys Thr Ile Pro Glu Lys Thr
        210                 215                 220

Ser Cys Ser Val Tyr Gly Trp Gly Tyr Thr Gly Leu Ile Asn Tyr Asp
225                 230                 235                 240

Gly Leu Leu Arg Val Ala His Leu Tyr Ile Met Gly Asn Glu Lys Cys
                245                 250                 255

Ser Gln His His Arg Gly Lys Val Thr Leu Gln Glu Ser Glu Ile Cys
                260                 265                 270

Ala Gly Ala Glu Lys Ile Gly Ser Gly Pro Cys Glu Gly Asp Tyr Gly
        275                 280                 285

Gly Pro Leu Val Cys Glu Gln His Lys Met Arg Met Val Leu Gly Val
        290                 295                 300

Ile Val Pro Gly Arg Gly Cys Ala Ile Pro Asn Arg Pro Gly Ile Phe
305                 310                 315                 320

Val Arg Val Ala Tyr Tyr Ala Lys Trp Ile His Lys Ile Ile Leu Thr
                325                 330                 335

Tyr Lys Val Pro Gln Ser Arg Leu Glu Asn Leu Tyr Phe Gln
        340                 345                 350

<210> SEQ ID NO 81
<211> LENGTH: 197
<212> TYPE: PRT
<213> ORGANISM: Artificial Sequence
<220> FEATURE:
<223> OTHER INFORMATION: Artificial Sequence T4L Protein

<400> SEQUENCE: 81

Met Gly Glu Gln Lys Leu Ile Ser Glu Glu Asp Leu Arg Glu Asn Leu
1               5                   10                  15

Tyr Phe Gln Gly Lys Asp Gly Ser Gly His Lys Asn Ile Phe Glu Met
                20                  25                  30

Leu Arg Ile Asp Glu Gly Leu Arg Leu Lys Ile Tyr Lys Asp Thr Glu
        35                  40                  45

Gly Tyr Tyr Thr Ile Gly Ile Gly His Leu Leu Thr Lys Ser Pro Ser
    50                  55                  60

Leu Asn Ala Ala Lys Ser Glu Leu Asp Lys Ala Ile Gly Arg Asn Thr
65                  70                  75                  80

Asn Gly Val Ile Thr Lys Asp Glu Ala Glu Lys Leu Phe Asn Gln Asp
                85                  90                  95

Val Asp Ala Ala Val Arg Gly Ile Leu Arg Asn Ala Lys Leu Lys Pro
            100                 105                 110

Val Tyr Asp Ser Leu Asp Ala Val Arg Arg Ala Ala Leu Ile Asn Met
        115                 120                 125

Val Phe Gln Met Gly Glu Thr Gly Val Ala Gly Phe Thr Asn Ser Leu
    130                 135                 140
```

-continued

```
Arg Met Leu Gln Gln Lys Arg Trp Asp Glu Ala Ala Val Asn Leu Ala
145                 150                 155                 160

Lys Ser Arg Trp Tyr Asn Gln Thr Pro Asn Arg Ala Lys Arg Val Ile
                165                 170                 175

Thr Thr Phe Arg Thr Gly Thr Trp Asp Ala Tyr Leu Glu His His His
            180                 185                 190

His His His His His
        195

<210> SEQ ID NO 82
<211> LENGTH: 196
<212> TYPE: PRT
<213> ORGANISM: Artificial Sequence
<220> FEATURE:
<223> OTHER INFORMATION: Artificial Sequence T4L Protein

<400> SEQUENCE: 82

Met Gly Tyr Pro Tyr Asp Val Pro Asp Tyr Ala Arg Glu Asn Leu Tyr
1               5                   10                  15

Phe Gln Gly Lys Asp Gly Ser Gly His Lys Asn Ile Phe Glu Met Leu
            20                  25                  30

Arg Ile Asp Glu Gly Leu Arg Leu Lys Ile Tyr Lys Asp Thr Glu Gly
        35                  40                  45

Tyr Tyr Thr Ile Gly Ile Gly His Leu Leu Thr Lys Ser Pro Ser Leu
50                  55                  60

Asn Ala Ala Lys Ser Glu Leu Asp Lys Ala Ile Gly Arg Asn Thr Asn
65                  70                  75                  80

Gly Val Ile Thr Lys Asp Glu Ala Glu Lys Leu Phe Asn Gln Asp Val
                85                  90                  95

Asp Ala Ala Val Arg Gly Ile Leu Arg Asn Ala Lys Leu Lys Pro Val
            100                 105                 110

Tyr Asp Ser Leu Asp Ala Val Arg Arg Ala Ala Leu Ile Asn Met Val
        115                 120                 125

Phe Gln Met Gly Glu Thr Gly Val Ala Gly Phe Thr Asn Ser Leu Arg
    130                 135                 140

Met Leu Gln Gln Lys Arg Trp Asp Glu Ala Ala Val Asn Leu Ala Lys
145                 150                 155                 160

Ser Arg Trp Tyr Asn Gln Thr Pro Asn Arg Ala Lys Arg Val Ile Thr
                165                 170                 175

Thr Phe Arg Thr Gly Thr Trp Asp Ala Tyr Leu Glu His His His His
            180                 185                 190

His His His His
        195

<210> SEQ ID NO 83
<211> LENGTH: 14
<212> TYPE: PRT
<213> ORGANISM: Artificial Sequence
<220> FEATURE:
<223> OTHER INFORMATION: Artificial Sequence PA Peptide

<400> SEQUENCE: 83

Glu Gly Gly Val Ala Met Pro Gly Ala Glu Asp Asp Val Val
1               5                   10

<210> SEQ ID NO 84
<211> LENGTH: 271
<212> TYPE: PRT
```

<213> ORGANISM: Artificial Sequence
<220> FEATURE:
<223> OTHER INFORMATION: Artificial Sequence for producing scFv of NZ-1 Antibody

<400> SEQUENCE: 84

Met Lys Glu Val Gln Leu Val Glu Ser Gly Gly Gly Leu Val Gln Pro
1               5                   10                  15

Gly Arg Ser Leu Lys Leu Ser Cys Ala Ala Ser Gly Phe Thr Phe Ser
            20                  25                  30

Asn Tyr Gly Met Ala Trp Val Arg Gln Thr Pro Thr Lys Gly Leu Glu
        35                  40                  45

Trp Ile Ala Ser Ile Ser Ala Gly Gly Asp Lys Thr Tyr Tyr Gly Asp
    50                  55                  60

Ser Val Lys Gly Arg Phe Ser Ile Ser Arg Asp Asn Ala Lys Thr Thr
65                  70                  75                  80

His Tyr Leu Gln Met Asp Ser Leu Arg Ser Glu Asp Thr Ala Thr Tyr
                85                  90                  95

Tyr Cys Ala Lys Thr Ser Arg Val Tyr Phe Asp Tyr Trp Gly Gln Gly
            100                 105                 110

Val Met Val Thr Val Ser Ser Gly Gly Gly Ser Gly Gly Gly Gly
        115                 120                 125

Ser Gly Gly Gly Gly Ser Thr Gln Phe Val Leu Thr Gln Pro Asn Ser
130                 135                 140

Val Ser Thr Asn Leu Gly Ser Thr Val Lys Leu Ser Cys Lys Arg Ser
145                 150                 155                 160

Thr Gly Asn Ile Gly Ser Asn Tyr Val Asn Trp Tyr Gln Gln His Glu
                165                 170                 175

Gly Arg Ser Pro Thr Thr Met Ile Tyr Arg Asp Asp Lys Arg Pro Asp
            180                 185                 190

Gly Val Pro Asp Arg Phe Ser Gly Ser Ile Asp Arg Ser Ser Asn Ser
        195                 200                 205

Ala Leu Leu Thr Ile Asn Asn Val Gln Thr Glu Asp Glu Ala Asp Tyr
    210                 215                 220

Phe Cys His Ser Tyr Ser Ser Gly Ile Val Phe Gly Gly Gly Thr Lys
225                 230                 235                 240

Leu Thr Val Leu Gly Ala Ala Ala His His His His His Gly Ala
                245                 250                 255

Ala Glu Gln Lys Leu Ile Ser Glu Glu Asp Leu Asn Gly Ala Ala
            260                 265                 270

<210> SEQ ID NO 85
<211> LENGTH: 170
<212> TYPE: PRT
<213> ORGANISM: Artificial Sequence
<220> FEATURE:
<223> OTHER INFORMATION: Artificial Sequence VH-SARAH(Y35C) of NZ-1 Antibody

<400> SEQUENCE: 85

Met Lys Glu Val Gln Leu Val Glu Ser Gly Gly Gly Leu Val Gln Pro
1               5                   10                  15

Gly Arg Ser Leu Lys Leu Ser Cys Ala Ala Ser Gly Phe Thr Phe Ser
            20                  25                  30

Asn Tyr Gly Met Ala Trp Val Arg Gln Thr Pro Thr Lys Gly Leu Glu
        35                  40                  45

Trp Ile Ala Ser Ile Ser Ala Gly Gly Asp Lys Thr Tyr Tyr Gly Asp

-continued

```
                50                  55                  60

Ser Val Lys Gly Arg Phe Ser Ile Ser Arg Asp Asn Ala Lys Thr Thr
 65                  70                  75                  80

His Tyr Leu Gln Met Asp Ser Leu Arg Ser Glu Asp Thr Ala Thr Tyr
                 85                  90                  95

Tyr Cys Ala Lys Thr Ser Arg Val Tyr Phe Asp Tyr Trp Gly Gln Gly
                100                 105                 110

Val Met Val Thr Val Ser Ser Gly Ser Asp Tyr Glu Phe Leu Lys Ser
                115                 120                 125

Trp Thr Val Glu Asp Leu Gln Lys Arg Leu Leu Ala Leu Asp Pro Met
                130                 135                 140

Met Glu Gln Glu Ile Glu Ile Arg Gln Lys Cys Gln Ser Lys Arg
145                 150                 155                 160

Gln Pro Ile Leu Asp Ala Ile Glu Ala Lys
                165                 170

<210> SEQ ID NO 86
<211> LENGTH: 162
<212> TYPE: PRT
<213> ORGANISM: Artificial Sequence
<220> FEATURE:
<223> OTHER INFORMATION: Artificial Sequence VL-SARAH(M24C) of NZ-1
      Antibody

<400> SEQUENCE: 86

Met Gln Phe Val Leu Thr Gln Pro Asn Ser Val Ser Thr Asn Leu Gly
  1               5                  10                  15

Ser Thr Val Lys Leu Ser Cys Lys Arg Ser Thr Gly Asn Ile Gly Ser
                 20                  25                  30

Asn Tyr Val Asn Trp Tyr Gln Gln His Glu Gly Arg Ser Pro Thr Thr
                 35                  40                  45

Met Ile Tyr Arg Asp Asp Lys Arg Pro Asp Gly Val Pro Asp Arg Phe
                 50                  55                  60

Ser Gly Ser Ile Asp Arg Ser Ser Asn Ser Ala Leu Leu Thr Ile Asn
 65                  70                  75                  80

Asn Val Gln Thr Glu Asp Glu Ala Asp Tyr Phe Cys His Ser Tyr Ser
                 85                  90                  95

Ser Gly Ile Val Phe Gly Gly Gly Thr Lys Leu Thr Val Leu Gly Gly
                100                 105                 110

Ser Asp Tyr Glu Phe Leu Lys Ser Trp Thr Val Glu Asp Leu Gln Lys
                115                 120                 125

Arg Leu Leu Ala Leu Asp Pro Met Cys Glu Gln Glu Ile Glu Glu Ile
                130                 135                 140

Arg Gln Lys Tyr Gln Ser Lys Arg Gln Pro Ile Leu Asp Ala Ile Glu
145                 150                 155                 160

Ala Lys

<210> SEQ ID NO 87
<211> LENGTH: 170
<212> TYPE: PRT
<213> ORGANISM: Artificial Sequence
<220> FEATURE:
<223> OTHER INFORMATION: Artificial Sequence H-SARAH(Y35C) of SG/19
      Antibody

<400> SEQUENCE: 87

Met Gln Val His Leu Gln Gln Ser Gly Ala Glu Leu Met Lys Pro Gly
  1               5                  10                  15
```

Ala Ser Val Lys Ile Ser Cys Lys Ala Thr Gly Tyr Thr Phe Thr Ser
            20                  25                  30

Tyr Trp Ile Glu Trp Val Lys Gln Arg Pro Gly His Gly Leu Glu Trp
            35                  40                  45

Leu Gly Glu Ile Leu Pro Gly Ser Gly Tyr Ile His Tyr Asn Glu Lys
    50                  55                  60

Phe Lys Gly Lys Ala Thr Phe Thr Thr Asp Thr Ser Ser Asn Thr Ala
65                  70                  75                  80

Tyr Met Gln Leu Ser Ser Leu Thr Ser Glu Asp Ser Ala Val Tyr Tyr
                85                  90                  95

Cys Ser Arg Ala Leu Ala Leu Tyr Ala Met Asp Tyr Trp Gly Gln Gly
            100                 105                 110

Thr Ser Val Thr Val Ser Ser Gly Ser Asp Tyr Glu Phe Leu Lys Ser
            115                 120                 125

Trp Thr Val Glu Asp Leu Gln Lys Arg Leu Leu Ala Leu Asp Pro Met
    130                 135                 140

Met Glu Gln Glu Ile Glu Gln Ile Arg Gln Lys Cys Gln Ser Lys Arg
145                 150                 155                 160

Gln Pro Ile Leu Asp Ala Ile Glu Ala Lys
                165                 170

<210> SEQ ID NO 88
<211> LENGTH: 166
<212> TYPE: PRT
<213> ORGANISM: Artificial Sequence
<220> FEATURE:
<223> OTHER INFORMATION: Artificial Sequence VL-SARAH(M24C) of SG/19
      Antibody

<400> SEQUENCE: 88

Met Asp Ile Glu Leu Thr Gln Ser Pro Ser Ser Leu Thr Val Thr Ala
1               5                   10                  15

Gly Glu Lys Val Thr Met Ser Cys Lys Ser Ser Gln Ser Leu Leu Asn
            20                  25                  30

Ser Gly Asn Gln Lys Asn Tyr Leu Thr Trp Tyr Gln Gln Lys Pro Gly
            35                  40                  45

Gln Pro Pro Lys Leu Leu Ile Tyr Trp Ala Ser Thr Arg Glu Ser Gly
    50                  55                  60

Val Pro Asp Arg Phe Thr Gly Ser Gly Ser Gly Arg Asp Phe Thr Leu
65                  70                  75                  80

Thr Ile Ser Ser Val Gln Ala Glu Asp Leu Ala Val Tyr Tyr Cys Gln
                85                  90                  95

Asn Asp Asn Ser His Pro Leu Thr Phe Gly Ala Gly Thr Lys Leu Glu
            100                 105                 110

Leu Lys Ala Gly Ser Asp Tyr Glu Phe Leu Lys Ser Trp Thr Val Glu
            115                 120                 125

Asp Leu Gln Lys Arg Leu Leu Ala Leu Asp Pro Met Cys Glu Gln Glu
            130                 135                 140

Ile Glu Glu Ile Arg Gln Lys Tyr Gln Ser Lys Arg Gln Pro Ile Leu
145                 150                 155                 160

Asp Ala Ile Glu Ala Lys
                165

<210> SEQ ID NO 89
<211> LENGTH: 11
<212> TYPE: PRT

```
<213> ORGANISM: Artificial Sequence
<220> FEATURE:
<223> OTHER INFORMATION: Artificial Sequence eTEV Peptide

<400> SEQUENCE: 89

Arg Glu Asn Leu Tyr Phe Gln Gly Lys Asp Gly
1               5                   10
```

FRAGMENT ANTIBODY AND METHOD FOR CRYSTALLIZING PROTEIN USING FRAGMENT ANTIBODY

CROSS-REFERENCE TO RELATED APPLICATIONS

This patent application is the U.S. national phase of International Patent Application No. PCT/JP2017/040138, filed Nov. 7, 2017, which claims the benefit of Japanese Patent Application No. 2016-218631, filed on Nov. 9, 2016, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 115,141 bytes ASCII (Text) file named "742413Sequence-Listing.txt," created Apr. 26, 2019.

TECHNICAL FIELD

The present invention relates to a fragment antibody and a method for crystallizing a protein using the fragment antibody.

BACKGROUND ART

Antibody molecules, including IgG, are now indispensable tools in the fields of research, treatment, and diagnosis due to their binding properties to antigen molecules. In general, antibody molecules are multi-domain glycoproteins having a large molecular weight, and there are a plurality of disulfide bonds (hereinafter, sometimes simply referred to as S—S bonds) in the molecule, so it is necessary to express the proteins using animal cells. Production of proteins using animal cells, however, is generally more expensive than production using bacteria, and recombinant antibody molecules often have poor expression, so there is a problem of low productivity.

In order to supplement for the foregoing problems in the production of antibody molecules, use of a fragment antibody having a small molecular weight has been devised. Fragment antibodies have merits such as high tissue invasiveness.

A representative fragment antibody may be, for example, Fab consisting of variable domains (VH region and VL region) and constant domains (CH1 region and CL region). However, there is a problem of high production costs since Fab is generally obtained by purifying a full-length antibody, subjecting the purified full-length antibody to an enzymatic treatment, and subjecting the enzymatically treated antibody to further purification. In addition, a single-chain Fv (hereinafter, sometimes simply referred to as scFv) in which a C-terminus of the VH region or VL region and the other N-terminus are linked by a long and flexible peptide linker is known as another fragment antibody (Non-Patent Literature 1). However, aggregation of scFvs sometimes occurred due to the presence of the long and flexible peptide linker. In addition, there was also a problem that the activity as an antibody is lowered or destabilized.

Then, in order to solve the problems of the conventional fragment antibodies, the present inventors have developed a novel fragment antibody (hereinafter, sometimes simply referred to as Fv-clasp first generation or Fv-clasp (v1)) in which the C-termini of the VH region and VL region are linked through a dimer of SARAH domains of human mammalian sterile 20-like kinase 1 (Mst1) which forms an antiparallel coiled coil (Non-Patent Literature 2).

This Fv-clasp (v1) is a fragment antibody consisting of a complex of (a) a peptide in which the N-terminus of the SARAH domain of human Mst1 is linked to the C-terminus of a heavy chain domain (VH region) of the antibody and in which an amino acid residue at position 35 from the N-terminus of the SARAH domain of the human Mst1 is mutated to cysteine, and (b) a peptide in which the N-terminus of the SARAH domain of human Mst1 is linked to the C-terminus of a light chain domain (VL region) of the antibody and in which an amino acid residue at position 24 from the N-terminus of the SARAH domain of the human Mst1 is mutated to cysteine, in which (c) two SARAH domains are linked by a disulfide bond between the mutated cysteines.

CITATION LIST

Non-Patent Literature

Non-Patent Literature 1: Robert E. Bird, 1988, Science, James S. Huston, 1988, PNAS Non-Patent Literature 2: Takao Arimori, Shiori Machida, Yuki Fujii, Yu Kitago, Junichi Takagi, Design and Structural Analysis of Novel Fragment Antibody Format "Fv-clasp", The 15th Annual Meeting of the Protein Science Society of Japan, Jun. 25, 2015

Non-Patent Literature 3: Chothia and Lesk, Canonical structures for the hypervariable regions of immunoglobulins, J. Mol. Biol., 196, pp. 901 to 917 (1987)

Non-Patent Literature 4: Al-Lazikani, B., Lesk, A. M. & Chothia, C. (1997). Standard conformations for the canonical structures of immunoglobulins. J. Mol. Biol. 273, pp. 927 to 948

SUMMARY OF INVENTION

Technical Problem

The present inventors have attempted expression and purification of Fv-clasp (v1) against a variety of target antigen molecules by gene recombination using animal cells or *Escherichia coli* (hereinafter, simply referred to as *E. coli*), crystallization of Fv-clasp (v1), and crystallization of a complex of Fv-clasp (v1) and target antigen molecule. As a result, the present inventors have found that there are cases where crystals of the complex of Fv-clasp (v1) and target antigen molecule cannot be obtained or only crystals with low resolution capability may be obtained, particularly in a case of Fv-clasp (v1) obtained in an *E. coli* expression system.

Therefore, an object of the present invention is to provide a fragment antibody which can be conveniently produced as one having an antigen-binding activity, and which has a greater ability to crystallize itself alone or as a complex with an antigen molecule than that of Fv-clasp (v1) even in a case where the fragment antibody is obtained in an *E. coli* expression system.

Solution to Problem

In order to solve the foregoing problems, the present inventors have conducted extensive studies on the crystallization of a complex of a fragment antibody and an antigen molecule, with respect to a plurality of the fragment antibodies consisting of a complex of (a) a peptide in which a mutation of cysteine has been introduced in the VH region in a peptide (hereinafter, sometimes simply referred to as VH-SARAH) in which the N-terminus of the SARAH domain of human Mst1 is linked to the C-terminus of the heavy chain domain (VH region) of an antibody and (b) a peptide in which a mutation of cysteine has been introduced in the SARAH domain in a peptide (hereinafter, sometimes simply referred to as VL-SARAH) in which the N-terminus of the SARAH domain of human Mst1 is linked to the C-terminus of the light chain domain (VL region) of the antibody.

As a result, the present inventors have found that, in a case of using a fragment antibody (hereinafter, sometimes simply referred to as Fv-clasp 2nd generation or Fv-clasp (v2)) consisting of a complex of (a) a peptide (hereinafter, sometimes simply referred to as VH(112C)-SARAH) in which the N-terminus of the SARAH domain is linked to the C-terminus of the heavy chain domain (VH region) of the antibody, and an amino acid residue of antibody residue 112 according to Chothia numbering scheme in the VH region is mutated to cysteine, and (b) a peptide (hereinafter, sometimes simply referred to as VL-SARAH(37C)) in which the N-terminus of the SARAH domain is linked to the C-terminus of the light chain domain (VL region) of the antibody, and an amino acid residue at position 13 from the C-terminus in the SARAH domain is mutated to cysteine, in which (c) the VH(112C)-SARAH and the VL-SARAH(37C) are linked by a disulfide bond between the two cysteines, even Fv-clasp (v2) obtained in an *E. coli* expression system has an ability to crystallize itself alone or as a complex of Fv-clasp (v2) and antigen molecule.

Further, the present inventors have also found in Fv-clasp (v2) that high-resolution crystals of a complex of Fv-clasp (v2) and antigen molecule can be obtained from the screening stage before optimization of crystallization conditions. In addition, the present inventors have also found that Fv-clasp (v2) acts as a fragment antibody for promoting protein crystallization, as the crystallization of crystallization-resistant protein is promoted. Further, the present inventors have also found that Fv-clasp (v2) has higher heat stability than Fv-clasp (v1) or scFv. The present invention has been completed based on these findings.

The present invention relates to a fragment antibody given below and a method for crystallizing a protein using the fragment antibody.

[1] A fragment antibody comprising a complex of:
(a) a peptide (VH(112C)-SARAH) in which an N-terminus of a SARAH domain is linked to a C-terminus of a heavy chain domain (VH region) of an antibody, and an amino acid residue of antibody residue 112 according to Chothia numbering scheme in the VH region is mutated to cysteine; and
(b) a peptide (VL-SARAH(37C)) in which an N-terminus of a SARAH domain is linked to a C-terminus of a light chain domain (VL region) of an antibody, and an amino acid residue at position 13 from the C-terminus in the SARAH domain is mutated to cysteine,
in which (c) the VH(112C)-SARAH and the VL-SARAH (37C) are linked by a disulfide bond between the two cysteines.w

[2] The fragment antibody according to [1], in which the SARAH domain in the VH(112C)-SARAH is any one selected from SEQ ID NOs: 1 to 8, and the SARAH domain in the VL-SARAH(37C) is represented by any one selected from SEQ ID NOs: 9 to 16.

[3] The fragment antibody according to [1], in which the SARAH domain in the VH(112C)-SARAH is represented by SEQ ID NOs: 1 or 2, and the SARAH domain in the VL-SARAH(37C) is represented by SEQ ID NOs: 9 or 10.

[4] A fragment antibody for promoting protein crystallization, the fragment antibody comprising a complex of:
(a) a peptide (VH(112C)-SARAH) in which an N-terminus of a SARAH domain is linked to a C-terminus of a heavy chain domain (VH region) of an antibody, and an amino acid residue of antibody residue 112 according to Chothia numbering scheme in the VH region is mutated to cysteine; and
(b) a peptide (VL-SARAH(37C)) in which an N-terminus of a SARAH domain is linked to a C-terminus of a light chain domain (VL region) of an antibody, and an amino acid residue at position 13 from the C-terminus in the SARAH domain is mutated to cysteine,
in which (c) the VH(112C)-SARAH and the VL-SARAH (37C) are linked by a disulfide bond between the two cysteines.

[5] The fragment antibody for promoting protein crystallization according to [4], in which the SARAH domain in the VH(112C)-SARAH is represented by any one selected from SEQ ID NOs: 1 to 8, and the SARAH domain in the VL-SARAH(37C) is represented by any one selected from SEQ ID NOs: 9 to 16.

[6] The fragment antibody for promoting protein crystallization according to [4], in which the SARAH domain in the VH(112C)-SARAH is represented by SEQ ID NOs: 1 or 2, and the SARAH domain in the VL-SARAH(37C) is represented by SEQ ID NOs: 9 or 10.

[7] A method for crystallizing a protein, using the fragment antibody according to any one of [1] to [3].

Advantageous Effects of Invention

[1] The fragment antibody of the present invention can be conveniently produced and has an antigen-binding activity.

[2] The fragment antibody of the present invention has a great ability to crystallize itself alone or as a complex with an antigen molecule even in a case where the fragment antibody is obtained in an *E. coli* expression system. As a result, the fragment antibody of the present invention makes it easy to carry out the three-dimensional structure analysis of an antigen-determining site which was difficult with conventional fragment antibodies and antibodies.

[3] Further, the fragment antibody of the present invention promotes crystallization of a complex with a protein, particularly a crystallization-resistant protein, and functions as a fragment antibody for promoting protein crystallization. In addition, according to the fragment antibody of the present invention, a crystal of a complex with a protein can be obtained with good reproducibility in a short period of time.

[4] The fragment antibody of the present invention is a fragment antibody having higher heat resistance and greater stability than conventional antibodies or fragment antibodies.

BRIEF DESCRIPTION OF DRAWINGS

FIG. 15 (A) and (B) are micrographs of crystals obtained for a complex of 93201 antibody-Fv-clasp (v2) and Vps10p in Example 15. FIG. 15(C) shows the result of X-ray crystallography of the complex of 93201 antibody-Fv-clasp (v2) and Vps10p carried out in Example 15.

FIG. 16 (A) and (B) are micrographs of crystals obtained for a complex of TS2/16 antibody-Fv-clasp (v2) and integrin α6β1 in Example 16. FIG. 16(C) shows the result of X-ray crystallography of the complex of TS2/16 antibody-Fv-clasp (v2) and integrin α6β1 carried out in Example 16.

FIG. 17(A) is a micrograph of crystals obtained for a complex of t1E4 antibody-Fv-clasp (v2) and HGF in Example 17. FIG. 17(B) shows the result of X-ray crystallography of the complex of t1E4 antibody-Fv-clasp (v2) and HGF carried out in Example 17.

DESCRIPTION OF EMBODIMENTS

Figure 1:
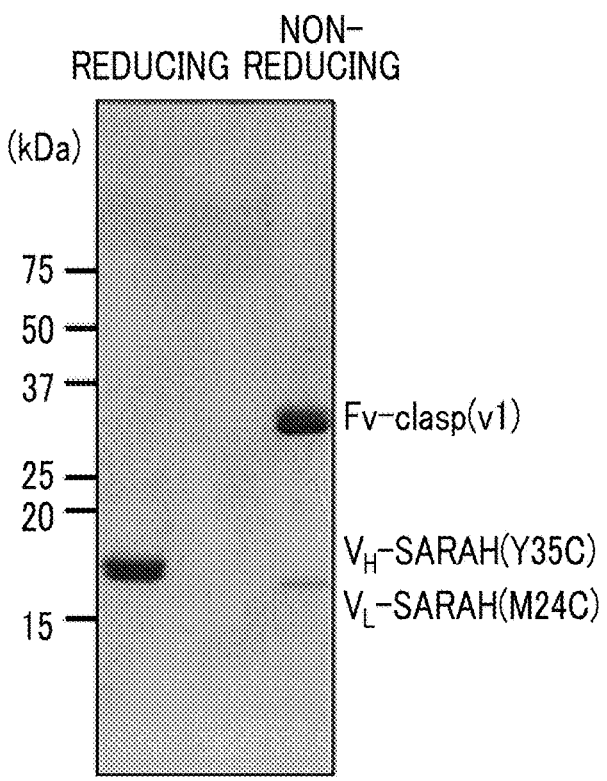
FIG. 1 is a view confirming that P20.1 antibody-Fv-clasp (v1) was obtained by SDS-PAGE in Comparative Example 1.

The fragment antibody according to the embodiment of the present invention is a fragment antibody including a complex of:

(a) a peptide (VH(112C)-SARAH) in which an N-terminus of a SARAH domain is linked to a C-terminus of a heavy chain domain (VH region) of an antibody, and an amino acid residue of antibody residue 112 according to Chothia numbering scheme in the VH region is mutated to cysteine; and (b) a peptide (VL-SARAH(37C)) in which an N-terminus of a SARAH domain is linked to a C-terminus of a light chain domain (VL region) of an antibody, and an amino acid residue at position 13 from the C-terminus in the SARAH domain is mutated to cysteine, in which (c) the VH(112C)-SARAH and the VL-SARAH(37C) are linked by a disulfide bond between the two cysteines.

It should be noted that, Non-Patent Literatures 3 and 4 are documents concerning a method of determining the antibody residue number by Chothia numbering scheme.

VH(112C)-SARAH

The SARAH domain is a domain (peptide) constituted of a short helix (h1) on the N-terminal side and a long helix (h2) on the C-terminal side, which consists of usually 42 to 54, preferably 43 to 49, more preferably 47 to 49, and particularly preferably 49 pieces of amino acid residues and has properties of forming antiparallel coiled coils between h2 with another SARAH domain. It should be noted that, h1 preferably consists of 5 to 7 pieces of amino acid residues, and h2 preferably consists of 38 to 42 pieces of amino acid residues.

The SARAH domain used here may be any SARAH domain as long as it has the properties as described above. Particularly, in a case where two SARAH domains form an antiparallel coiled coil between h2, the distance between both N-termini of two SARAH domains (two h1) is preferably 35 Å to 45 Å, more preferably 39 Å to 41 Å, and particularly preferably 40 Å.

Specific examples of such SARAH domains include SARAH domain of human mammalian sterile 20-like kinase 1 (Mst1), SARAH domain of human mammalian sterile 20-like kinase 2 (Mst2), SARAH domain of Hippo of *Drosophila*, SARAH domain of *Drosophila* RASSF, SARAH domain of human RASSF5, SARAH domain of human RASSF1, SARAH domain of human WW45, and SARAH domain of *Drosophila* Sav, and further include those having a sequence homology of usually 85% or more, preferably 90% or more, and more preferably 95% or more with one of the foregoing SARAH domains (preferably the SARAH domain of human Mst1).

More specifically, for example, one represented by SEQ ID NO: 1 (SARAH domain of Mst1), one represented by SEQ ID NO: 2 (SARAH domain of Mst2), one represented by SEQ ID NO: 3 (SARAH domain of Hippo), one represented by SEQ ID NO: 4 (SARAH domain of RASSF), one represented by SEQ ID NO: 5 (SARAH domain of RASSF5), one represented by SEQ ID NO: 6 (SARAH domain of RASSF1), one represented by SEQ ID NO: 7 (SARAH domain of WW45), or one represented by SEQ ID NO: 8 (SARAH domain of Sav) is preferable; one represented by SEQ ID NO: 1 or one represented by SEQ ID NO:

2 is more preferable; and one represented by SEQ ID NO: 1 is particularly preferable. It should be noted that, as long as it has the above-mentioned properties, the one represented by SEQ ID NOs: 1 to 8 may be one in which one or several amino acids in the sequence are deleted, substituted, or added. Here, several numbers represent natural numbers of 5 or less, preferably 3 or less, and more preferably 2 or less. Examples of such domains include those in which the amino acid residue at position 26 from the C-terminus is substituted with (is mutated to) cysteine in SEQ ID NOs: 1 to 8.

The SARAH domain may be a SARAH domain derived from a naturally occurring protein or may be artificially designed based on a SARAH domain derived from a naturally occurring protein.

In a case where the fragment antibody according to the embodiment of the present invention is used as a medicine, from the viewpoint of antigenicity, the SARAH domain derived from a naturally occurring protein is usually preferably derived from the same species of the organism as the animal to be administered in practical use, regardless of the species of the organism having the protein.

The VH region used here is a VH region having at least a site sufficient for recognizing a specific antigen to have a specific affinity binding property and having an amino acid residue of antibody residue 112 according to Chothia numbering scheme as cysteine.

It should be noted that the above-mentioned position of cysteine is a position determined by Chothia numbering scheme, but it contains the position defined by a method other than Chothia numbering scheme, for example, Kabat numbering scheme or IMGT numbering scheme, as long as it is at the same position as that of such an amino acid residue.

Specifically, the VH region of the present invention contains at least three CDRs 1 to 3 in the heavy chain of the antibody against the target antigen molecule and a framework region (FR)4 in which the amino acid residue of antibody residue 112, which is determined by Chothia numbering scheme, is cysteine; and preferably contains at least three CDRs 1 to 3 in the heavy chain of the antibody against the target antigen molecule, FRs 1 to 3, and FR4 in which the amino acid residue of antibody residue 112, which is determined by Chothia numbering scheme, is cysteine.

Above all, more preferred is a VII region which consists of the amino acid sequence of antibody residues 1 to 112 or the amino acid sequence of antibody residues 1 to 113 as determined by Chothia numbering scheme, and in which the amino acid residue of antibody residue 112 is cysteine; and particularly preferred is a VH region which consists of the amino acid sequence of antibody residues 1 to 113 as determined by Chothia numbering scheme and in which the amino acid residue of antibody residue 112 is cysteine.

It should be noted that CDRs 1 to 3 may be determined according to Chothia numbering scheme, the Kabat method, the IMGT method, or other methods, or by comprehensively taking these methods into consideration.

VH(112C)-SARAH according to the present invention is one in which the C-terminus of the VII region and the N-terminus of the SARAH domain are linked. The VH region and the SARAH domain may be directly linked or linked through a linker sequence, but it is preferable to link the VH region and the SARAH domain through a linker sequence from the viewpoint of high expression efficiency and refolding efficiency of VH(112C)-SARAH. The length of the linker sequence is usually 1 to 4 pieces of amino acid residues and preferably 2 pieces of amino acid residues. The linker sequence is not particularly limited as long as it does not adversely affect the properties of the fragment antibody according to the embodiment of the present invention, and examples thereof include Gly-Ser, Gly-Gly, and Ser-Ser.

Figure 18:
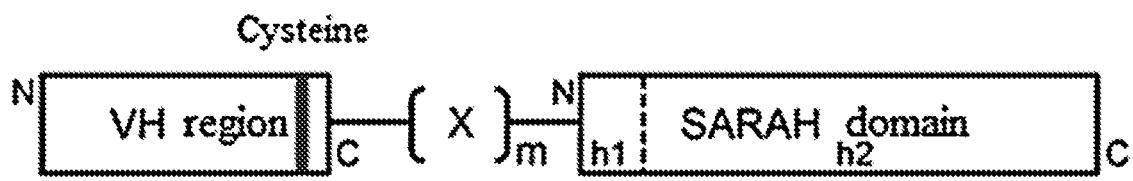
FIG. 18 is a schematic depiction of VH(112C)-SARAH (X represents an amino acid residue, m represents an integer of 0 to 4, and -[X]m- represents a linker sequence).

The VH(112C)-SARAH of the present invention is schematically shown in FIG. 18, where X represents an amino acid residue, m represents an integer of 0 to 4, and -[X]m- represents a linker sequence.

VL-SARAH(37C)

The SARAH domain used here is a domain (peptide) constituted of a short helix (h1) on the N-terminal side and a long helix (h2) on the C-terminal side, which consists of usually 42 to 54, preferably 43 to 49, more preferably 47 to 49, and particularly preferably 49 pieces of amino acid residues and has properties of forming antiparallel coiled coils between h2 with another SARAH domain, and in which the amino acid residue at position 13 from the C-terminus is cysteine. It should be noted that h1 preferably consists of 5 to 7 pieces of amino acid residues, and h2 preferably consists of 38 to 42 pieces of amino acid residues.

Particularly, in a case where two SARAH domains form an antiparallel coiled coil between h2, the distance between both N-termini of two SARAH domains (two h1) is preferably 35 Å to 45 Å, more preferably 39 Å to 41 Å, and particularly preferably 40 Å.

An example of such a SARAH domain is one in which the amino acid residue at position 13 from the C-terminus of the SARAH domain of the above-mentioned VH(112C)-SARAH of the present invention is substituted with (is mutated to) cysteine.

Specific examples of such SARAH domains include SARAH domain of human mammalian sterile 20-like kinase 1 (Mst1), SARAH domain of human mammalian sterile 20-like kinase 2 (Mst2), SARAH domain of Hippo of *Drosophila*, SARAH domain of *Drosophila* RASSF, SARAH domain of human RASSF5, SARAH domain of human RASSF1, SARAH domain of human WW45, and SARAH domain of *Drosophila* Say, and further include those which have a sequence homology of usually 85% or more, preferably 90% or more, and more preferably 95% or more with one of the foregoing SARAH domains (preferably SARAH domain of human Mst1) and in which the amino acid residue at position 13 from the C-terminus is substituted with (is mutated to) cysteine.

More specifically, for example, one represented by SEQ ID NO: 9 (one in which the amino acid residue at position 13 from the C-terminus of the SARAH domain of Mst1 is substituted with (is mutated to) cysteine), one represented by SEQ ID NO: 10 (one in which the amino acid residue at position 13 from the C-terminus of the SARAH domain of Mst2 is substituted with (is mutated to) cysteine), one represented by SEQ ID NO: 11 (one in which the amino acid residue at position 13 from the C-terminus of the SARAH domain of Hippo is substituted with (is mutated to) cysteine), one represented by SEQ ID NO: 12 (one in which the amino acid residue at position 13 from the C-terminus of the SARAH domain of RASSF is substituted with (is mutated to) cysteine), one represented by SEQ ID NO: 13 (one in which the amino acid residue at position 13 from the C-terminus of the SARAH domain of RASSF5 is substituted with (is mutated to) cysteine), one represented by SEQ ID NO: 14 (one in which the amino acid residue at position 13 from the C-terminus of the SARAH domain of RASSF1 is substituted with (is mutated to) cysteine), one represented by SEQ ID NO: 15 (one in which the amino acid residue at position 13 from the C-terminus of the SARAH domain of WW45 is substituted with (is mutated to) cysteine), or one represented by SEQ ID NO: 16 (one in which the amino acid residue at position 13 from the C-terminus of the SARAH domain of Say is substituted with (is mutated to) cysteine) is preferable; one represented by SEQ ID NO: 9 or one represented by SEQ ID NO: 10 is more preferable; and one represented by SEQ ID NO: 9 is particularly preferable. It should be noted that, as long as it has the above-mentioned properties, the one represented by SEQ ID NOs: 9 to 16 may be one in which one or several amino acids in the sequence are deleted, substituted, or added. Here, several numbers represent natural numbers of 5 or less, preferably 3 or less, and more preferably 2 or less. Examples of such domains include those in which the amino acid residue at position 26 from the C-terminus is substituted with (is mutated to) cysteine in SEQ ID NOs: 9 to 16.

In addition, the SARAH domain in VL-SARAH(37C) according to the present invention may be derived from the same SARAH domain as the SARAH domain in VH(112C)-SARAH according to the present invention or may be derived from a different SARAH domain. As long as it is easy to form an antiparallel coiled coil, its identity does not matter.

Specific preferred combinations of the SARAH domain in VH(112C)-SARAH according to the present invention and the SARAH domain in VL-SARAH(37C) according to the present invention include a combination of one represented by SEQ ID NO: 1 and one represented by SEQ ID NO: 13, a combination of one represented by SEQ ID NO: 5 and one represented by SEQ ID NO: 9, a combination of one represented by SEQ ID NO: 1 and one represented by SEQ ID NO: 9, a combination of one represented by SEQ ID NO: 2 and one represented by SEQ ID NO: 10, a combination of one represented by SEQ ID NO: 3 and one represented by SEQ ID NO: 11, a combination of one represented by SEQ ID NO: 4 and one represented by SEQ ID NO: 12, a combination of one represented by SEQ ID NO: 5 and one represented by SEQ ID NO: 13, a combination of one represented by SEQ ID NO: 6 and one represented by SEQ ID NO: 14, a combination of one represented by SEQ ID NO: 7 and one represented by SEQ ID NO: 15, and a combination of one represented by SEQ ID NO: 8 and one represented by SEQ ID NO: 16; among which more preferred is a combination of one represented by SEQ ID NO: 1 and one represented by SEQ ID NO: 9, a combination of one represented by SEQ ID NO: 2 and one represented by SEQ ID NO: 10, a combination of one represented by SEQ ID NO: 1 and one represented by SEQ ID NO: 13, or a combination of one represented by SEQ ID NO: 5 and one represented by SEQ ID NO: 9. The one represented by SEQ ID NOs: 1 to 16 may be one in which one or several amino acids in the sequence are deleted, substituted, or added. Here, several numbers represent natural numbers of 5 or less, preferably 3 or less, and more preferably 2 or less.

The SARAH domain in VL-SARAH(37C) according to the present invention may be a SARAH domain derived from a naturally occurring protein or may be artificially designed based on a SARAH domain derived from a naturally occurring protein.

In a case where the fragment antibody according to the embodiment of the present invention is used as a medicine, from the viewpoint of antigenicity, the SARAH domain derived from a naturally occurring protein is usually preferably derived from the same species of the organism as the animal to be administered in practical use, regardless of the species of the organism having the protein.

The VL region in the present invention may contain at least a site sufficient for recognizing an antigen in a specific region to have a specific affinity. The VL region in the present invention may be, for example, one containing at least three CDRs 1 to 3 in the light chain of the antibody against the target antigen molecule, and preferably one containing at least three CDRs 1 to 3 and FRs 1 to 4 in the light chain of the antibody against the target antigen molecule.

Above all, more preferred is a VL region which consists of the amino acid sequence of antibody residues 1 to 107 as determined by Chothia numbering scheme.

It should be noted that, CDRs 1 to 3 may be determined according to Chothia numbering scheme, the Kabat method, the IMGT method, or other methods, or by comprehensively taking these methods into consideration.

The VL-SARAH(37C) of the present invention is one in which the C-terminus of the VL region and the N-terminus of the SARAH domain are linked. The VL region and the SARAH domain may be directly linked or linked through a linker sequence, but it is preferable to link the VH region and the SARAH domain through a linker sequence from the viewpoint of high expression efficiency and refolding efficiency of VL-SARAH(37C). The length of the linker sequence is usually 1 to 4 pieces of amino acid residues and preferably 2 pieces of amino acid residues. The linker sequence is not particularly limited as long as it does not adversely affect the properties of the fragment antibody according to the embodiment of the present invention, and examples thereof include Gly-Ser, Gly-Gly, and Ser-Ser.

Figure 19:
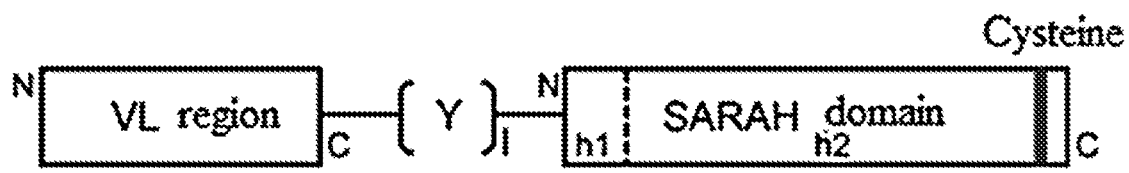
FIG. 19 is a schematic depiction of VL-SARAH(37C) (Y represents an amino acid residue, l represents an integer of 0 to 4, and -[Y]l- represents a linker sequence).

VL-SARAH(37C) according to the present invention is schematically shown in FIG. 19, where Y represents an amino acid residue, l represents an integer of 0 to 4, and -[Y]l- represents a linker sequence.

Fragment Antibody

The fragment antibody according to the embodiment of the present invention comprises a complex of VH(112C)-SARAH according to the present invention and VL-SARAH (37C) according to the present invention.

More specifically, h2 of the SARAH domain in VH(112C)-SARAH according to the present invention and h2 of the SARAH domain in VL-SARAH(37C) according to the present invention are linked by forming an antiparallel coiled coil, and the cysteine residue at antibody residue 112 according to Chothia numbering scheme in the VH region in VH(112C)-SARAH and the cysteine residue at position 13 from the C-terminus of the SARAH domain in VL-SARAH (37C) are linked by a disulfide bond.

Since the fragment antibody according to the embodiment of the present invention is linked by such a special linking mode, it not only has an antigen-binding activity but also has higher heat resistance and stability than Fv-clasp (v1), and exhibits a high ability to crystallize itself alone or as a complex with an antigen molecule than that of Fv-clasp (v1) even in a case where the fragment antibody is obtained in an *E. coli* expression system. As a result, the fragment antibody according to the embodiment of the present invention makes it easy to carry out the three-dimensional structure analysis of an antigen-determining site which was difficult with conventional fragment antibodies and antibodies.

Further, since the fragment antibody according to the embodiment of the present invention is linked by the special linking mode, it has a function of promoting crystallization of a complex with a protein, particularly a crystallization-resistant protein and is particularly useful as a fragment antibody for promoting protein crystallization.

Incidentally, the expression "high ability to crystallize" in the present specification means that it is possible to obtain a high-resolution crystal or/and to obtain more crystals in a so-called screening stage, in a case where the fragment antibody according to the embodiment of the present invention is used to crystallize itself alone or as a complex with an antigen molecule.

Figure 20:
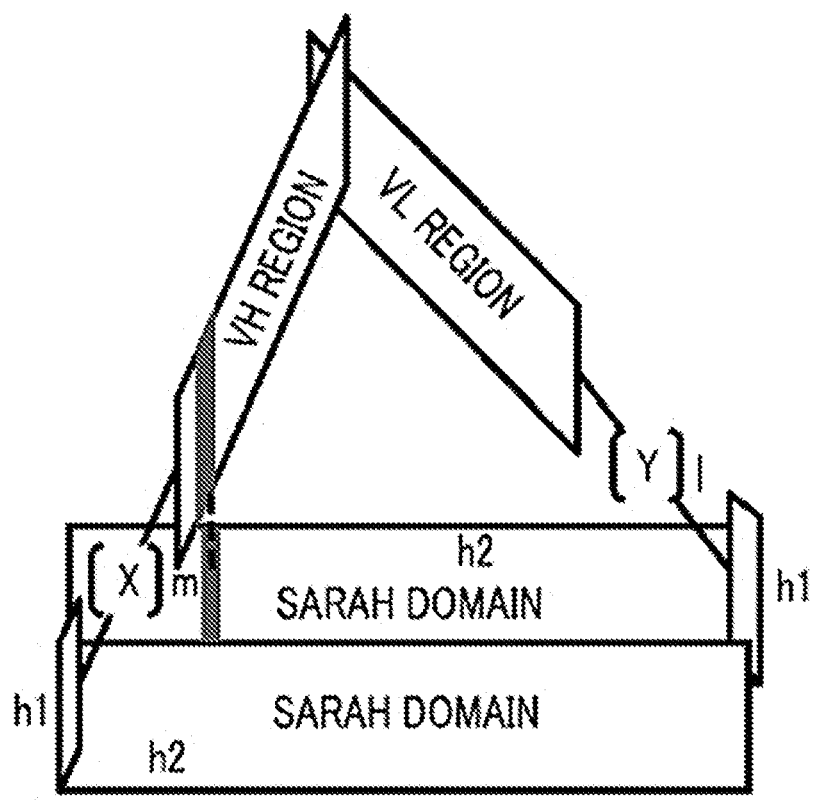
FIG. 20 is a schematic depiction of a fragment antibody according to an embodiment of the present invention (X and Y represent amino acid residues, and l and m represent integers of 0 to 4).

The fragment antibody according to the embodiment of the present invention is schematically shown in FIG. 20, where X, Y, 1, and m are the same as described above.

Method for Preparing Fragment Antibody of Present Invention

The fragment antibody according to the embodiment of the present invention can be produced by a general chemical production method according to its amino acid sequence. The fragment antibody according to the embodiment of the present invention can be obtained by a usual chemical production method (chemical synthesis method) such as a fluorenylmethyloxycarbonyl method (Fmoc method) or a t-butyloxycarbonyl method (tBoc method). In addition, the fragment antibody according to the embodiment of the present invention can be chemically synthesized using a commercially available peptide synthesizer.

Further, the fragment antibody according to the embodiment of the present invention can be obtained by a well-known method using a gene recombination technique of incorporating a nucleic acid molecule encoding the fragment antibody according to the embodiment of the present invention into an expression vector such as an appropriate plasmid or phage, transforming (or transducing) a host cell with a recombinant expression vector, amplifying the obtained host cell, and intracellularly or extracellularly secreting the gene product.

In a case where the fragment antibody according to the embodiment of the present invention is prepared by gene recombination technology, for example, a method of preparing according to the following steps can be mentioned.

(1) Gene recombination/expression step
(2) Purification step

If necessary, (1) after the gene recombination/expression step, a solubilization step, a refolding step, a concentration step, and the like may be carried out.

(1) Gene Recombination/Expression Step (1) The gene recombination/expression step is a step of transfecting a vector having a nucleic acid sequence encoding VH(112C)-SARAH according to the present invention (hereinafter, sometimes simply referred to as a recombinant vector for expression of VH(112C)-SARAH according to the present invention), or a vector having a nucleic acid sequence encoding VL-SARAH(37C) according to the present invention (hereinafter, sometimes simply referred to as a recombinant vector for expression of VL-SARAH(37C) according to the present invention) into a host, and culturing the transfected host to prepare a crude extract, a culture solution (culture supernatant) or a precipitate containing VH(112C)-SARAH according to the present invention, VL-SARAH(37C) according to the present invention, or the fragment antibody according to the embodiment of the present invention.

The nucleic acid sequence encoding VH(112C)-SARAH according to the present invention may have at least a nucleic acid sequence to which the 3' end of the nucleic acid sequence encoding the VH region in the VH(112C)-SARAH and the 5' end of the nucleic acid sequence encoding the SARAH domain are linked, and may contain a nucleic acid sequence or the like used for preparing a protein in the field of genetic engineering, such as a nucleic acid sequence encoding a start codon, a stop codon, a nucleic acid sequence encoding a linker sequence, or a sequence encoding a tag.

The nucleic acid sequence encoding the VH region in the VH(112C)-SARAH and the nucleic acid sequence encoding the SARAH domain may be linked directly or through a linker sequence, but it is preferable to link the VH region-encoding sequence and the SARAH domain-encoding sequence through a linker sequence from the viewpoint of high expression efficiency and refolding efficiency of VH(112C)-SARAH.

The length of the nucleic acid sequence encoding a linker sequence is usually 3 to 12 bases and preferably 6 bases. The nucleic acid sequence encoding a linker sequence is not particularly limited as long as it does not adversely affect VH(112C)-SARAH according to the present invention and the properties of the fragment antibody according to the embodiment of the present invention. Examples of the linker sequence-encoding sequence include a nucleic acid sequence encoding Gly-Ser, a nucleic acid sequence encoding Gly-Gly, and a nucleic acid sequence encoding Ser-Ser, among which a nucleic acid sequence encoding Gly-Ser is preferable.

The nucleic acid sequence encoding VL-SARAH(37C) according to the present invention may have at least a nucleic acid sequence to which the 3' end of the nucleic acid sequence encoding the VL region and the 5' end of the nucleic acid sequence encoding the SARAH domain in the VL-SARAH(37C) are linked, and may contain a nucleic acid sequence or the like used for preparing a protein in the field of genetic engineering, such as a nucleic acid sequence encoding a start codon, a stop codon, a nucleic acid sequence encoding a linker sequence, or a sequence encoding a tag.

The nucleic acid sequence encoding the VL region and the nucleic acid sequence encoding the SARAH domain in the VL-SARAH(37C) may be linked directly or through a linker sequence, but it is preferable to link the VL region-encoding sequence and the SARAH domain-encoding sequence through a linker sequence from the viewpoint of high expression efficiency and refolding efficiency of VL-SARAH(37C).

The length of the nucleic acid sequence encoding a linker sequence is usually 3 to 12 bases and preferably 6 bases. The nucleic acid sequence encoding a linker sequence is not particularly limited as long as it does not adversely affect VL-SARAH(37C) according to the present invention and the properties of the fragment antibody according to the embodiment of the present invention. Examples of the linker sequence-encoding sequence include a nucleic acid sequence encoding Gly-Ser, a nucleic acid sequence encoding Gly-Gly, and a nucleic acid sequence encoding Ser-Ser, among which a nucleic acid sequence encoding Gly-Ser is preferable.

The recombinant vector for expression of VH(112C)-SARAH according to the present invention or the recombinant vector for expression of VL-SARAH(37C) according to the present invention (hereinafter, the two recombinant vectors for expression together are sometimes simply referred to as the recombinant vector for expression according to the present invention) is a vector having a nucleic acid sequence encoding at least VH(112C)-SARAH according to the present invention, or a vector having a nucleic acid sequence encoding at least VL-SARAH(37C) according to the present invention, and is not particularly limited as long as it is a vector having a function of expressing and producing VH(112C)-SARAH according to the present invention or VL-SARAH(37C) according to the present invention in a host.

The recombinant vector for expression of VH(112C)-SARAH according to the present invention may be, for example, a vector in which a nucleic acid sequence encoding VH(112C)-SARAH according to the present invention such as SEQ ID NO: 41, SEQ ID NO: 45, SEQ ID NO: 46, SEQ ID NO: 47, SEQ ID NO: 48, SEQ ID NO: 49, SEQ ID NO: 50, SEQ ID NO: 51, or SEQ ID NO: 52 is incorporated into an expression vector such as pET16b vector (manufactured by Novagen, Inc.), pcDNA 3.1 vector (manufactured by Thermo Fisher Scientific Inc.), or pCAG-Neo vector (manufactured by Wako Pure Chemical Industries, Ltd.) according to a conventional cloning technique.

The recombinant vector for expression of VL-SARAH (37C) according to the present invention may be, for example, a vector in which a nucleic acid sequence encoding VH(112C)-SARAH according to the present invention such as SEQ ID NO: 42, SEQ ID NO: 53, SEQ ID NO: 54, SEQ ID NO: 55, SEQ ID NO: 56, SEQ ID NO: 57, SEQ ID NO: 58, SEQ ID NO: 59, or SEQ ID NO: 60 is incorporated into an expression vector such as pET16b vector (manufactured by Novagen, Inc.), pcDNA 3.1 vector (manufactured by Thermo Fisher Scientific Inc.), or pCAG-Neo vector (manufactured by Wako Pure Chemical Industries, Ltd.) according to a conventional cloning technique.

The method for preparing the recombinant vector for expression according to the present invention may be carried out according to a known method concerning a method for preparing a recombinant vector for expression by gene recombination and is not particularly limited, as long as it is a method by which a vector having a nucleic acid sequence encoding VH(112C)-SARAH according to the present invention or VL-SARAH(37C) according to the present invention is finally obtained.

For example, there is a method in which a nucleic acid sequence encoding VH(112C)-SARAH according to the present invention or a nucleic acid sequence encoding VL-SARAH(37C) according to the present invention is transfected into an expression vector.

With regard to transfection of the nucleic acid sequence encoding VH(112C)-SARAH according to the present invention or the nucleic acid sequence encoding VL-SARAH(37C) according to the present invention, the full length of the nucleic acid sequence may be transfected into the expression vector at once or may be transfected in multiple steps.

That is, the recombinant vector for expression according to the present invention may be obtained by further introducing the remaining partial sequence of the nucleic acid sequence encoding VH(112C)-SARAH according to the present invention or the remaining partial sequence of the nucleic acid sequence encoding VL-SARAH(37C) according to the present invention into a recombinant vector for expression into which a partial sequence of a nucleic acid sequence encoding VH(112C)-SARAH according to the present invention or a partial sequence of a nucleic acid sequence encoding VL-SARAH(37C) according to the present invention has previously been introduced.

A partial sequence of a nucleic acid sequence encoding VH(112C)-SARAH according to the present invention or a partial sequence of a nucleic acid sequence encoding VL-SARAH(37C) according to the present invention, and the remaining partial sequence of the nucleic acid sequence encoding VH(112C)-SARAH according to the present invention or the remaining partial sequence of the nucleic acid sequence encoding VL-SARAH(37C) according to the present invention may be divided at any point in the nucleic acid sequence encoding VH(112C)-SARAH according to the present invention or the nucleic acid sequence encoding VL-SARAH(37C) according to the present invention as a base, in a case where a vector having a function of expressing and producing VH(112C)-SARAH according to the present invention or VL-SARAH(37C) according to the present invention is finally obtained.

The combination of the partial sequence of the nucleic acid sequence encoding VH(112C)-SARAH according to the present invention and the remaining partial sequence of the nucleic acid sequence encoding VH(112C)-SARAH according to the present invention may be, for example, a combination of [a nucleic acid sequence encoding a VH region in VH(112C)-SARAH according to the present invention and a sequence encoding a SARAH domain in VH(112C)-SARAH according to the present invention]; a combination of [a sequence encoding a VH region and a linker in VH(112C)-SARAH according to the present invention and a nucleic acid sequence encoding a SARAH domain in VH(112C)-SARAH according to the present invention]; or a combination of [a nucleic acid sequence encoding a VH region in VH(112C)-SARAH according to the present invention and a sequence encoding a SARAH domain and a linker in VH(112C)-SARAH according to the present invention].

The combination of the partial sequence of the nucleic acid sequence encoding VL-SARAH(37C) according to the present invention and the remaining partial sequence of the nucleic acid sequence encoding VL-SARAH(37C) according to the present invention may be, for example, a combination of [a nucleic acid sequence encoding a VL region in VL-SARAH(37C) according to the present invention and a nucleic acid sequence encoding a SARAH domain in VL-SARAH(37C) according to the present invention]; a combination of [a nucleic acid sequence encoding a VL region in VL-SARAH(37C) according to the present invention and a nucleic acid sequence encoding a SARAH domain and a linker in VL-SARAH(37C) according to the present invention]; or a combination of [a nucleic acid sequence encoding a VL region and a linker in VL-SARAH(37C) according to the present invention and a nucleic acid sequence encoding a SARAH domain in VL-SARAH(37C) according to the present invention].

That is, in the preparation of the recombinant vector for expression according to the present invention, a vector having a partial sequence of the nucleic acid sequence encoding VH(112C)-SARAH according to the present invention or a partial sequence of the nucleic acid sequence encoding VL-SARAH(37C) according to the present invention (hereinafter, sometimes simply referred to as an intermediate vector) may be obtained. Examples of the intermediate vector include a vector having a nucleic acid sequence encoding a SARAH domain in VH(112C)-SARAH according to the present invention, a vector having a nucleic acid sequence encoding a SARAH domain and a linker in VH(112C)-SARAH according to the present invention, a vector having a nucleic acid sequence encoding a SARAH domain in VL-SARAH(37C) according to the present invention, and a vector having a nucleic acid sequence encoding a SARAH domain and a linker in VL-SARAH(37C) according to the present invention. These intermediate vectors may contain a restriction enzyme sequence such as NdeI or NcoI upstream of the nucleic acid sequence encoding a linker or the nucleic acid sequence encoding the SARAH domain in VH(112C)-SARAH according to the present invention.

Examples of the expression vector include a plasmid vector and a viral vector. Specific examples of the expression vector include plasmid vectors such as pET16b vector (manufactured by Novagen, Inc.), pET28b vector (manufactured by Novagen, Inc.), pcDNA3.1 vector (manufactured by Thermo Fisher Scientific Inc.), pCAG-Neo vector (manufactured by Wako Pure Chemical Industries, Ltd.), pTrcHis2 vector, pcDNA3.1/myc-His vector (manufactured by Invitrogen Corporation), pUC119 (manufactured by Takara Shuzo Co., Ltd.), Pqe-tri (manufactured by QIAGEN GmbH), pET, pGEX, and pMAL; and viral vectors such as pMEI-5 DNA (manufactured by Takara Shuzo Co., Ltd.) and pLVSI-CMV NEO Vector (manufactured by Takara Shuzo Co., Ltd.). In addition, pA1-11, pXT1, pRc/CMV, pRc/RSV, pcDNAI/Neo, p3×FLAG-CMV-14, pCAT3, pcDNA3.1, pCMV, and the like can be mentioned in addition to plasmids derived from E. coli (for example, pTrc99A, pKK223, and pET3a). Among them, pET16b vector (manufactured by Novagen, Inc.), pET28b vector (manufactured by Novagen, Inc.), and pcDNA3.1 vector (manufactured by Thermo Fisher Scientific Inc.) are preferred.

For example, in a case of preparing a recombinant vector for expression of VH(112C)-SARAH according to the present invention, a nucleic acid sequence encoding the SARAH domain in the nucleic acid sequence encoding VH(112C)-SARAH according to the present invention is introduced into the expression vector as described above, and if necessary, a nucleic acid sequence encoding a linker is introduced upstream of the nucleic acid sequence encoding the SARAH domain to obtain an intermediate vector. A recombinant vector for expression of VH(112C)-SARAH against a variety of antigen molecules can be easily prepared by introducing a nucleic acid sequence encoding the VH region in the nucleic acid sequence encoding VH(112C)-SARAH according to the present invention (for example, three CDRs 1 to 3, FRs 1 to 3 in the heavy chain of an antibody against a target antigen molecule, and FR4 in which the amino acid residue of antibody residue 112 as determined by Chothia numbering scheme is cysteine) upstream of the introduced nucleic acid sequence encoding the SARAH domain or the nucleic acid sequence encoding the linker, in the intermediate vector thus obtained.

More specifically, in a case where the expression vector (intermediate vector) as described above into which a linker nucleic acid sequence (for example, Gly-Ser) and a SARAH domain-encoding nucleic acid sequence have been introduced is prepared, a recombinant vector for expression of VH(112C)-SARAH against a variety of antigen molecules can be easily prepared by introducing a desired VH region portion (for example, three CDRs 1 to 3, FRs 1 to 3 in the heavy chain of an antibody against a target antigen molecule, and FR4 in which the amino acid residue of antibody residue 112 as determined by Chothia numbering scheme is cysteine) upstream of the linker nucleic acid sequence and the SARAH domain-encoding nucleic acid sequence of the expression vector.

It should be noted that, the recombinant vector for expression of VL-SARAH(37C) according to the present invention can be prepared in the same manner as the recombinant vector for expression of VH(112C)-SARAH according to the present invention.

VH(112C)-SARAH according to the present invention or/and VL-SARAH(37C) according to the present invention may be expressed as a fusion protein with a tag peptide or another protein. As the tag peptide to be fused, FLAG tag, 3×FLAG tag, His tag (for example, 6×His tag), or the like can be mentioned.

Subsequently, an appropriate host cell is transformed (transduced) using a recombinant vector for expression to prepare a transformant.

The host cell may be any host cell as long as it has a function of expressing and producing VH(112C)-SARAH according to the present invention or/and VL-SARAH(37C) according to the present invention. Examples of the host cell include a prokaryote such as E. coli or bacterium of the genus Bacillus (B. subtilis, B. brevis, or B. borstelenis), an animal cell, an insect cell, a plant cell, and a yeast cell, among which E. coli or an animal cell is preferable; E. coli or a mammalian cell is more preferable; and E. coli is particularly preferable. Examples of the mammalian cell include Expi293F cell, HEK293T cell, COS-7 cell, CHO-K1 cell, and CHO—S cell. Examples of E. coli include BL21 (DE3), K-12, DH1, DH5, DH5α, M15, HB101, C600, XL-1 Blue, JM109, JM105, JM127, XL1-Blue, VCS257, and TOP10.

In addition, a competent cell having higher efficiency of introducing plasmid or phage DNA may be used. Examples of the competent cell include E. coli DH5α competent cell and E. coli JM109 competent cell (manufactured by Takara Bio Inc.).

As described above, some Fv-clasp (v1) obtained in a case of using E. coli as a host cell (hereinafter, sometimes simply referred to as E. coli expression system) have no ability to crystallize as a complex with an antigen molecule. In addition, even in a case of having such an ability to crystallize, only a low-resolution crystal can be obtained in a so-called screening stage before optimization of crystallization conditions.

On the other hand, even in a case where the fragment antibody according to the embodiment of the present invention is prepared in an E. coli expression system, one having an ability to crystallize the fragment antibody according to the embodiment of the present invention alone or as a complex with a specific antigen can be obtained.

The recombinant vector for expression of VH(112C)-SARAH according to the present invention and the recombinant vector for expression of VL-SARAH(37C) according to the present invention may be either co-expressed or expressed in separate host cells. In addition, in a case where E. coli is used as a host cell, it is preferable to express them in separate host cells, and in a case where an animal cell is used as a host cell, it is preferable to co-express them.

It should be noted that, in a case of co-expression in an animal cell, it is expressed as the fragment antibody according to the embodiment of the present invention (complex of VH(112C)-SARAH according to the present invention and VL-SARAH(37C) according to the present invention), so a refolding step to be described later is unnecessary; whereas in a case of expression in separate host cells, it is necessary to carry out the refolding step to be described later after mixing the expressed VH(112C)-SARAH according to the present invention and the expressed VL-SARAH(37C) according to the present invention.

Transfection of the recombinant vector for expression of VH(112C)-SARAH according to the present invention or the recombinant vector for expression of VL-SARAH(37C) according to the present invention into a host cell may be carried out, for example, in accordance with a known method described in "Protein expression protocol that can be selected depending on each purpose, Chapter 3, Protein expression protocol, ISBN 978-4-7581-0175-2, Yodosha Co., Ltd.", or the like.

A transformant is then cultured in a nutrient medium to produce VH(112C)-SARAH according to the present invention or VL-SARAH(37C) according to the present invention. Culturing is carried out by a known method, and the temperature, the pH of the [culture] medium, and the culture time may be appropriately set.

In a case of culturing a transformant whose host cell is E. coli, the transformant may be cultured in a commonly used liquid medium under ordinary conditions of culturing E.

coli, and in a case of culturing a transformant whose host cell is an animal cell, the transformant may be cultured in a commonly used liquid medium under ordinary conditions of culturing an animal cell. In addition, if necessary, for example, an agent such as isopropyl-β-D-thiogalactopyranoside (IPTG) or 3β-indolylacrylic acid may be added.

A culture solution (culture supernatant) crude extract or precipitate containing VH(112C)-SARAH according to the present invention, VL-SARAH(37C) according to the present invention, or the fragment antibody according to the embodiment of the present invention can be obtained from the culture obtained by the above culturing as follows.

That is, in a case where VH(112C)-SARAH according to the present invention, VL-SARAH(37C) according to the present invention, or the fragment antibody according to the embodiment of the present invention is secreted into the culture solution of the transformant, a culture solution (culture supernatant) containing VH(112C)-SARAH according to the present invention, VL-SARAH(37C) according to the present invention, or the fragment antibody according to the embodiment of the present invention is obtained.

In a case where VH(112C)-SARAH according to the present invention, VL-SARAH(37C) according to the present invention, or the fragment antibody according to the embodiment of the present invention is present in the periplasm or cytoplasm of the transformant, the bacterial bodies or cells are recovered from the culture by a method such as filtration or centrifugation and are resuspended in an appropriate buffer solution. Then, after destroying the cell wall and/or the cell membrane of the recovered cells or the like by a method such as surfactant treatment, ultrasonic treatment, lysozyme treatment, or freeze-thawing, a crude extract containing VH(112C)-SARAH according to the present invention, VL-SARAH(37C) according to the present invention, or the fragment antibody according to the embodiment of the present invention is obtained by a method such as centrifugation or filtration.

In a case where VH(112C)-SARAH according to the present invention, VL-SARAH(37C) according to the present invention, or the fragment antibody according to the embodiment of the present invention is expressed as an inclusion body, the bacterial bodies or cells are recovered from the culture by a method such as filtration or centrifugation and are resuspended in an appropriate buffer solution. Then, after destroying the cell wall and/or the cell membrane of the recovered cells or the like by a method such as surfactant treatment, ultrasonic treatment, lysozyme treatment, or freeze-thawing, a precipitate containing VH(112C)-SARAH according to the present invention, VL-SARAH (37C) according to the present invention, or the fragment antibody according to the embodiment of the present invention is obtained by a method such as centrifugation or filtration. In this case, it is necessary to carry out a solubilization step to be described later.

In the method for preparing the fragment antibody according to the embodiment of the present invention, a solubilization step, a refolding step, a concentration step, and the like are carried out, if necessary, after the gene recombination/expression step (1).

Solubilization Step

In a case where VH(112C)-SARAH according to the present invention, VL-SARAH(37C) according to the present invention, or the fragment antibody according to the embodiment of the present invention was expressed as an inclusion body in the gene recombination/expression step (1), the solubilization step is a step of subjecting VH(112C)-SARAH according to the present invention, VL-SARAH (37C) according to the present invention, or the fragment antibody according to the embodiment of the present invention to solubilization from the recovered precipitate containing VH(112C)-SARAH according to the present invention, VL-SARAH(37C) according to the present invention, or the fragment antibody according to the embodiment of the present invention to obtain a solubilizing solution containing them.

The solubilization method may be in accordance with a known method and is not particularly limited.

Specifically, a solubilizing solution containing VH(112C)-SARAH according to the present invention, VL-SARAH(37C) according to the present invention, or the fragment antibody according to the embodiment of the present invention may be obtained by adding a solubilizing solution to the precipitate containing VH(112C)-SARAH according to the present invention, VL-SARAH(37C) according to the present invention, or the fragment antibody according to the embodiment of the present invention recovered in the gene recombination/expression step (1).

The solubilizing solution is not particularly limited as long as it solubilizes the precipitate of the inclusion body obtained in step (1) and may be, for example, a known solubilizing solution containing 6 M guanidine hydrochloride, 8 M urea, or the like. More specific examples of the solubilizing solution include a 6 M guanidine hydrochloride solubilizing solution [6 M guanidine hydrochloride, 50 mM Tris-HCl (pH 8.0), 150 mM NaCl] and a 8 M urea solubilizing solution [8 M Urea, 50 mM Tris-HCl (pH 8.0), 150 mM NaCl].

Refolding Step

In a case of expressing VH(112C)-SARAH according to the present invention and VL-SARAH(37C) according to the present invention in separate hosts, the refolding step is a method of forming a complex of VH(112C)-SARAH according to the present invention in the solubilizing solution of VH(112C)-SARAH according to the present invention obtained in the solubilization step, the crude extract of VH(112C)-SARAH according to the present invention obtained in the gene recombination/expression step (1), or the culture solution (culture supernatant) of VH(112C)-SARAH according to the present invention obtained in the gene recombination/expression step (1), and VL-SARAH(37C) according to the present invention in the solubilizing solution of VL-SARAH(37C) according to the present invention obtained in the solubilization step, the crude extract of VL-SARAH(37C) according to the present invention obtained in the gene recombination/expression step (1), or the culture solution (culture supernatant) of VL-SARAH(37C) according to the present invention obtained in the gene recombination/expression step (1) by a refolding method.

The refolding method may be in accordance with a known method and is not particularly limited as long as it can form a complex of VH(112C)-SARAH according to the present invention and VL-SARAH(37C) according to the present invention.

Specifically, a refolded solution containing the fragment antibody according to the embodiment of the present invention may be obtained in such a manner that the solubilizing solution of VH(112C)-SARAH according to the present invention obtained in the solubilization step, the crude extract of VH(112C)-SARAH according to the present invention obtained in the gene recombination/expression step (1), or the culture solution (culture supernatant) of VH(112C)-SARAH according to the present invention obtained in the gene recombination/expression step (1), and the solubilizing solution of VL-SARAH(37C) according to the present invention obtained in the solubilization step, the crude extract of VL-SARAH(37C) according to the present invention obtained in the gene recombination/expression step (1), or the culture solution (culture supernatant) of VL-SARAH(37C) according to the present invention obtained in the gene recombination/expression step (1) are mixed; and one or a plurality of refolding solutions are added to the resulting mixed solution to form the fragment antibody according to the embodiment of the present invention (complex of VH(112C)-SARAH according to the present invention and VL-SARAH(37C) according to the present invention).

Examples of the refolding solution include refolding solution A [4 M Urea, 0.4 M L-Arg, 50 mM Tris-HCl (pH 8.0), 150 mM NaCl, 375 μM oxidized glutathione] and refolding solution B [0.4 M L-Arg, 50 mM Tris-HCl (pH 8.0), 150 mM NaCl, 375 μM oxidized glutathione].

Concentration Step

The concentration step is a step of concentrating the refolded solution obtained in the refolding step to obtain a concentrated solution. The concentration step is carried out, for example, in a case where the protein is diluted by the refolding step or the like, so that a subsequent purification step can be easily carried out.

The concentration method is not particularly limited as long as it is a method capable of concentrating the refolded solution obtained in the refolding step and may be, for example, a known concentration method such as salting out method or ultrafiltration method.

(2) Purification Step

The purification step is a step of isolating and purifying the fragment antibody according to the embodiment of the present invention from the culture solution (culture supernatant) or crude extract obtained in the gene recombination/expression step (1) or the concentrated solution obtained in the concentration step.

Examples of the method for isolating and purifying the fragment antibody according to the embodiment of the present invention include a method utilizing charge such as ion exchange chromatography, a method utilizing specific affinity such as affinity chromatography, a method utilizing a difference in hydrophobicity such as reverse phase high performance liquid chromatography, a method utilizing a difference in isoelectric point such as isoelectric focusing, a method utilizing solubility such as salting out or solvent precipitation method, and a method utilizing a difference in molecular weight such as gel filtration.

The purified fragment antibody according to the embodiment of the present invention can be confirmed by, for example, SDS-PAGE or the like. For example, through the confirmation of the molecular weight by SDS-PAGE or the like, it can be confirmed whether VH(112C)-SARAH according to the present invention and VL-SARAH(37C) according to the present invention form a heterodimer to have a correct three-dimensional structure, that is, whether the cysteine residue of antibody residue 112 according to Chothia numbering scheme in the VH region in VH(112C)-SARAH according to the present invention and the cysteine residue at position 13 from the C-terminus of the SARAH domain in VL-SARAH(37C) according to the present invention form an S—S bond.

Method for Crystallizing Protein

The method for crystallizing a protein according to the embodiment of the present invention is a method of crystallizing a protein (hereinafter, sometimes referred to as a target protein) in the presence of the fragment antibody according to the embodiment of the present invention. The target protein is a protein (antigen) which is specifically recognized by the fragment antibody according to the embodiment of the present invention.

That is, the method for crystallizing a protein according to the embodiment of the present invention may be carried out by a known crystallization method in the presence of the fragment antibody according to the embodiment of the present invention, and is not particularly limited as long as it is a method of obtaining crystals of a target protein.

Specific examples of the crystallization method include a batch method, a vapor diffusion method, a dialysis method, a free interface diffusion method, a concentration method, a light irradiation method, a vibration method, and a stirring method, among which a vapor diffusion method is more preferable. Examples of the vapor diffusion method include a sitting drop method, a hanging drop method, and a sandwich drop method, among which a sitting drop method is more preferable.

More specifically, the method for crystallizing a protein according to the embodiment of the present invention contains the following steps.

(1) a step of mixing a solution containing a target protein with a solution containing the fragment antibody according to the embodiment of the present invention to form a complex of target protein and fragment antibody according to the embodiment of the present invention (hereinafter, sometimes simply referred to as complex forming step)

(2) a step of obtaining a crystal of the complex of target protein and fragment antibody according to the embodiment of the present invention (hereinafter, crystallization step)

Complex Forming Step

The complex forming step is carried out by mixing a solution containing a target protein with a solution containing the fragment antibody according to the embodiment of the present invention to form a complex of target protein and fragment antibody according to the embodiment of the present invention.

The solvent to contain the target protein is not particularly limited as long as it is commonly used in protein crystallization and examples thereof include pure water, a buffer solution, a precipitant solution, a surfactant solution, an alcohol solution, an organic solvent, a chelating agent solution, a reducing agent solution, a cryoprotectant solution, an ionic liquid, and a mixed solution thereof, among which pure water and a buffer solution are preferable. The pH of the buffer solution is not usually limited, but it is, for example, pH 4 to 9 and preferably pH 5 to 8. Specific examples of the buffer solution include phosphate buffered saline (PBS), a HEPES buffer solution, a boric acid buffer solution, a Tris buffer solution, a phosphate buffer solution, a Veronal buffer solution, and a Good's buffer solution. In addition, the concentration of a buffering agent in these buffer solutions is appropriately selected from the range of usually 5 to 100 mM and preferably 5 to 20 mM.

The solvent to contain the fragment antibody according to the embodiment of the present invention is the same as the foregoing solvent to contain a target protein, and a preferred specific example thereof is also the same.

The amount of the target protein in the solution containing the target protein and the amount of the fragment antibody according to the embodiment of the present invention in the solution containing the fragment antibody according to the embodiment of the present invention may be used in an amount such that, in a mixed solution of the solution containing the target protein and the solution containing the fragment antibody according to the embodiment of the present invention, the molar equivalent of the target protein is equal to or greater than the molar equivalent of the fragment antibody according to the embodiment of the present invention, and the concentration of the complex of target protein and fragment antibody according to the embodiment of the present invention in the mixed solution is usually 2 mg/mL to 100 mg/mL, preferably 5 mg/mL to 30 mg/mL, and more preferably 10 mg/mL to 20 mg/mL.

If necessary, the mixed solution of the solution containing a target protein and the solution containing a fragment antibody according to the embodiment of the present invention (hereinafter, sometimes simply referred to as a crystallization sample) may be concentrated by a known method such as an ultrafiltration apparatus.

Crystallization Step

The crystallization step is a step of obtaining a crystal of the complex of target protein and fragment antibody according to the embodiment of the present invention formed in the complex forming step by a crystallization method known per se, for example, a specific crystallization method as described above.

Specifically, the crystallization step may be carried out as follows, for example.

The mixed solution (crystallization sample) containing the complex of target protein and fragment antibody according to the embodiment of the present invention obtained in the complex forming step is subjected to crystallization in such a manner that the crystallization sample in an amount of usually 0.05 μL to 2 μL, preferably 0.1 μL to 0.5 μL per condition is mixed with an equal amount of a screening kit solution attached to a screening kit to prepare drops, and crystallization is carried out by a sitting drop method in the presence of a reservoir (precipitant solution) having the same composition as that of the crystallization sample in an amount of usually 50 μL to 1000 μL, preferably 80 μL to 150 μL to obtain a crystal of the complex of target protein and fragment antibody according to the embodiment of the present invention.

It should be noted that, if necessary, the three-dimensional structure of the complex of target protein and fragment antibody according to the embodiment of the present invention can be analyzed by subjecting the crystal of the complex of target protein and fragment antibody according to the embodiment of the present invention obtained by the crystallization step to a known technique such as a detecting step or an analyzing step with an X-ray diffraction apparatus.

According to the method for crystallizing a protein according to the embodiment of the present invention, high-resolution crystals are obtained by using the fragment antibody according to the embodiment of the present invention, and more crystals are obtained in a so-called screening stage.

INDUSTRIAL APPLICABILITY

Even in a case of being prepared in an *E. coli* expression system that is easier to handle than an animal cell system, the fragment antibody according to the embodiment of the present invention has an antigen-binding activity, a higher ability to crystallize than Fv-clasp (v1), a property of promoting crystallization of a protein, and the like, so it is useful in the field of protein crystallization, such as drug discovery, as a fragment antibody having the property which can be conveniently produced. In addition, the fragment antibody according to the embodiment of the present invention has heat resistance and is highly stable, so it is useful in the field of antibody medicine.

EXAMPLES

Hereinafter, the present invention will be specifically described with reference to Examples and Comparative Examples, but the present invention is not limited by these Examples.

Comparative Example 1: Preparation of Fv-Clasp (v1) of P20.1 Antibody Using *E. coli* Expression System According to the following method, VH-SARAH(Y35C) against P20.1 antibody (hereinafter, sometimes simply referred to as P20.1 antibody-VH-SARAH(Y35C)) represented by SEQ ID NO: 17 and VL-SARAH(M24C) against P20.1 antibody (hereinafter, sometimes simply referred to as P20.1 antibody-VL-SARAH(M24C)) represented by SEQ ID NO: 18 were subjected to (1) gene recombination/expression step and solubilization step, (2) refolding step, (3) concentration step, and (4) purification step to obtain Fv-clasp (v1) against P20.1 antibody (hereinafter, sometimes simply referred to as P20.1 antibody-Fv-clasp (v1)).

It should be noted that, the P20.1 antibody-Fv-clasp (v1) thus obtained was designed such that the 35th cysteine residue from the N-terminus in the SARAH domain of P20.1 antibody-VH-SARAH(Y35C) and the 24th cysteine residue from the N-terminus in the SARAH domain of the P20.1 antibody-VL-SARAH(M24C) form an S—S bond.

(1) Gene Recombination/Expression Step and Solubilization Step (1)-1: Preparation of VH-SARAH(Y35C) Against P20.1 Antibody The nucleic acid sequence encoding P20.1 antibody-VH-SARAH(Y35C) represented by SEQ ID NO: 19 was introduced into a NcoI/HindIII restriction enzyme site of pET28b (+) vector (manufactured by Novagen, Inc.) according to a conventional method to prepare a recombinant vector for expression of P20.1 antibody-VH-SARAH(Y35C). The resulting recombinant vector for expression of P20.1 antibody-VH-SARAH(Y35C) was introduced into *E. coli* BL21 (DE3) strain (manufactured by Novagen, Inc.). The *E. coli* BL21(DE3) strain into which the recombinant vector for expression of P20.1 antibody-VH-SARAH(Y35C) had been introduced was cultured at 37° C. using 1 L of LB medium. IPTG was added to the medium so that the final concentration became 0.4 mM in the vicinity of OD=0.6 and induction was carried out. The *E. coli* BL21(DE3) strain (bacterial bodies) into which the recombinant vector for expression of P20.1 antibody-VH-SARAH(Y35C) had been introduced was recovered 4 hours after the start of culture.

Among the recovered bacterial bodies, the bacterial bodies obtained by culturing in 0.5 L of the medium were suspended in 20 mL of TBS (20 mL Tris-HCl (pH 7.5), 150 mM NaCl) to obtain a suspension. Bacterial lysis reagents [Pepstatin (final concentration: 1 μM), Leupeptin (final concentration: 10 μM), PMSF (final concentration: 250 μM), and TurboNuclease (3 μL, manufactured by Accelagen, Inc.)] were added and mixed in the resulting suspension, bacterial bodies were disrupted using an ultrasonic generator (manufactured by Tomy Seiko Co., Ltd.), followed by centrifugation (25000×g, 4° C., 20 min), and the supernatant was removed to obtain a precipitate. 6 mL of a solubilizing solution [6 M guanidine hydrochloride, 50 mM Tris-HCl (pH 8.0), 150 mM NaCl] was added to the resulting precipitate, which was then subjected to incubation for 2 hours at 37° C. with occasional pipetting. This was followed by centrifugation (25000×g, 4° C., 20 min) to recover a supernatant containing P20.1 antibody-VH-SARAH(Y35C).

(1)-2: Preparation of VL-SARAH(M24C) Against P20.1 Antibody

The nucleic acid sequence encoding P20.1 antibody-VL-SARAH(M24C) represented by SEQ ID NO: 20 was introduced into a NcoI/XhoI restriction enzyme site of pET16b vector (manufactured by Novagen, Inc.) according to a conventional method to prepare a recombinant vector for expression of P20.1 antibody-VL-SARAH(M24C). The resulting recombinant vector for expression of P20.1 antibody-VL-SARAH(M24C) was introduced into E. coli BL21 (DE3) strain (manufactured by Novagen, Inc.).

After introduction of the expression vector into E. coli, P20.1 antibody-VL-SARAH(M24C) was prepared in the same manner as in the section (1)-1 and the supernatant containing P20.1 antibody-VL-SARAH(M24C) was recovered.

(2) Refolding Step

The supernatant containing P20.1 antibody-VH-SARAH (Y35C) recovered in the section (1)-1 and the supernatant containing P20.1 antibody-VL-SARAH(M24C) recovered in the section (1)-2 were mixed to obtain a mixed solution. The resulting mixed solution was filtered through a 0.45 μm filter, and refolding solution A [4 M Urea, 0.4 M L-Arg, 50 mM Tris-HCl (pH 8.0), 150 mM NaCl, 375 μM oxidized glutathione] was added to the resulting filtrate with stirring so that the filtrate was diluted 25-fold, followed by incubation at 4° C. for 4 hours. Refolding solution B [0.4 M L-Arg, 50 mM Tris-HCl (pH 8.0), 150 mM NaCl, 375 μM oxidized glutathione] was added to the filtrate with stirring so that the resulting mixed solution after incubation was diluted 2-fold, followed by overnight incubation at 4° C. to obtain a refolded antibody solution.

(3) Concentration Step

Ammonium sulfate ground to give 80% saturation was gradually added to the refolded antibody solution obtained in the section (2), followed by ammonium sulfate precipitation and then incubation at 4° C. with stirring for 3 hours. The resulting solution after incubation was centrifuged (12000×g, 4° C., 60 min), and the supernatant was removed to obtain a precipitate. A refolding solution [1:1 mixed solution of the refolding solution A and the refolding solution B] was added and suspended in the resulting precipitate to obtain a suspension. The resulting suspension was dialyzed a total of 3 times in 4 to 16 hours each time using 1 L dialysis solution [50 mM Tris-HCl (pH 8.0), 150 mM NaCl] according to a conventional method. The suspension after dialysis was recovered and then centrifuged (25000×g, 4° C., 20 min) to recover the supernatant. The resulting supernatant was concentrated by ultrafiltration according to a conventional method to obtain a concentrated solution.

(4) Purification Step

According to a conventional method, the concentrated solution obtained in the section (3) was subjected to gel filtration purification using HiLoad 16/600 Superdex 200 pg (manufactured by GE Healthcare Bio-Sciences Corp.) and elution buffer for gel filtration purification [50 mM Tris-HCl (pH 8.0), 150 mM NaCl] at a flow rate of 1.0 mL/min. From the molecular weight marker, a monodisperse peak was obtained at the position estimated as P20.1 antibody-Fv-clasp (v1), and therefore the eluate of the peak was recovered.

Subsequently, the eluate recovered by gel filtration purification was subjected to SDS-PAGE according to a conventional method. As a result, a band of impurities was also confirmed in addition to the band of P20.1 antibody-Fv-clasp (v1).

Therefore, in order to remove impurities from the eluate recovered by gel filtration purification, the eluate was recovered by purification using CNBr-activated Sepharose 4 Fast Flow (manufactured by manufactured by GE Healthcare Bio-Sciences Corp.) in which C8 peptide (PRGYPGQV), which is an antigen molecule of the fragment antibody represented by SEQ ID NO: 21), was immobilized, an equilibration buffer [20 mM Tris-HCl (pH 7.5), 150 mM NaCl], and elution buffer [0.5 mg/mL C8, 20 mM Tris-HCl (pH 7.5), 150 mM NaCl].

The recovered eluate was subjected to SDS-PAGE under reducing conditions or non-reducing conditions, respectively, according to a conventional method.

The results are shown in FIG. 1. In the figure, the left lane shows the electrophoretogram under reducing conditions and the right lane shows the electrophoretogram under non-reducing conditions. Under reducing conditions, a band of P20.1 antibody-VH-SARAH(Y35C) was obtained around 18 kDa and a band of P20.1 antibody-VL-SARAH(M24C) was obtained around 16 kDa. In addition, under non-reducing conditions, a band was obtained around 35 kDa. With regard to P20.1 antibody-VH-SARAH(Y35C) and P20.1 antibody-VL-SARAH(M24C), since the introduction position of the Cys residue was designed so that an S—S bond is formed only in a case where both P20.1 antibody-VH-SARAH(Y35C) and P20.1 antibody-VL-SARAH(M24C) correctly form a heterodimer, it was found from these results that the P20.1 antibody-Fv-clasp (v1), which is a heterodimer in which the S—S bond between the chains was correctly formed, was obtained.

Comparative Example 2: Preparation of Fv-Clasp (v1) of P20.1 Antibody Using Animal Cell Expression System According to the following method, VH-SARAH(Y35C) against P20.1 antibody (containing the signal sequence of the mouse nitrogen at the N-terminus) represented by SEQ ID NO: 22 and VL-SARAH(M24C) against P20.1 antibody (containing the signal sequence of the mouse nitrogen at the N-terminus) represented by SEQ ID NO: 24 were subjected to (1) gene recombination step, (2) recombinant protein expression step using an animal cell expression system, and (3) purification step to obtain Fv-clasp (v1) of P20.1 antibody (hereinafter, sometimes simply referred to as P20.1 antibody-Fv-clasp (v1)).

(1) Gene Recombination Step

A nucleic acid sequence encoding VH-SARAH(Y35C) against P20.1 antibody (containing a sequence encoding the signal sequence of mouse nitrogen at the N-terminus) represented by SEQ ID NO: 23 was introduced into a HindIII/PmeI restriction enzyme site of pcDNA 3.1 vector (manufactured by Thermo Fisher Scientific Inc.) according to a conventional method to prepare a recombinant vector for expression of P20.1 antibody-VH-SARAH(Y35C). In addition, a nucleic acid sequence encoding VL-SARAH(M24C) against P20.1 antibody (containing a sequence encoding the signal sequence of mouse nitrogen at the N-terminus) represented by SEQ ID NO: 25 was used in place of the nucleic acid sequence represented by SEQ ID NO: 23 to prepare a recombinant vector for expression of P20.1 antibody-VL-SARAH(M24C).

(2) Recombinant Protein Expression Step Using Animal Cell Expression System

Expi293F cells (manufactured by Thermo Fisher Scientific Inc.) were seeded using 600 mL of Expi293 Expression Medium (manufactured by Thermo Fisher Scientific Inc.) so that the cell density reached $3\times10^6$ cells/mL. Thereafter, 400 μg of a recombinant vector for expression of P20.1 antibody-VH-SARAH(Y35C) and 400 μg of a recombinant vector for expression of P20.1 antibody-VL-SARAH(M24C) were transfected into Expi293F cells according to a conventional method using ExpiFectamine 293 Reagent (manufactured by Thermo Fisher Scientific Inc.). After transfection, Expi293F cells thus transfected were cultured with shaking for 18 hours at 125 rpm under the conditions of 37° C. and 8% $CO_2$. Thereafter, 3 mL of ExpiFectamine 293 Transfection Enhancer 1 (manufactured by Thermo Fisher Scientific Inc.) and 30 mL ExpiFectamine 293 Transfection Enhancer 2 (manufactured by Thermo Fisher Scientific Inc.) were added to the cells which were then cultured with shaking for 3 days at 125 rpm under the conditions of 37° C. and 8% $CO_2$, and the culture supernatant was recovered.

(3) Purification Step

The culture supernatant recovered in the section (2) was purified in the same manner as in Comparative Example 1, using CNBr-activated Sepharose 4 Fast Flow (manufactured by GE Healthcare Bio-Sciences Corp.) in which the C8 peptide was immobilized. Subsequently, the eluted fraction was subjected to gel filtration purification at a flow rate of 0.5 mL/min according to a conventional method, using Superdex 200 Icrease 10/300 GL (manufactured by GE Healthcare Bio-Sciences Corp.) and elution buffer for gel filtration purification [20 mM Tris-HCl (pH 7.5), 150 mM NaCl]. From the molecular weight marker, a monodisperse peak was obtained at the position estimated as P20.1 antibody-Fv-clasp (v1), and therefore the eluate of the peak was recovered.

The recovered eluate was subjected to SDS-PAGE under reducing conditions or non-reducing conditions, respectively, according to a conventional method.

Figure 2:
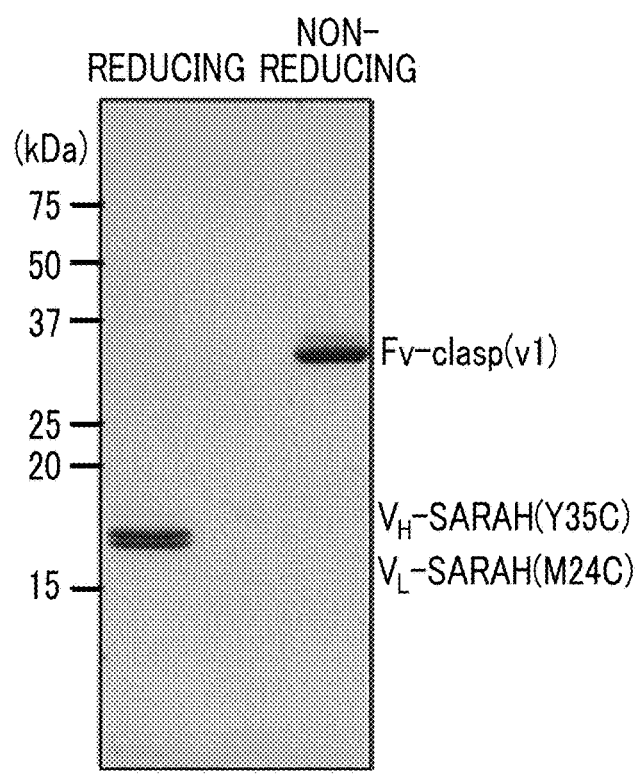
FIG. 2 is a view confirming that P20.1 antibody-Fv-clasp (v1) was obtained by SDS-PAGE in Comparative Example 2.

The results are shown in FIG. 2. In the figure, the left lane shows the electrophoretogram under reducing conditions and the right lane shows the electrophoretogram under non-reducing conditions. Under reducing conditions, a band of P20.1 antibody-VH-SARAH(Y35C) was obtained around 18 kDa and a band of P20.1 antibody-VL-SARAH(M24C) was obtained around 16 kDa. In addition, under non-reducing conditions, a band was obtained around 35 kDa. With regard to P20.1 antibody-VH-SARAH(Y35C) and P20.1 antibody-VL-SARAH(M24C), since the introduction position of the Cys residue was designed so that an S—S bond is formed only in a case where both P20.1 antibody-VH-SARAH(Y35C) and P20.1 antibody-VL-SARAH(M24C) correctly form a heterodimer, it was found from these results that the P20.1 antibody-Fv-clasp (v1), which is a heterodimer in which the S—S bond between the chains was correctly formed, was obtained.

Comparative Example 3: Preparation of Fv-Clasp (v1) of 12CA5 Antibody Using *E. coli* Expression System Fv-clasp (v1) of 12CA5 antibody (hereinafter, sometimes simply referred to as 12CA5 antibody-Fv-clasp (v1)) was obtained in the same manner as in Comparative Example 1, except that a nucleic acid sequence encoding VH-SARAH (Y35C) against 12CA5 antibody represented by SEQ ID NO: 26 was used in place of the nucleic acid sequence encoding P20.1 antibody-VH-SARAH(Y35C) represented by SEQ ID NO: 19, and a nucleic acid sequence encoding VL-SARAH(M24C) against 12CA5 antibody represented by SEQ ID NO: 27 was used in place of the nucleic acid sequence encoding VL-SARAH(M24C) against P20.1 antibody represented by SEQ ID NO: 20, by subjecting VH-SARAH(Y35C) against 12CA5 antibody (hereinafter, sometimes simply referred to as 12CA5 antibody-VH-SARAH(Y35C)) represented by SEQ ID NO: 28 and VL-SARAH(M24C) against 12CA5 antibody (hereinafter, sometimes simply referred to as 12CA5 antibody-VL-SARAH(M24C)) represented by SEQ ID NO: 29 to (1) gene recombination/expression step and solubilization step, (2) refolding step, and (3) concentration step, and further (4) purification step shown below.

The results of the purification step (4) are described below.

The concentrated solution obtained in the concentration step (3) was subjected to gel filtration purification in the same manner as in Comparative Example 1. As a result, from the molecular weight marker, a monodisperse peak was obtained at the position estimated as 12CA5 antibody-Fv-clasp (v1) and therefore the eluate of the peak was recovered.

Subsequently, the recovered eluate was subjected to non-reducing SDS-PAGE according to a conventional method. As a result, bands of impurities were also confirmed around 15 to 18 kDa in addition to the band of 12CA5 antibody-Fv-clasp (v1) around 37 kDa. With regard to the 12CA5 antibody-VH-SARAH(Y35C) and 12CA5 antibody-VL-SARAH(M24C), since the introduction position of the Cys residue was designed so that an S—S bond is formed only in a case where both 12CA5 antibody-VH-SARAH(Y35C) and 12CA5 antibody-VL-SARAH(M24C) correctly form a heterodimer, these bands of impurities were thought to be homodimers of each of 12CA5 antibody-VH-SARAH (Y35C) and 12CA5 antibody-VL-SARAH(M24C), or heterodimers of unoxidized state due to partially incomplete refolding.

Therefore, in order to remove impurities from the eluate recovered by gel filtration purification, the eluate was subjected to ion exchange chromatography according to a conventional method, by applying a gradient over 20 mL at a flow rate of 1 mL/min using Mono Q5/50 (manufactured by GE Healthcare Bio-Sciences Corp.) and elution buffer for ion exchange chromatography [50 mM to 300 mM gradient of NaCl in Tris-HCl, pH 7.5].

As a result, two small peaks (hereinafter, sometimes simply referred to as peaks 13 and C) were obtained after the largest peak (hereinafter, sometimes simply referred to as peak A).

The recovered eluates of peaks A to C were subjected to SDS-PAGE under non-reducing and reducing conditions, respectively, according to a conventional method.

Figure 3:
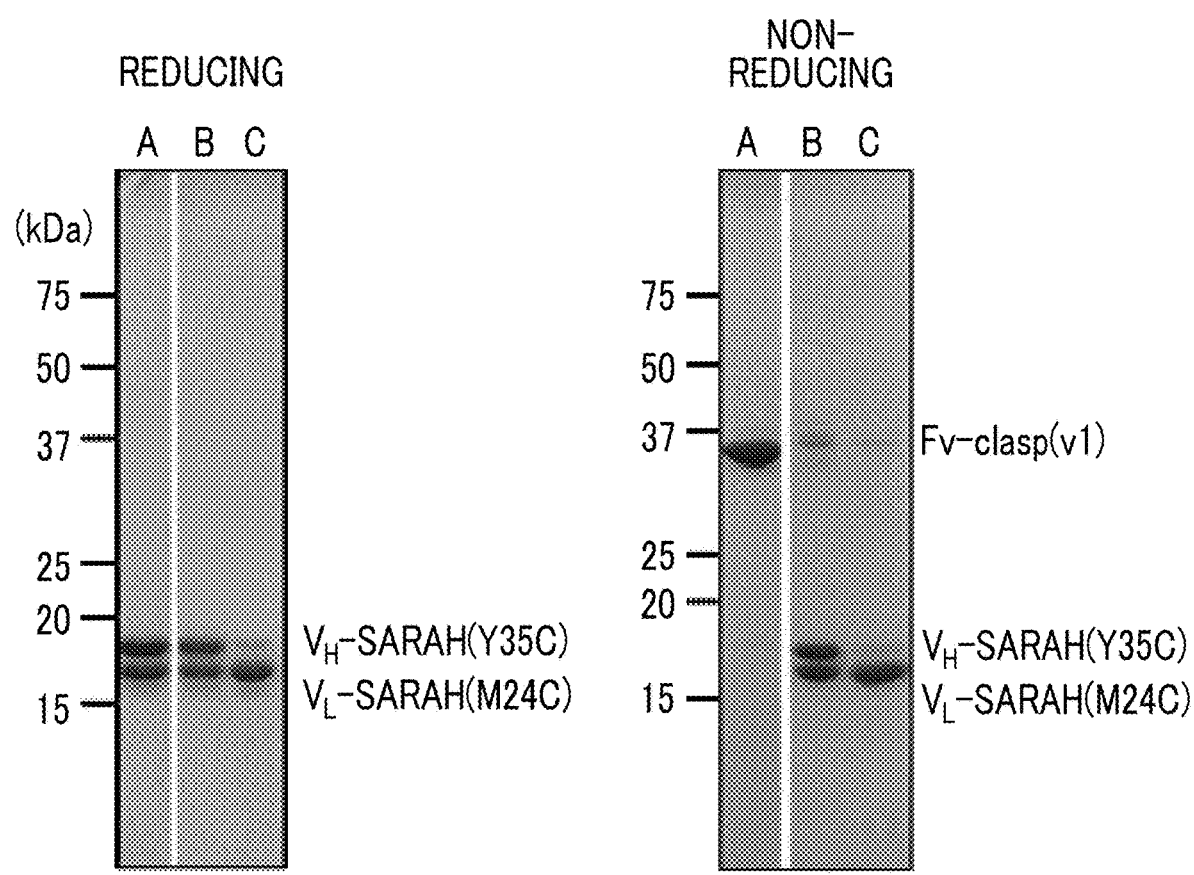
FIG. 3 is a view confirming that 12CA5 antibody-Fv-clasp (v1) was obtained by SDS-PAGE in Comparative Example 3.

The results are shown in FIG. 3. In the figure, the gel on the left side is electrophoretogram under reducing conditions and the gel on the right side is electrophoretogram under non-reducing conditions. The lane names A to C correspond to the names of eluents of peaks A to C recovered by gel filtration purification, respectively.

As a result of electrophoresis under non-reducing conditions, A showed a band of 12CA5 antibody-Fv-clasp (v1) around 35 kDa; B showed a band of 12CA5 antibody-VH-SARAH(Y35C) around 18 kDa and a band of 12CA5 antibody-VL-SARAH(M24C) band around 16 kDa; and C showed a band of 12CA5 antibody-VL-SARAH(M24C) around 16 kDa.

From these results, it was found that the 12CA5 antibody-Fv-clasp (v1), which is a heterodimer in which the S—S bond between the chains was correctly formed, was obtained at peak A. It should be noted that, the peak B was considered as a heterodimer molecule in an unoxidized state, and the peak C was considered as a homodimer molecule.

Comparative Example 4: Crystal Structure Analysis of Complex of Fv-Clasp (v1) of P20.1 Antibody Obtained in *E. coli* Expression System and C8 Peptide Using the P20.1 antibody-Fv-clasp (v1) obtained by the *E. coli* expression system in Comparative Example 1, crystallization of a complex of P20.1 antibody-Fv-clasp (v1) and C8 peptide, which is an antigen molecule of this fragment antibody, was carried out by the following method. The P20.1 antibody-Fv-clasp (v1) and the C8 peptide were mixed so that the final concentrations thereof were 7 mg/mL and 1 mM, respectively, to obtain a crystallization sample. Using an automatic crystallization apparatus mosquito (manufactured by TTP LabTech Ltd.), various screening kits [Classics Neo Suite (manufactured by QIAGEN GmbH) (96 conditions), Wizard Classic 1 & 2 (manufactured by Rigaku Corporation) (96 conditions), Wizard Precipitant Synergy (manufactured by Rigaku Corporation) (192 conditions), SaltRx (manufactured by Hampton Research Corporation) (96 conditions), and a VIOLAMO protein crystallization plate (96 wells, manufactured by As One Corporation), a drop was prepared by mixing 0.1 µL of crystallization sample and 0.1 µL of screening kit solution (crystallization reagent) per condition, and using 80 µL of crystallization reagent for reservoir, screening of crystallization was carried out by crystallization by a sitting drop vapor diffusion method.

As described above, a total of 480 screening conditions were examined using four types of kits, but no crystal could be obtained at all. It was found that Fv-clasp (v1) obtained in the *E. coli* expression system has no ability to crystallize in the complex of fragment antibody and antigen molecule.

Comparative Example 5: Crystal Structure Analysis of Complex of Fv-Clasp (v1) of P20.1 Antibody Obtained in Animal Cell Expression System and C8 Peptide Using the P20.1 antibody-Fv-clasp (v1) obtained by the animal cell expression system in Comparative Example 2, crystallization of a complex of P20.1 antibody-Fv-clasp (v1) and C8 peptide, which is an antigen molecule of this fragment antibody, was carried out in the same manner as in Comparative Example 4. However, Index (manufactured by Hampton Research Corporation) and Wizard Classic 1 & 2 (manufactured by Rigaku Corporation) were used as the screening kits.

Figure 4:
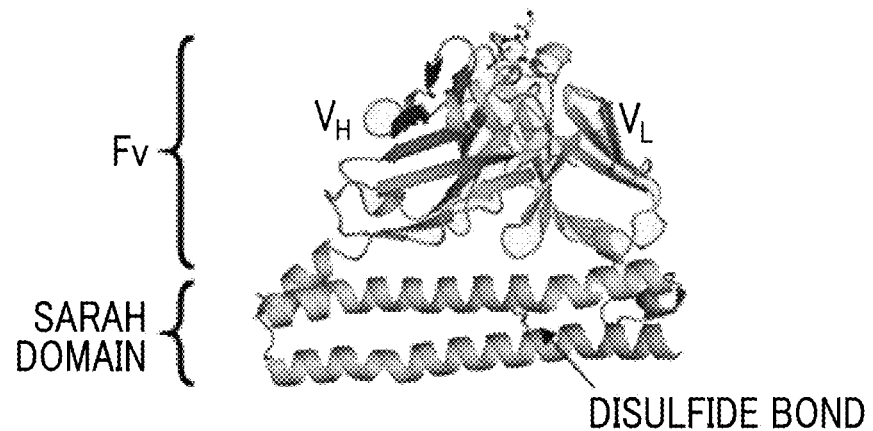
FIG. 4 shows the result of X-ray crystallography of a complex of Fv-clasp (v1) of P20.1 antibody and C8 peptide carried out in Comparative Example 5.

As a result, crystals were obtained in 7 conditions (3.6%) out of 192 conditions in the complex of P20.1 antibody-Fv-clasp (v1) and C8 peptide in the screening stage. Regarding the crystal (Crystal-1) obtained by further optimizing the conditions for one of these conditions and the crystal (Crystal-2) obtained under different conditions from Crystal-1 in screening, an X-ray diffraction experiment was carried out at synchrotron radiation facility SPring-8. As a result, X-ray diffraction data were obtained with Crystal-1 at 1.31 Å resolution and Crystal-2 at 1.75 Å resolution, respectively. Using the obtained X-ray diffraction data, the phase was determined by a molecular replacement method using the crystal structure of P20.1 Fab (PDB ID: 2ZPK) and the crystal structure of SARAH domain of Mst1 (PDB 4NR2) as a search model and using a molecular replacement program PHASER [McCoy, A. J., et al. Phaser crystallographic software. J. Appl. Crystallogr. 40, pp. 658 to 674 (2007)]. Thereafter, REFMAC 5 [Murshudov, G. N., et al. REFMAC 5 for the refinement of macromolecular crystal structures. Acta Crystallogr. D Biol. Crystallogr. 67, pp. 355 to 367 (2011)] and PHENIX [Adams, P., et al. Recent developments in the PHENIX software for automated crystallographic structure determination. J. Synchrotron. Radiat., 11, pp. 53 to 55. (2004)] were used to refine the structure. The results of X-ray crystallography of the obtained P20.1 antibody Fv-clasp (v1) and C8 peptide complex (Crystal-1) are shown in FIG. 4.

Comparative Example 6: Crystal Structure Analysis of Complex of 12CA5 Antibody-Fv-Clasp (v1) Obtained in *E. coli* Expression System and HA Peptide Using the 12CA5 antibody-Fv-clasp (v1) obtained by the *E. coli* expression system in Comparative Example 3, crystallization of a complex of 12CA5 antibody-Fv-clasp (v1) and HA peptide (YPYDVPDYA), which is an antigen molecule represented by SEQ ID NO: 30, was carried out in the same manner as in Comparative Example 4. However, a mixture of 12CA5 antibody-Fv-clasp (v1) and HA peptide so that the final concentrations thereof were 7 mg/mL and 1 mM, respectively, was used as a crystallization sample, and the screening kits used were Classics Neo Suite (manufactured by QIAGEN GmbH) (96 conditions), Classics II Suite (manufactured by QIAGEN GmbH) (96 conditions), and Wizard Classic 1 & 2 (manufactured by Rigaku Corporation) (96 conditions).

As a result, in the complex of 12CA5 antibody-Fv-clasp (v1) and antigen molecule HA peptide in the screening stage, crystals were obtained in 51 conditions (17.7%) out of a total of 288 conditions using the above three types of kits.

Figure 5:
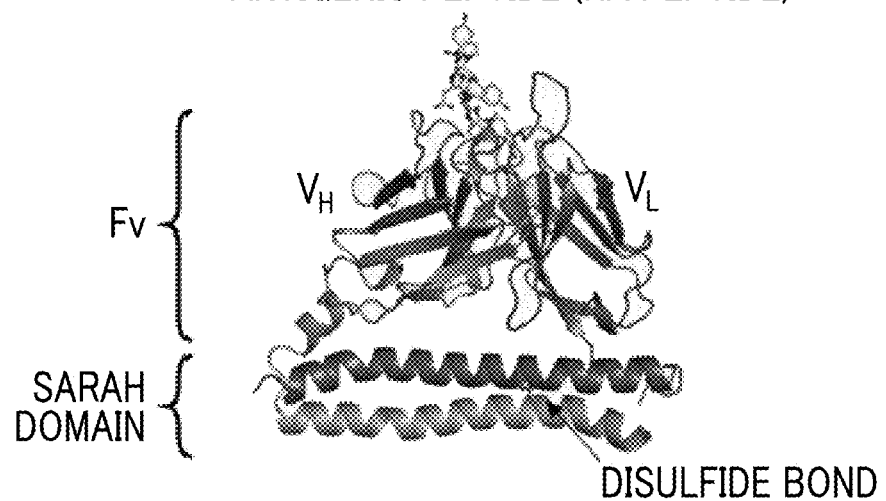
FIG. 5 shows the result of X-ray crystallography of a complex of Fv-clasp (v1) of 12CA5 antibody and HA peptide carried out in Comparative Example 6.

In a case where ten types of crystals out of the obtained complex crystals were subjected to X-ray diffraction experiments in the same manner as in Comparative Example 5, they showed a low diffraction ability of approximately 4 to 9 Å. Therefore, investigations of crystallization conditions and X-ray diffraction experiments for one type out of these crystals were repeated to optimize the crystallization conditions, and as a result, data collection at 2.2 Å was successful. With respect to this data, the three-dimensional structure was determined in the same manner as in Comparative Example 5 (except that PDB ID: 1HIL was used as a search model for molecular replacement for Fv region). FIG. 5 shows the structure of the obtained complex of 12CA5 antibody-Fv-clasp (v1) and HA peptide.

It was found that, even in a case where Fv-clasp (v1) obtained in the *E. coli* expression system has an ability to crystallize in the screening stage, the number of screening conditions for obtaining crystals is smaller than Fv-clasp (v2) described later and further, crystals obtained by screening tend to have a low diffraction ability (low ability to crystallize).

In the following Comparative Examples 7 to 9 and Example 1, based on the structure of Fv-clasp (v1) obtained in Comparative Example 5, mutants of Fv-clasp (v1) (Fv-clasp (without S—S), Fv-clasp (v1'), Fv-clasp (v1"), and Fv-clasp (v2), which will be described later) were prepared in order to improve Fv-clasp (v1).

The positions of S—S bonds in individual mutants are shown in Table 1 below.

TABLE 1

| | Designation of single-chain antibody | Position of introduced S-S bond | |
|---|---|---|---|
| | | VH-SARAH | VL-SARAH |
| Comparative Example 7 | 2H5 antibody-Fv-clasp (without S-S) | Absent | Absent |
| Comparative Example 8 | Fv-clasp (v1') of 2H5 antibody | Cysteine residue of antibody residue 11 according to Chothia numbering scheme in VH region of VH(11C)-SARAH against 2H5 antibody | Cysteine residue at position 17 from C-terminus (position 33 from N-terminus) of SARAH domain of VL-SARAH(33C) against 2H5 antibody |
| Comparative Example 9 | Fv-clasp (v1") of 2H5 antibody | Cysteine residue of antibody residue 108 according to Chothia numbering scheme in VH region of 2H5 antibody-VH(108C)-SARAH | Cysteine residue at position 20 from C-terminus (position 30 from N-terminus) of SARAH domain of 2H5 antibody-VL-SARAH(30C) |
| Example 1 | Fv-clasp (v2) of 2H5 antibody | Cysteine residue of antibody residue 112 according to Chothia numbering scheme in VH region of 2H5 antibody-VH(112C)-SARAH | Cysteine residue at position 13 from C-terminus (position 37 from N-terminus) of SARAH domain of 2H5 antibody-VL-SARAH(37C) |

Comparative Example 7: Preparation of Fv-Clasp (without S—S) of 2H5 Antibody Using Animal Cell Expression System According to the following method, VH-SARAH to the 2H5 antibody (containing the signal sequence of the 2H5 heavy chain at the N-terminus and the His tag sequence at the C-terminus, and hereinafter sometimes, simply referred to as 2H5 antibody-VH-SARAH) represented by SEQ ID NO: 31 and VL-SARAH to the 2H5 antibody (containing the signal sequence of the 2H5 light chain at the N-terminus and the His tag sequence at the C-terminus, and hereinafter sometimes simply referred to as 2H5 antibody-VL-SARAH) represented by SEQ ID NO: 32 were subjected to (1) gene recombination step, (2) recombinant protein expression step using an animal cell expression system, and (3) purification step to obtain a culture supernatant containing Fv-clasp (without S—S) of 2H5 antibody (hereinafter, sometimes simply referred to as 2H5 antibody-Fv-clasp (without S—S)).

(1) Gene Recombination Step

A recombinant vector for expression of 2H5 antibody-VH-SARAH and 2H5 antibody-VL-SARAH was prepared in the same manner as in Comparative Example 2, except that a nucleic acid sequence encoding VH-SARAH against 2H5 antibody (containing a signal sequence of a 2H5 heavy chain at the N-terminus and a sequence encoding a His tag sequence at the C-terminus) represented by SEQ ID NO: 33 was used in place of the nucleic acid sequence encoding VH-SARAH(Y35C) against P20.1 antibody (containing a sequence encoding the signal sequence of mouse nitrogen at the N-terminus) represented by SEQ ID NO: 23, and a nucleic acid sequence encoding VL-SARAH against 2H5 antibody (containing a signal sequence of a 2H5 light chain at the N-terminus and a sequence encoding a His tag sequence at the C-terminus) represented by SEQ ID NO: 34 was used in place of the nucleic acid sequence encoding VL-SARAH(M24C) against P20.1 antibody (containing a sequence encoding the signal sequence of mouse nitrogen at the N-terminus) represented by SEQ ID NO: 25.

(2) Recombinant Protein Expression Step Using Animal Cell Expression System

A culture supernatant containing 2H5 antibody-Fv-clasp (without S—S) was recovered in the same manner as in Comparative Example 2, except that a recombinant vector for expression of 2H5 antibody-VH-SARAH was used in place of the recombinant vector for expression of P20.1 antibody-VH-SARAH(Y35C), and a recombinant vector for expression of 2H5 antibody-VL-SARAH was used in place of the recombinant vector for expression of P20.1 antibody-VL-SARAH(M24C).

(3) Purification Step

A precipitation reaction was carried out on 1 mL of the recovered culture supernatant by affinity chromatography using 20 μL of CNBr-activated Sepharose 4 Fast Flow (manufactured by GE Healthcare Bio-Sciences Corp.) in which eTEV peptide (RENLYFQGKDG), which is an antigen molecule of 2H5 represented by SEQ ID NO: 89, was immobilized, and the protein bound to the carrier was eluted to obtain an eluate (hereinafter, sometimes simply referred to as S—S-free eluate).

It should be noted that, the obtained 2H5 antibody-Fv-clasp (without S—S) was designed to have no new cysteine residue in the Fv region of the 2H5 antibody and the SARAH domain sequence fused thereto, and not form S—S bonds between molecules.

Comparative Example 8: Preparation of Fv-Clasp (v1') of 2H5 Antibody Using Animal Cell Expression System In the same manner as in Comparative Example 7, VH(11C)-SARAH against 2H5 antibody (containing the signal sequence of the 2H5 heavy chain at the N-terminus and the His tag sequence at the C-terminus, and hereinafter sometimes simply referred to as 2H5 antibody-VH(11C)-SARAH) represented by SEQ ID NO: 35 and VL-SARAH (33C) against 2H5 antibody (containing the signal sequence of the 2H5 light chain at the N-terminus and the His tag sequence at the C-terminus, and hereinafter sometimes simply referred to as 2H5 antibody-VL-SARAH(33C)) represented by SEQ ID NO: 36 were subjected to (1) gene recombination step, (2) recombinant protein expression step using an animal cell expression system, and (3) purification step to obtain an eluate (hereinafter, sometimes simply referred to as v1' eluate) containing Fv-clasp (v1') of 2H5 antibody (hereinafter, sometimes simply referred to as 2H5 antibody-Fv-clasp (v1')).

It should be noted that, the obtained 2H5 antibody-Fv-clasp (v1') was designed such that the cysteine residue of antibody residue 11 according to Chothia numbering scheme in the VH region of VH(11C)-SARAH against 2H5 antibody and the cysteine residue at position 17 from the C-terminus (position 33 from the N-terminus) in the SARAH domain of 2H5 antibody-VL-SARAH(33C) form an S—S bond.

Comparative Example 9: Preparation of Fv-Clasp (v1″) of 2115 Antibody Using Animal Cell Expression System In the same manner as in Comparative Example 7, VH(108C)-SARAH against 2H5 antibody (containing the signal sequence of the 2H5 heavy chain at the N-terminus and the His tag sequence at the C-terminus, and hereinafter sometimes simply referred to as 2H5 antibody-VH(108C)-SARAH) represented by SEQ ID NO: 37 and VL-SARAH (30C) against 2H5 antibody (containing the signal sequence of the 2H5 light chain at the N-terminus and the His tag sequence at the C-terminus, and hereinafter sometimes simply referred to as 2H5 antibody-VL-SARAH(30C)) represented by SEQ ID NO: 38 were subjected to (1) gene recombination step, (2) recombinant protein expression step using an animal cell expression system, and (3) purification step to obtain an eluate (hereinafter, sometimes simply referred to as v1″ eluate) containing Fv-clasp (v1″) of 2115 antibody (hereinafter, sometimes simply referred to as 2115 antibody-Fv-clasp (v1″)).

It should be noted that, the obtained 2H5 antibody-Fv-clasp (v1″) was designed such that the cysteine residue of antibody residue 108 according to Chothia numbering scheme in the VH region of VH(108C)-SARAH against 2H5 antibody and the cysteine residue at position 20 from the C-terminus (position 30 from the N-terminus) in the SARAH domain of 2H5 antibody-VL-SARAH(30C) form an S—S bond.

Example 1: Preparation of Fv-Clasp (v2) of 2H5 Antibody Using Animal Cell Expression System In the same manner as in Comparative Example 7, VH(112C)-SARAH against 2H5 antibody (containing the signal sequence of the 2H5 heavy chain at the N-terminus and the His tag sequence at the C-terminus, and hereinafter sometimes simply referred to as 2H5 antibody-VH(112C)-SARAH) represented by SEQ ID NO: 39 and VL-SARAH (37C) against 2H5 antibody (containing the signal sequence of the 2H5 light chain at the N-terminus and the His tag sequence at the C-terminus, and hereinafter sometimes simply referred to as 2H5 antibody-VL-SARAH(37C)) represented by SEQ ID NO: 40 were subjected to (1) gene recombination step, (2) recombinant protein expression step using an animal cell expression system, and (3) purification step to obtain an eluate (hereinafter, sometimes simply referred to as v2 eluate) containing Fv-clasp (v2) of 2H5 antibody (hereinafter, sometimes simply referred to as 2H5 antibody-Fv-clasp (v2)).

It should be noted that, the obtained 2115 antibody-Fv-clasp (v2) was designed such that the cysteine residue of antibody residue 112 according to Chothia numbering scheme in the VH region of VH(112C)-SARAH against 2H5 antibody and the cysteine residue at position 13 from the C-terminus (position 37 from the N-terminus) in the SARAH domain of 2H5 antibody-VL-SARAH(37C) form an S—S bond.

Experimental Example 1: S—S Bond Forming Ability of Variety of Fv-Clasp Versions of 2H5 Antibody Each of eluates obtained in Comparative Examples 7 to 9 and Example 1 was subjected to SDS-PAGE under reducing conditions or non-reducing conditions, respectively, according to a conventional method.

Figure 6:
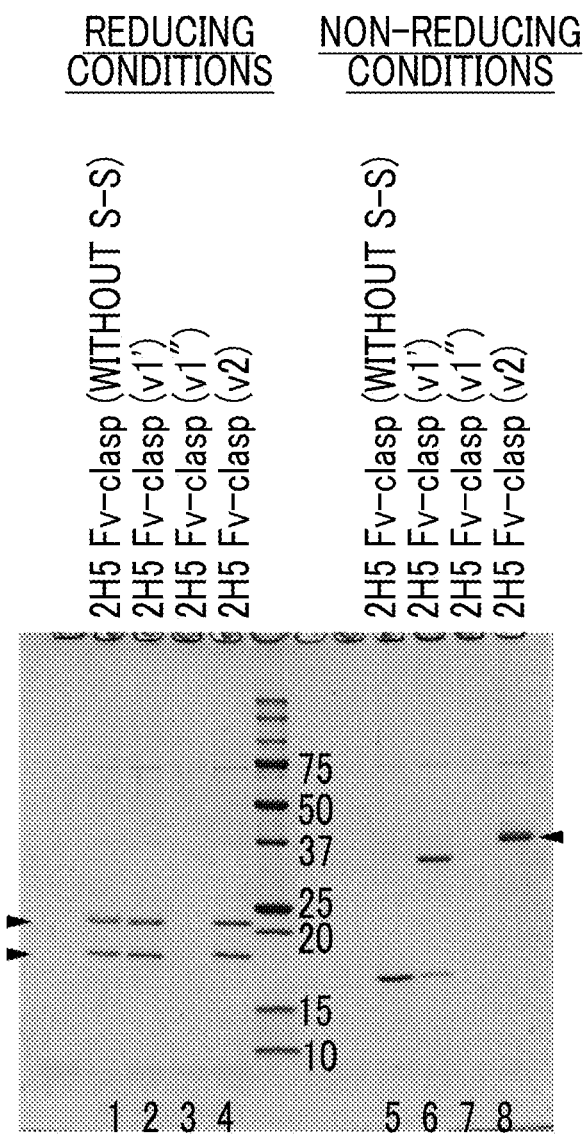
FIG. 6 is a view showing an S—S bond forming ability of Fv-clasp (without S—S) of 2H5 antibody, Fv-clasp (v1') of 2H5 antibody, Fv-clasp (v1") of 2H5 antibody, and Fv-clasp (v2) of 2H5 antibody obtained in Comparative Examples 7 to 9 and Example 1, confirmed by SDS-PAGE in Experimental Example 1.

The results are shown in FIG. 6. In the figure, the left side of the gel (lanes 1 to 4) is an electrophoretogram under reducing conditions and the right side of the gel (lanes 5 to 8) is an electrophoretogram under non-reducing conditions with the lane of a marker at the center being therebetween. Lane 1 shows the electrophoresis results of the S—S-free eluate obtained in Comparative Example 7 under reducing conditions; lane 2 shows the electrophoresis results of the v1' eluate obtained in Comparative Example 8 under reducing conditions; lane 3 shows the electrophoresis results of the v1″ eluate obtained in Comparative Example 9 under reducing conditions; lane 4 shows the electrophoresis results of the v2 eluate obtained in Example 1 under reducing conditions; lane 5 shows the electrophoresis results of the S—S-free eluate obtained in Comparative Example 7 under non-reducing conditions; lane 6 shows the electrophoresis results of the v1' eluate obtained in Comparative Example 8 under non-reducing conditions; lane 7 shows the electrophoresis results of the v1″ eluate obtained in Comparative Example 9 under non-reducing conditions; and lane 8 shows the electrophoresis results of the v2 eluate obtained in Example 1 under non-reducing conditions.

Under reducing conditions, in each of the S—S free eluate (lane 1), v1' eluate (lane 2), and v2 eluate, a band of 2H5 antibody-VH-SARAH or a band of a mutant in which a cysteine residue was introduced into 2H5 antibody-VH-SARAH was obtained around 22 kDa, and a band of 2H5 antibody-VL-SARAH or a band of a mutant in which a cysteine residue was introduced into 2H5 antibody-VL-SARAH was obtained around 18 kDa. On the other hand, the v1″ eluate (lane 3) did not give a band corresponding to a mutant in which a cysteine residue was introduced in 2H5 antibody-VH-SARAH or a mutant in which a cysteine residue was introduced in 2H5 antibody-VL-SARAH.

In addition, under non-reducing conditions, the S—S-free eluate (lane 5) did not give a band of an expected Fv-clasp dimer of 2H5 antibody around 35 to 37 kDa; and the v1' eluate (lane 6) gave a band of a single 2H5 antibody-VH-SARAH that did not form an S—S bond and a band of 2H5 antibody-VH-SARAH around 17 kDa, in addition to a band (around 35 kDa) of Fv-clasp (v1') of 2H5 antibody that formed an S—S bond, whereas the v2 eluate (lane 8) gave only a band (37 kDa) of Fv-clasp (v2) of 2H5 antibody that formed an S—S bond.

From the electrophoresis results under reducing conditions, it was found that Fv-clasp (without S—S) (Comparative Example 7), Fv-clasp (v1') (Comparative Example 8), and Fv-clasp (v2) (Comparative Example 10) were respectively expressed and secreted from the host, and the binding activity thereof to an antigen molecule was maintained. On the other hand, it was found that Fv-clasp (v1″) (Comparative Example 9) was not expressed or secreted or lost the antigen binding ability of the expressed one.

Further, from the electrophoresis results under non-reducing conditions, it was found that Fv-clasp (v1') produces impurities such as dimers or homodimers that do not form S—S bonds between molecules, while only Fv-clasp (v2) has an ability to form 100% intermolecular S—S bonds.

Based on the results of the structural analysis of Fv-clasp (v1) shown in Comparative Examples 5 and 6, in order for VH-SARAH and VL-SARAH to constitute a more stable heterodimer, the present inventors have devised three different mutants of Fv-clasp (v1'), Fv-clasp (v1"), and Fv-clasp (v2).

That is, as a combination of positions of cysteine residues to be introduced into VH-SARAH and VL-SARAH, the present inventors have devised three new combinations listed in Table 1 above {a combination of [a cysteine residue of antibody residue 11 according to Chothia numbering scheme in the VH region of VH(11C)-SARAH and a cysteine residue at position 17 from the C-terminus (position 33 from the N-terminus) in the SARAH domain of VL-SARAH (33C) (Fv-clasp (v1')], a combination of [a cysteine residue of antibody residue 108 according to Chothia numbering scheme in the VH region of VH(108C)-SARAH and a cysteine residue at position 20 from the C-terminus (position 30 from the N-terminus) in the SARAH domain of VL-SARAH(30C) (Fv-clasp (v1")], and a combination of [a cysteine residue of antibody residue 112 according to Chothia numbering scheme in the VH region of VH(112C)-SARAH and a cysteine residue at position 13 from the C-terminus (position 37 from the N-terminus) in the SARAH domain of VL-SARAH(37C) (Fv-clasp (v2)]}, and examined an S—S bond forming ability thereof in Experimental Example 1.

However, as shown in Experimental Example 1, it was surprisingly found that, among these mutants, Fv-clasp (v1') did not form stable S—S bonds between molecules, and Fv-clasp (v1") could not maintain good expression level and antigen binding ability.

That is, in order to suppress the intramolecular mobility in Fv-clasp to stabilize the heterodimer and improve the ability to crystallize, regarding the position of the S—S bond between the heterodimers to be introduced, it was found necessary to select the amino acid residue of antibody residue 112 according to Chothia numbering scheme in the VH region of VH(112C)-SARAH and the amino acid residue at position 13 from the C-terminus (position 37 from the N-terminus) in the SARAH domain of VL-SARAH(37C).

Example 2: Preparation of Fv-Clasp (v2) of P20.1 Antibody Using *E. coli* Expression System Using the *E. coli* expression system, VH(112C)-SARAH against P20.1 antibody (hereinafter, sometimes simply referred to as P20.1 antibody-VH(112C)-SARAH) represented by SEQ ID NO: 43, and VL-SARAH(37C) against P20.1 antibody (hereinafter, sometimes simply referred to as P20.1 antibody-VL-SARAH(37C)) represented by SEQ ID NO: 44 subjected to (1) gene recombination/expression step and solubilization step, (2) refolding step, (3) concentration step, and (4) purification step to obtain Fv-clasp (v2) against P20.1 antibody (hereinafter, sometimes simply referred to as P20.1 antibody-Fv-clasp (v2)), in the same manner as in Comparative Example 1, except that a nucleic acid sequence encoding VH(112C)-SARAH against P20.1 antibody represented by SEQ ID NO: 41 was used in place of the nucleic acid sequence encoding P20.1 antibody-VH-SARAH (Y35C) represented by SEQ ID NO: 19, and a nucleic acid sequence encoding VL-SARAH(37C) against P20.1 antibody represented by SEQ ID NO: 42 was used in place of the nucleic acid sequence encoding VL-SARAH(M24C) against P20.1 antibody represented by SEQ ID NO: 20.

Figure 7:
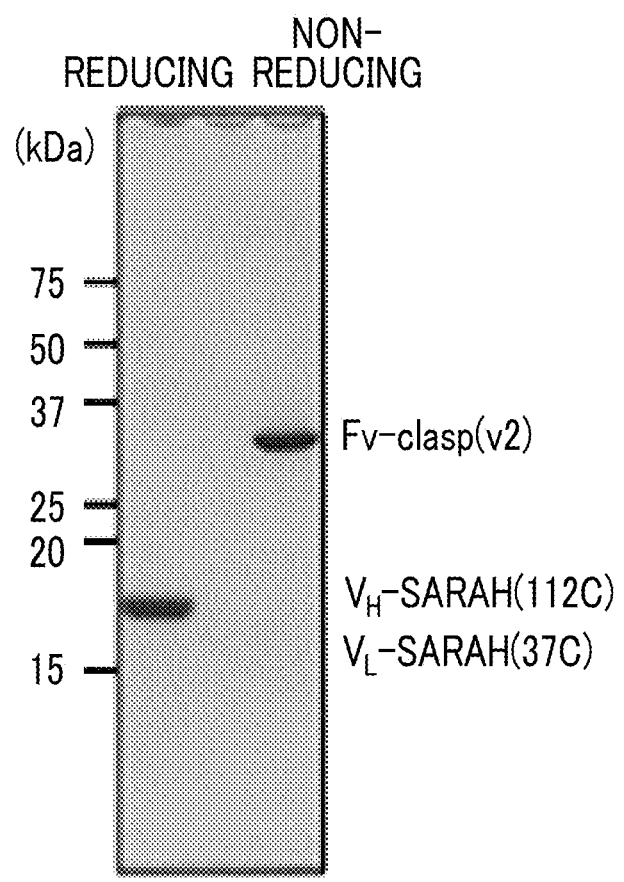
FIG. 7 is a view confirming that P20.1 antibody-Fv-clasp (v2) was obtained by SDS-PAGE in Example 2.

The results are shown in FIG. 7. In the figure, the lane on the left side is an electrophoretogram under reducing conditions and the lane on the right side is an electrophoretogram under non-reducing conditions. Under reducing conditions, P20.1 antibody-Fv-clasp (v2) was obtained by overlapping the bands of VH(112C)-SARAH against P20.1 antibody and VL-SARAH(37C) against P20.1 antibody around 18 kDa, and one band of P20.1 antibody-Fv-clasp (v2) was obtained around 35 kDa under non-reducing conditions. It was found in Fv-clasp (v2) that a recombinant protein correctly forming a heterodimer between VH(112C)-SARAH and VL-SARAH(37C) even in an *E. coli* expression system to form an S—S bond can be obtained with very high purity.

In addition, it is obvious that the obtained P20.1 antibody-Fv-clasp (v2) has an activity as an anti-C8 peptide antibody since it is purified with a resin in which an antigen molecule C8 peptide was immobilized, in the above-mentioned purification process.

That is, it was found that Fv-clasp (v2) can be conveniently produced irrespective of the type of the expression host cell, and has an antigen-binding activity (Examples 1 and 2).

Examples 3 to 10: Preparation of Fv-Clasp (v2) Using *E. coli* Expression System In the same manner as in Example 2, VH(112C)-SARAH against 93201 antibody, TS2/16 antibody, SG/19 antibody, t8E4 antibody, 9E10 antibody, 12CA5 antibody, t1E4 antibody, and NZ-1 antibody in place of VH(112C)-SARAH against P20.1 antibody, and VL-SARAH(37C) against 93201 antibody, TS2/16 antibody, SG/19 antibody, t8E4 antibody, 9E10 antibody, 12CA5 antibody, t1E4 antibody, and NZ-1 antibody in place of VL-SARAH(37C) against P20.1 antibody were subjected to (1) gene recombination/expression step and solubilization step, (2) refolding step, (3) concentration step, and (4) purification step to prepare Fv-clasp (v2) against each antibody (hereinafter, sometimes simply referred to as the name of each antibody-Fv-clasp (v2)).

The sequences of the nucleic acids used and the sequences of the prepared proteins are shown in Tables 2 and 3 below, respectively.

TABLE 2

| Antibody | | Nucleic acid sequence encoding VH(112C)-SARAH against each antibody | Nucleic acid sequence encoding VL-SARAH(37C) against each antibody |
|---|---|---|---|
| Example 3 | 93201 antibody | SEQ ID NO: 45 | SEQ ID NO: 53 |
| Example 4 | TS2/16 antibody | SEQ ID NO: 46 | SEQ ID NO: 54 |
| Example 5 | SG/19 antibody | SEQ ID NO: 47 | SEQ ID NO: 55 |
| Example 6 | t8E4 antibody | SEQ ID NO: 48 | SEQ ID NO: 56 |
| Example 7 | 9E10 antibody | SEQ ID NO: 49 | SEQ ID NO: 57 |
| Example 8 | 12CA5 antibody | SEQ ID NO: 50 | SEQ ID NO: 58 |
| Example 9 | t1E4 antibody | SEQ ID NO: 51 | SEQ ID NO: 59 |
| Example 10 | NZ-1 antibody | SEQ ID NO: 52 | SEQ ID NO: 60 |

TABLE 3

|  | Antibody | Amino acid sequence of VH(112C)-SARAH against each antibody | Amino acid sequence of VL-SARAH(37C) against each antibody |
|---|---|---|---|
| Example 3 | 93201 antibody | SEQ ID NO: 61 | SEQ ID NO: 69 |
| Example 4 | TS2/16 antibody | SEQ ID NO: 62 | SEQ ID NO: 70 |
| Example 5 | SG/19 antibody | SEQ ID NO: 63 | SEQ ID NO: 71 |
| Example 6 | t8E4 antibody | SEQ ID NO: 64 | SEQ ID NO: 72 |
| Example 7 | 9E10 antibody | SEQ ID NO: 65 | SEQ ID NO: 73 |
| Example 8 | 12CA5 antibody | SEQ ID NO: 66 | SEQ ID NO: 74 |
| Example 9 | t1E4 antibody | SEQ ID NO: 67 | SEQ ID NO: 75 |
| Example 10 | NZ-1 antibody | SEQ ID NO: 68 | SEQ ID NO: 76 |

Figure 8:
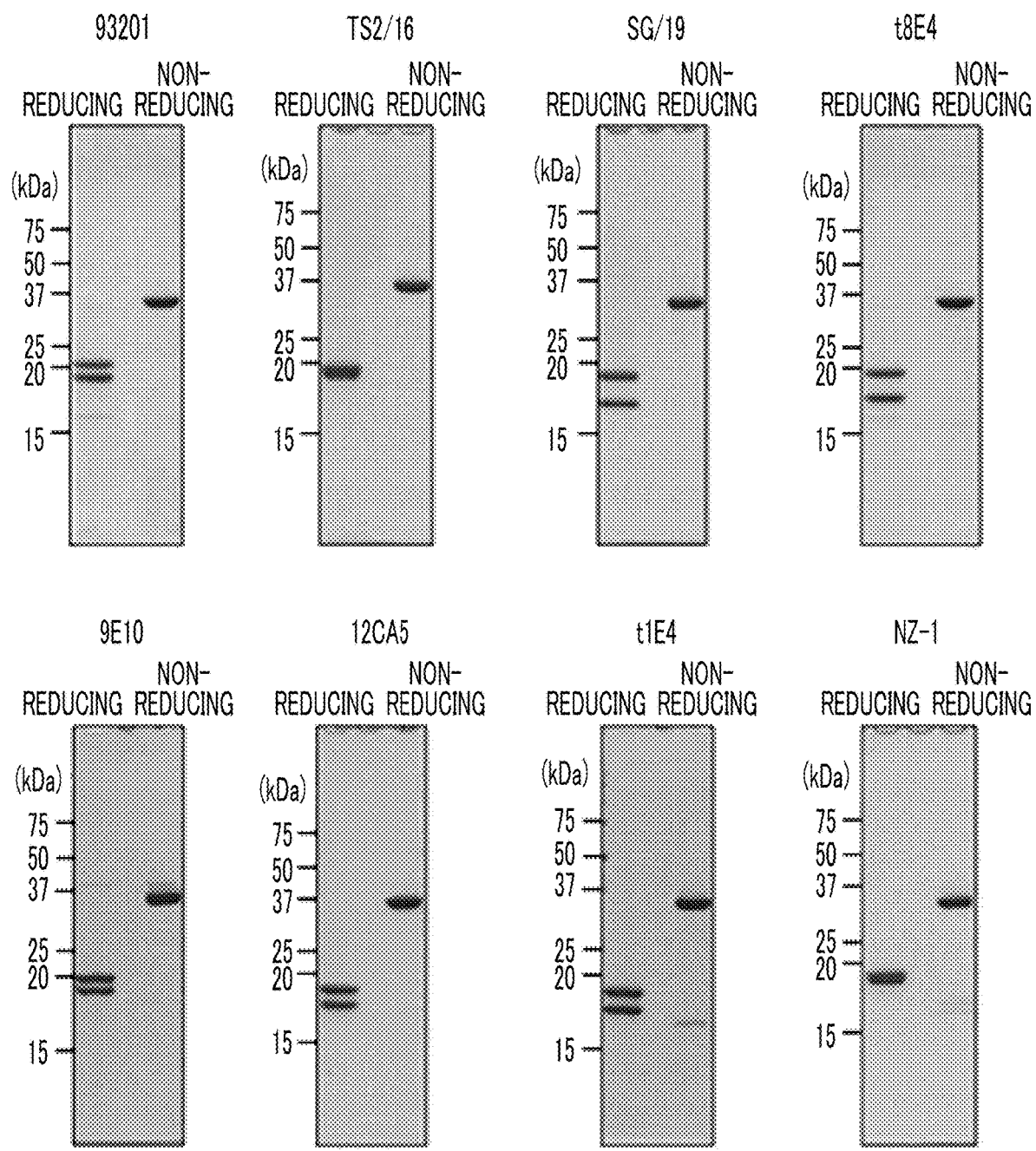
FIG. 8 is a view confirming that a variety of Fv-clasp (v2) was obtained by SDS-PAGE in Examples 3 to 10.

The results are shown in FIG. 8. In the figure, the lane on the left side is an electrophoretogram under reducing conditions and the lane on the right side is an electrophoretogram under non-reducing conditions. Similarly to the P20.1 antibody-Fv-clasp (v2) obtained in Example 2, in all of Fv-clasp (v2) of eight types of antibodies, bands corresponding to VH(112C)-SARAH and VL-SARAH(37C) against each antibody were obtained around 18 to 20 kDa under reducing conditions, and one band of Fv-clasp (v2) against each antibody was obtained around 35 to 37 kDa under non-reducing conditions.

That is, it was found that all of Fv-clasp (v2) of these eight antibodies prepared in the *E. coli* expression system correctly form a heterodimer between VH(112C)-SARAH and VL-SARAH(37C) to form an S—S bond and therefore can be purified with high purity.

Experimental Example 2: Confirmation of Antigen-Binding Activity of Fv-Clasp (v2)

The fact that Fv-clasp (v2) against a variety of antibodies obtained in Examples 3 to 10 has an antigen-binding activity was confirmed by peak shifts of gel filtration chromatography or biolayer interferometry, respectively.

For Fv-clasp (v2) against 93201 antibody, TS2/16 antibody, SG/19 antibody, and t8E4 antibody, each Fv-clasp (v2) was confirmed to form a stable complex with the respective antigen molecules [SORLA Vps10p domain represented by SEQ ID NO: 77 for Fv-clasp (v2) against 93201 antibody; Integrin α6β1, t8E4 antibody consisting of α6 chain represented by SEQ ID NO: 78 and 131 chain represented by SEQ ID NO: 79 for Fv-clasp (v2) against TS2/16 antibody and Fv-clasp (v2) against SG/19 antibody; and HGF represented by SEQ ID NO: 80 for Fv-clasp (v2) against t8E4 antibody] by peak shifts of gel filtration chromatography.

Figure 9:
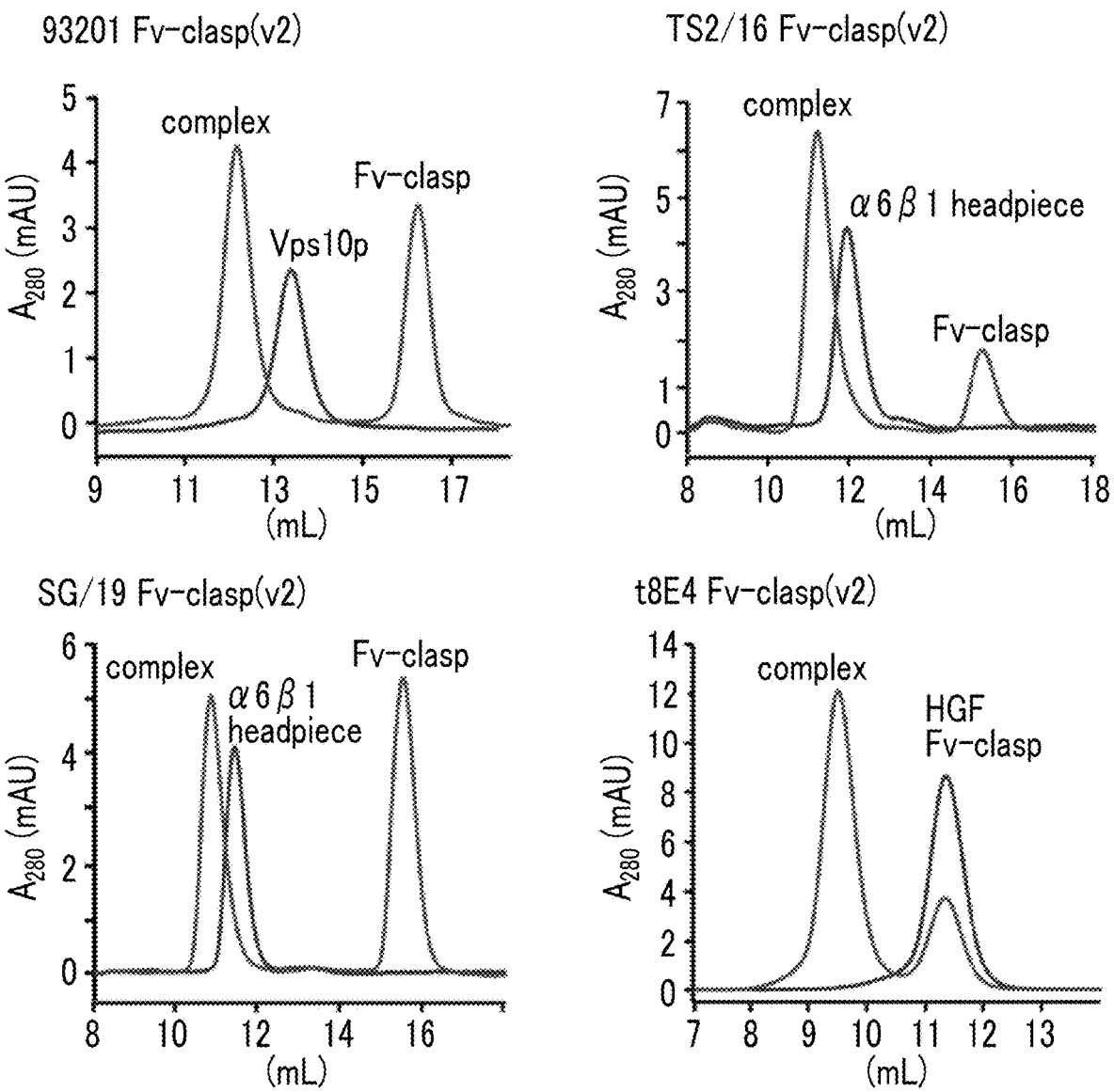
FIG. 9 is a view confirming that a variety of Fv-clasp (v2) had an antigen-binding activity by gel filtration chromatography in Experimental Example 2.

The results are shown in FIG. 9. As Fv-clasp (v2) against any antibody shifted in peak due to binding with the antigen protein; Fv-clasp (v2) against a variety of antibodies was found to have an antigen-binding activity.

In addition, for Fv-clasp (v2) against 9E10 antibody and Fv-clasp (v2) against 12CA5 antibody, the binding of each Fv-clasp (v2) to Myc tag-added T4L protein represented by SEQ ID NO: 81 or HA tag-added T4L protein represented by SEQ ID NO: 82, which is the respective antigen molecule was analyzed in real time by biolayer interferometry using Octet Red96 (manufactured by Primtech Corporation), and compared with the binding ability of the original antibodies (9E10 antibody and 12CA5 antibody) to antigen molecules.

Figure 10:
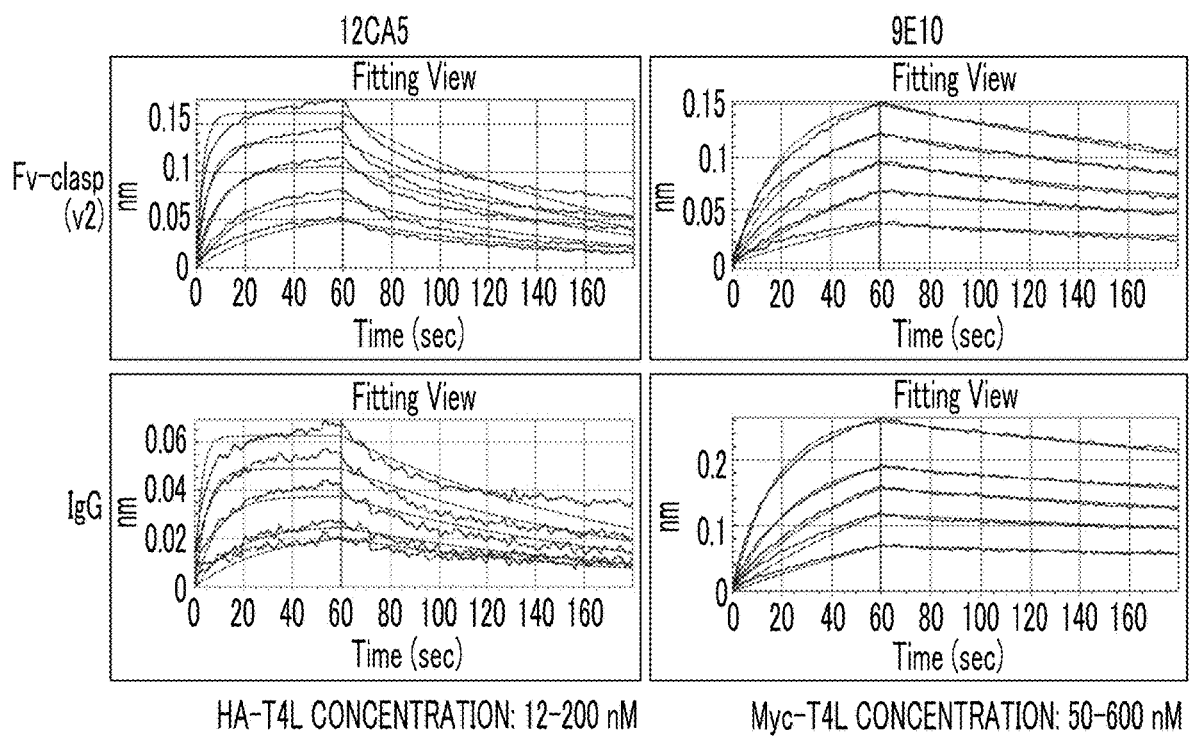
FIG. 10 is a view confirming that a variety of Fv-clasp (v2) had an antigen-binding activity by biolayer interferometry in Experimental Example 2.

The results are shown in FIG. 10. It was found that Fv-clasp (v2) against any antibody has the same degree of antigen-binding activity (antigen affinity) as that of the original antibody.

It should be noted that, with respect to Fv-clasp (v2) against NZ-1 antibody and Fv-clasp (v2) against t1E4 antibody, in Example 14 and Example 17 to be described later, crystal structure analysis for each Fv-clasp (v2) was carried out in the form of a complex with each antigen, and it was directly confirmed that each Fv-clasp (v2) forms a 1:1 complex with the antigen in the crystal. From these results, it was found that Fv-clasp (v2) against a variety of antibodies has an antigen-binding activity.

Example 11: Crystal Structure Analysis of Fv-Clasp (v2) Against TS2/16 Antibody

Crystallization of TS2/16 antibody-Fv-clasp (v2) was carried out in the same method as in Comparative Example 4, using Fv-clasp (v2) against TS2/16 antibody (hereinafter, sometimes simply referred to as TS2/16 antibody-Fv-clasp (v2)) prepared in Example 4.

However, 4.9 mg/mL of a TS2/16 antibody-Fv-clasp (v2) solution was used as a crystallization sample, and the screening kits used were Classics Neo Suite (manufactured by QIAGEN GmbH) (96 conditions) and Wizard Classic 1 & 2 (manufactured by Rigaku Corporation) (96 conditions).

As a result, in the screening stage, crystals were obtained in 1 condition (0.5%) out of 192 conditions. With respect to the obtained crystals, X-ray diffraction data was measured in the same manner as in Comparative Example 5, and data was obtained at a resolution of 2.04 Å, so that the structure could be determined.

Figure 11:
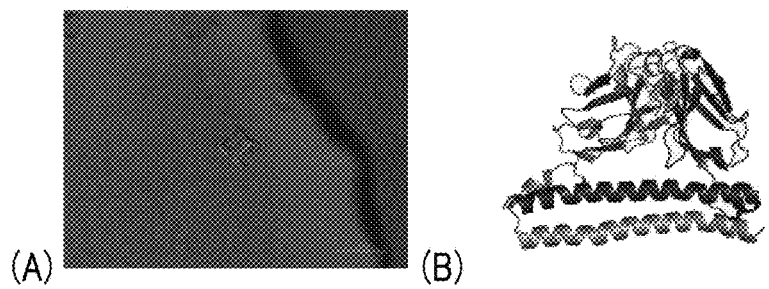
FIG. 11(A) is a micrograph of crystals obtained for TS2/16 antibody-Fv-clasp (v2) in Example 11.
FIG. 11(B) shows the result of X-ray crystallography of TS2/16 antibody-Fv-clasp (v2) carried out in Example 11.

The results are shown in FIG. 11. Fv-clasp (v2) was found to have an ability to crystallize. Generally, crystals are not normally obtained with full-length antibodies, and crystals cannot often be obtained with conventional fragment antibodies (Fab fragments or single chain antibody (scFv) fragments), so antibodies with unknown three-dimensional structure analysis of antigen-determining sites are present. Since Fv-clasp (v2) has an ability to crystallize and is easily crystallized, it was found that Fv-clasp (v2) is particularly useful in three-dimensional structure analysis of antigen-determining sites of antibodies.

Examples 12 to 14: Crystal Structure Analysis of Complex of Variety of Fv-Clasp (v2) and Antigen In the same manner as in Comparative Example 4, crystallization was carried out on a complex of P20.1 antibody-Fv-clasp (v2) prepared in Example 2 and C8 peptide which is an antigen molecule of P20.1 antibody represented by SEQ ID NO: 21 (Example 12), a complex of 12CA5 antibody-Fv-clasp (v2) prepared in Example 8 and HA peptide which is an antigen molecule of 12CA5 antibody represented by SEQ ID NO: 30 (Example 13), and a complex of NZ-1 antibody-Fv-clasp (v2) prepared in Example 10 and PA peptide which is an antigen molecule of NZ-1 antibody represented by SEQ ID NO: 83 (Example 14).

However, for the complex of P20.1 antibody-Fv-clasp (v2) and C8 peptide, a mixture of both so that the final concentrations thereof were 11 mg/mL and 2 mM, respectively, was used as a crystallization sample, and the screening kits used were Classics Neo Suite (manufactured by QIAGEN GmbH) (96 conditions), Classics II Suite (manufactured by QIAGEN GmbH) (96 conditions), Wizard Classic 1 & 2 (manufactured by Rigaku Corporation) (96 conditions), and JCSG+ (manufactured by Molecular Dimensions Limited) (96 conditions). For the complex of 12CA5 antibody-Fv-clasp (v2) and HA peptide, a mixture of both so that the final concentrations thereof were 7 mg/mL and 1 mM, respectively, was used as a crystallization sample, and the screening kits used were Classics Neo Suite (manufactured by QIAGEN GmbH) (96 conditions), Classics II Suite (manufactured by QIAGEN GmbH) (96 conditions), and Wizard Classic 1 & 2 (manufactured by Rigaku Corporation) (96 conditions). For the complex of NZ-1 antibody-Fv-clasp (v2) and PA peptide, a mixture of both so that the final concentrations thereof were 3.8 mg/mL and 1 mM, respectively, was used as a crystallization sample, and the screening kits used were Classics Neo Suite (manufactured by QIAGEN GmbH) (96 conditions), and Wizard Classic 1 & 2 (manufactured by Rigaku Corporation) (96 conditions).

As a result, in the screening stage, crystals were obtained in 35 conditions (9.1%) out of 384 conditions for the complex of P20.1 antibody-Fv-clasp (v2) and C8 peptide; crystals were obtained in 74 conditions (25.7%) out of 288 conditions for the complex of 12CA5 antibody-Fv-clasp (v2) and HA peptide; and crystals were obtained in 6 conditions (3.1%) out of 192 conditions for the complex of NZ-1 antibody-Fv-clasp (v2) and PA peptide.

For the complex of 12CA5 antibody-Fv-clasp (v2) and HA peptide and the complex of NZ-1 antibody-Fv-clasp (v2) and PA peptide, X-ray diffraction data was measured in the same manner as in Comparative Example 5 using the crystals obtained in the screening. Data were obtained at 2.45 Å resolution and 2.15 Å resolution, respectively. In addition, for the complex of P20.1 antibody-Fv-clasp (v2) and C8 peptide, the crystallization conditions were optimized based on the conditions of the crystals obtained in the screening, and X-ray diffraction data was measured using the crystals obtained as a result. Data with a resolution of 1.17 Å was obtained. Using the obtained X-ray diffraction data, the structure was determined in the same manner as in Comparative Example 5. However, the search model of molecular replacement with respect to the Fv region was the structure of the complex of P20.1 antibody-Fv-clasp (v1) and C8 peptide for P20.1 antibody-Fv-clasp (v2), the structure of the complex of 12CA5 antibody-Fv-clasp (v1) and HA peptide for 12CA5 antibody-Fv-clasp (v2), and the structure of NZ-1 Fab (PDB ID: 4YO0) for NZ-1 antibody-Fv-clasp (v2).

Figure 12:
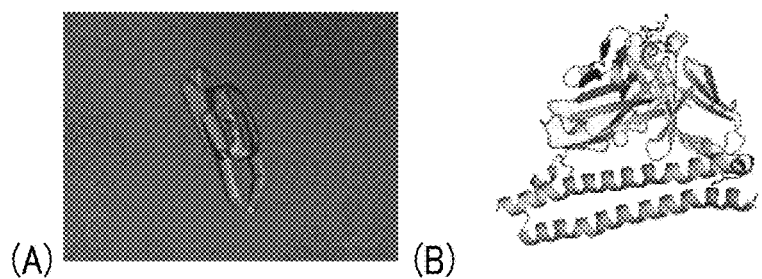
FIG. 12(A) is a micrograph of crystals obtained for a complex of P20.1 antibody-Fv-clasp (v2) and antigen molecule in Example 12.
FIG. 12(B) shows the result of X-ray crystallography of the complex of P20.1 antibody-Fv-clasp (v2) and antigen molecule carried out in Example 12.
Figure 13:
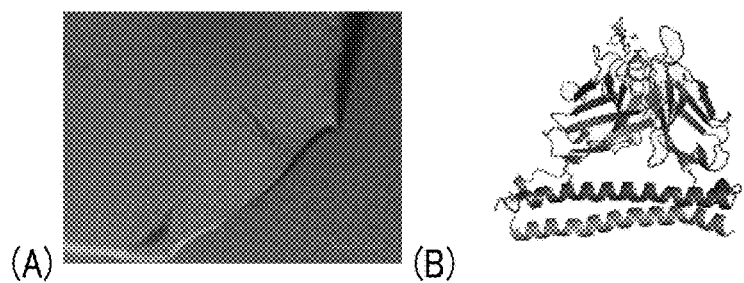
FIG. 13(A) is a micrograph of crystals obtained for a complex of 12CA5 antibody-Fv-clasp (v2) and antigen molecule in Example 13.
FIG. 13(B) shows the result of X-ray crystallography of the complex of 12CA5 antibody-Fv-clasp (v2) and antigen molecule carried out in Example 13.
Figure 14:
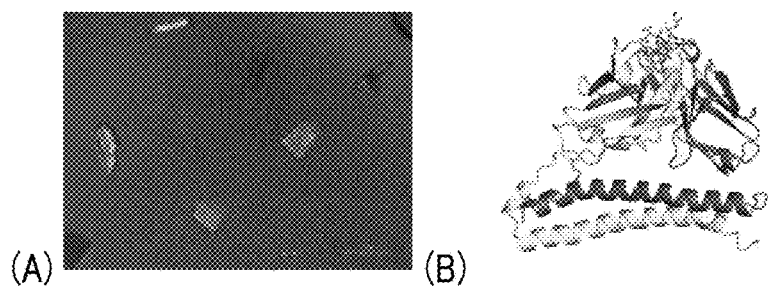
FIG. 14(A) is a micrograph of crystals obtained for a complex of NZ-1 antibody-Fv-clasp (v2) and antigen molecule in Example 14.
FIG. 14(B) shows the result of X-ray crystallography of the complex of NZ-1 antibody-Fv-clasp (v2) and antigen molecule carried out in Example 14.

The results are shown in FIGS. 12 to 14.

Fv-clasp (v1) and Fv-clasp (v2) will be compared and discussed below.

As a result of Comparative Example 4, the complex of P20.1 antibody-Fv-clasp (v1) obtained in the *E. coli* expression system and C8 peptide was examined in 480 conditions but no crystal was obtained at all, and the crystals were obtained with a probability of 3.6% only in a case of being prepared in an animal cell expression system; whereas as a result of Example 12, even in a case where the complex of P20.1 antibody-Fv-clasp (v2) and C8 peptide were obtained in the *E. coli* expression system, crystals were obtained in 35 conditions (9.1%) out of 384 conditions, and crystals optimized for crystallization conditions gave very high resolution data with resolution of 1.17 Å.

In addition, as a result of Comparative Example 6, crystals were obtained in 51 conditions (17.7%) out of 288 conditions as for the complex of 12CA5 antibody-Fv-clasp (v1) and HA peptide in the screening stage, and only data with low resolution of approximately 4 Å resolution to 9 Å resolution was obtained from the crystals; whereas, as a result of Example 13, although the screening was carried out under the same conditions (protein concentration, antigen concentration, type of screening kit used) as the complex of 12CA5 antibody-Fv-clasp (v1) and HA peptide, crystals were obtained in 74 conditions (25.7%) out of 288 conditions as for the complex of 12CA5 antibody-Fv-clasp (v2) and HA peptide in the screening stage, and high resolution data with resolution of 2.45 Å was obtained from the crystals.

From these results, it was found that Fv-clasp (v2) having an ability to crystallize can be obtained regardless of the host at the time of expression although Fv-clasp (v1) may not have an ability to crystallize in some cases obtained in the *E. coli* expression system. Since *E. coli* is easier to handle than animal cells, Fv-clasp (v2) is more useful than Fv-clasp (v1), particularly in that one having an ability to crystallize can be obtained in an *E. coli* expression system.

In addition, it was found that, even in a case where Fv-clasp (v1) obtained in the *E. coli* expression system has an ability to crystallize, Fv-clasp (v2) has a higher ability to crystallize than Fv-clasp (v1) (easy to crystallize), and therefore a high-resolution crystal can be obtained.

Examples 15 to 17: Crystal Structure Analysis of Complex of Variety of Fv-Clasp (v2) and Crystallization-Resistant Antigen Regarding SORLA (neuronal sorting receptor) Vps10p domain, integrin α6β1, and hepatocyte growth factor (HGF) which are crystallization-resistant proteins, a complex of Vps10p represented by SEQ ID NO: 77 and 93201 antibody-Fv-clasp (v2) prepared in Example 3 (Example 15), a complex of integrin α6β1 represented by SEQ ID NO: 78 and SEQ ID NO: 79 and TS2/16 antibody-Fv-clasp (v2) prepared in Example 4 (Example 16), and a complex of HGF represented by SEQ ID NO: 80 and t1E4 antibody-Fv-clasp (v2) prepared in Example 9 (Example 17) were subjected to crystallization in the same manner as in Comparative Example 4.

However, for the complex of Vps10p and 93201 antibody-Fv-clasp (v2), a mixture of both so that the concentrations thereof were set to 3 mg/mL and 1.5 mg/mL, respectively, was used as a crystallization sample, and the screening kits used were Classics Neo Suite (manufactured by QIAGEN GmbH) (96 conditions) for the former, and Classics Neo Suite (manufactured by QIAGEN GmbH) (96 conditions) and Wizard Classic 1 & 2 (manufactured by Rigaku Corporation) (96 conditions) for the latter. For the complex of integrin α6β1 and TS2/16 antibody-Fv-clasp (v2), a mixture of both so that the concentrations thereof were respectively set to 9.2 mg/mL was used as a crystallization sample, and the screening kits used were Classics Neo Suite (manufactured by QIAGEN GmbH) (96 conditions), Wizard Classic 1 & 2 (manufactured by Rigaku Corporation) (96 conditions), and ProPlex (manufactured by Molecular Dimensions Limited) (96 conditions). For the complex of HGF and t1E4 antibody-Fv-clasp (v2), a mixture of both so that the concentrations thereof were respectively set to 9.7 mg/mL was used as a crystallization sample, and the screening kits used were Classics Neo Suite (manufactured by QIAGEN GmbH) (96 conditions), Classics II Suite (manufactured by QIAGEN GmbH) (96 conditions), Wizard Classic 1 & 2 (manufactured by Rigaku Corporation) (96 conditions), ProPlex (manufactured by Molecular Dimensions Limited) (96 conditions), and JCSG+(manufactured by Molecular Dimensions Limited) (96 Condition).

As a result, in the screening stage, crystals were obtained in 11 conditions (3.8%) out of 288 conditions as for the complex of Vps10p and 93201 antibody-Fv-clasp (v2); crystals were obtained in 2 conditions (0.7%) out of 288 conditions as for the complex of integrin α6β1 and TS2/16 antibody-Fv-clasp (v2); and crystals were obtained in 1 condition (0.2%) out of 480 conditions as for the complex of HGF and t1E4 antibody-Fv-clasp (v2).

With respect to the crystals of each of the obtained complexes, X-ray diffraction data was measured in the same manner as in Comparative Example 5, and X-ray crystallography of the complexes was carried out.

The results are shown in FIGS. 15 to 17. In the screening stage, for the complex of Vps10p and 93201 antibody-Fv-clasp (v2), data was obtained at 3.2 Å resolution; for the complex of integrin α6β1 and TS2/16 antibody-Fv-clasp (v2), data was obtained at 3.37 Å resolution; and for the complex of HGF and t1E4 antibody-Fv-clasp (v2), data was obtained at 4.1 Å resolution, and therefore the crystal structures thereof could be determined.

Further, as a result of optimization of the crystallization conditions, data was obtained at 2.59 Å resolution as for the complex of Vps10p and 93201 antibody-Fv-clasp (v2); and data was finally obtained at 3.05 Å resolution as for the complex of integrin α6β1 and TS2/16 antibody-Fv-clasp (v2), and therefore the crystal structures thereof could be determined.

Hereinafter, the function of promoting crystallization of Fv-clasp (v2) will be discussed.

Integrin is a multi-domain glycoprotein, and an extracellular domain thereof is known to undergo very large structural changes in conjunction with signal transduction, and crystallization alone was thought to be difficult. Therefore, the present inventors attempted crystallization of integrin using Fab of plural antibodies containing TS2/16 so far, but no crystals were obtained at all. However, as described above, by using a complex with Fv-clasp (v2) of TS2/16 antibody, data was obtained at a resolution of 3.37 Å even in the screening stage, and therefore the crystal structure thereof could be determined.

In addition, the present inventors attempted to analyze crystal structures of HGF and Fab of t1E4 antibody in the past but only crystals having a diffraction ability of about 9 Å at the maximum were obtained. However, as described above, by using Fv-clasp (v2), the crystal structure thereof could be determined with a resolution of 4.1 Å even in the screening stage.

From these results, it turned out that Fv-clasp (v2) has a function to promote its crystallization in a case of forming a complex with a protein, particularly a crystallization-resistant protein, which was found to be useful as a fragment antibody for promoting crystallization.

In addition, the present inventors attempted to analyze a crystal structure of a complex of Vps10p and propeptide in the past (Kitago, Y, et al. Structural basis for amyloidogenic peptide recognition by sorLA. Nature Struct. Mol. Biol. 22, pp. 199 to 206. (2015)). However, the crystal of the complex took about 1 to 2 months to precipitate, and the frequency of obtaining quality crystals that can withstand analysis was very low. However, as described above, by using Fv-clasp (v2), the crystal structure thereof can be determined at 3.2 Å resolution even in the screening stage and 2.59 Å resolution after optimization of crystallization conditions, and furthermore, these crystals could be reproducibly obtained in only one day.

That is, it turned out that Fv-clasp (v2) has a function to promote crystallization of proteins, particularly crystallization-resistant proteins with good reproducibility and in a short period of time, which was found to be useful as a fragment antibody for promoting crystallization.

Experimental Example 3: Heat Stability of Fv-Clasp (v2)

The heat stability of scFv, which is a conventional single chain antibody, and Fv-clasp (v1) and Fv-clasp (v2) were compared by the following method.

The single-chain Fv (scFv) of P20.1 antibody, which is a conventional fragment antibody, was prepared by *E. coli* expression and rewinding method by the method described in Japanese Patent No. 5257997. The scFv of NZ-1 antibody was prepared in the same manner as in the single chain antibody (scFv) of P20.1 antibody, except that the sequence represented by SEQ ID NO: 84 was used.

In addition, Fv-clasp (v1) against NZ-1 antibody and Fv-clasp (v1) against SG/19 antibody were prepared in the same manner as in Comparative Example 3, by subjecting each of VH-SARAH(Y35C) against NZ-1 antibody represented by SEQ ID NO: 85 and VL-SARAH(M24C) against NZ-1 antibody represented by SEQ ID NO: 86, and VH-SARAH(Y35C) against SG/19 antibody represented by SEQ ID NO: 87 and VL-SARAH(M24C) against SG/19 antibody represented by SEQ ID NO: 88 to (1) gene recombination/expression step and solubilization step, (2) refolding step, (3) concentration step, and (4) purification step.

The scFv of P20.1 antibody, scFv of NZ-1 antibody, Fv-clasp (v1) against NZ-1 antibody, and Fv-clasp (v1) against SG/19 antibody thus prepared, P20.1 antibody-Fv-clasp (v1) obtained in Comparative Example 1, 12CA5 antibody-Fv-clasp (v1) obtained in Comparative Example 3, P20.1 antibody-Fv-clasp (v2) prepared in Example 2, SG/19 antibody-Fv-clasp (v2) prepared in Example 5, 12CA5 antibody-Fv-clasp (v2) prepared in Example 8, and NZ-1 antibody-Fv-clasp (v2) prepared in Example 10 were subjected to thermal shift assay and the Tm value of each thereof was determined.

In the thermal shift assay, SYPRO Orange (manufactured by Thermo Fisher Scientific Inc.) was added to each sample, and the change in fluorescence value in a case where the temperature was raised from 25° C. to 85° C. was measured in real time, whereby the denaturation state of the protein was monitored, and the Tm value [° C.] was calculated from the obtained denaturation curve. The results are shown in Table 4 below. All units in the table are in ° C.

TABLE 4

|  | scFv | Fv-clasp(v1) | Fv-clasp(v2) |
| --- | --- | --- | --- |
| P20.1 | 61 | 59 | 65 |
| NZ-1 | 45.5 | 43 | 53 |
| 12CA5 | — | 58.5 | 67.5 |
| SG/19 | — | 44 | 55 |

From these experimental results, it was found that Fv-clasp (v2) has a higher Tm value than conventional fragment antibodies scFv and Fv-clasp (v1), and the difference therebetween reaches as high as 6° C. to 11° C. That is, since Fv-clasp (v2) is far more thermostable than conventional fragment antibodies, it also has high storage stability under refrigeration or at room temperature. Due to these properties, it is expected that Fv-clasp (v2) has quite advantageous properties not only for fragment antibodies and fragment antibody for promoting protein crystallization, but also for other applications.

The invention claimed is:

1. A fragment antibody comprising a complex of:
   (a) a peptide (VH(112C)-SARAH) in which an N-terminus of a SARAH domain is linked to a C-terminus of a heavy chain domain (VH region) of an antibody, and an amino acid residue of antibody residue 112 according to Chothia numbering scheme in the VH region is mutated to cysteine; and
   (b) a peptide (VL-SARAH(37C)) in which an N-terminus of a SARAH domain is linked to a C-terminus of a light chain domain (VL region) of an antibody, and an amino acid residue at position 13 from the C-terminus in the SARAH domain is mutated to cysteine,
   wherein (c) the VH(112C)-SARAH and the VL-SARAH (37C) are linked by a disulfide bond between the two cysteines.

2. The fragment antibody according to claim 1, wherein the SARAH domain in the VH(112C)-SARAH is represented by any one selected from SEQ ID NOs: 1 to 8, and the SARAH domain in the VL-SARAH(37C) is represented by any one selected from SEQ ID NOs: 9 to 16.

3. The fragment antibody according to claim 1, wherein the SARAH domain in the VH(112C)-SARAH is represented by SEQ ID NOs: 1 or 2, and the SARAH domain in the VL-SARAH(37C) is represented by SEQ ID NOs: 9 or 10.

4. A fragment antibody for promoting protein crystallization, the fragment antibody comprising a complex of:
   (a) a peptide (VH(112C)-SARAH) in which an N-terminus of a SARAH domain is linked to a C-terminus of a heavy chain domain (VH region) of an antibody, and an amino acid residue of antibody residue 112 according to Chothia numbering scheme in the VH region is mutated to cysteine; and
   (b) a peptide (VL-SARAH(37C)) in which an N-terminus of a SARAH domain is linked to a C-terminus of a light chain domain (VL region) of an antibody, and an amino acid residue at position 13 from the C-terminus in the SARAH domain is mutated to cysteine,
   wherein (c) the VH(112C)-SARAH and the VL-SARAH (37C) are linked by a disulfide bond between the two cysteines.

5. The fragment antibody for promoting protein crystallization according to claim 4, wherein the SARAH domain in the VH(112C)-SARAH is represented by any one selected from SEQ ID NOs: 1 to 8, and the SARAH domain in the VL-SARAH(37C) is represented by any one selected from SEQ ID NOs: 9 to 16.

6. The fragment antibody for promoting protein crystallization according to claim 4, wherein the SARAH domain in the VH(112C)-SARAH is represented by SEQ ID NOs: 1 or 2, and the SARAH domain in the VL-SARAH(37C) is represented by SEQ ID NOs: 9 or 10.

7. A method for crystallizing a protein, comprising contacting the fragment antibody according to claim 1 with said protein.

8. A method for crystallizing a protein, comprising contacting the fragment antibody according to claim 2 with said protein.

9. A method for crystallizing a protein, comprising contacting the fragment antibody according to claim 3 with said protein.

* * * * *